(12) United States Patent
Baker et al.

(10) Patent No.: US 10,818,377 B2
(45) Date of Patent: Oct. 27, 2020

(54) COMPUTATIONAL DESIGN OF SELF-ASSEMBLING CYCLIC PROTEIN HOMO-OLIGOMERS

(71) Applicant: University of Washington, Seattle, WA (US)

(72) Inventors: David Baker, Seattle, WA (US); Jorge Fallas, Seattle, WA (US); George Ueda, Seattle, WA (US); William H. Sheffler, Seattle, WA (US); Vanessa Nguyen, Seattle, WA (US)

(73) Assignee: University of Washington, Seattle, WA (US)

( * ) Notice: Subject to any disclaimer, the term of this patent is extended or adjusted under 35 U.S.C. 154(b) by 253 days.

(21) Appl. No.: 15/813,872

(22) Filed: Nov. 15, 2017

(65) Prior Publication Data

US 2018/0137234 A1    May 17, 2018
US 2019/0155988 A2    May 23, 2019

Related U.S. Application Data

(60) Provisional application No. 62/422,872, filed on Nov. 16, 2016.

(51) Int. Cl.

| | |
|---|---|
| *C07K 14/00* | (2006.01) |
| *G16B 5/00* | (2019.01) |
| *A61K 38/03* | (2006.01) |
| *G16B 15/30* | (2019.01) |
| *A61K 38/00* | (2006.01) |

(52) U.S. Cl.
CPC ............... *G16B 5/00* (2019.02); *A61K 38/03* (2013.01); *C07K 14/00* (2013.01); *G16B 15/30* (2019.02)

(58) Field of Classification Search
None
See application file for complete search history.

(56) References Cited

U.S. PATENT DOCUMENTS

| | | | |
|---|---|---|---|
| 7,479,536 B1 | 1/2009 | Kumar et al. | |
| 7,683,025 B2 | 3/2010 | Stupp et al. | |
| 2001/0049357 A1* | 12/2001 | De .................... | A61K 38/1709 424/85.2 |
| 2005/0209145 A1 | 9/2005 | Stupp et al. | |
| 2013/0071418 A1* | 3/2013 | Schein ............... | C07K 16/1081 424/186.1 |
| 2019/0309286 A1* | 10/2019 | Itzhaki ................ | C12N 15/62 |

OTHER PUBLICATIONS

Gallagher et al. (1997) Structure and Organization of the Human Ankyrin-1 Gene, J. Biol. Chem., vol. 272, No. 31, pp. 19220-19228.*
Jones et al. (2004) The diploid genome sequence of Candida albicans, Proc. Natl. Acad. Sci. USA, vol. 101, pp. 7329-7334.*
Sequence alignment (2020) p. 1.*
Adams, P. D. et al. PHENIX: a comprehensive Python-based system for macromolecular structure solution. Acta Crystallographica Section D-Biological Crystallography 66, 213-221, doi:10.1107/s0907444909052925 (2010).
Ali, M.H. and Imperiali, B., 2005. Protein oligomerization: how and why. Bioorganic & medicinal chemistry, 13(17), pp. 5013-5020.
Arnout R. D. Voet, H. N., Christine Addy, David Simoncini, Daiki Terada, Satoru Unzai,Sam-Yong Park, Kam Y. J. Zhang, and Jeremy R. H. Tame. Computational design of a self-assembling symmetrical β-propeller protein. PNAS 111, 15102-15107 (2014).
Bahadur, R. P., Chakrabarti, P., Rodier, F. & Janin, J. Dissecting subunit interfaces in homodimeric proteins. Proteins 53, 708-719 (2003).
Bahadur, R. P., Chakrabarti, P., Rodier, F. & Janin, J. A dissection of specific and non-specific protein—protein interfaces. J. Mol. Biol. 336, 943-955 (2004).
Battye, T. G. G., Kontogiannis, L., Johnson, O., Powell, H. R. & Leslie, A. G. W. iMOSFLM: a new graphical interface for diffraction-image processing with MOSFLM. 36 Acta Crystallographica Section D-Biological Crystallography 67, 271-281, doi:10.1107/s0907444910048675 (2011).
Boyken, S. E. et al. De novo design of protein homo-oligomers with modular hydrogen-bond network-mediated specificity. Science 352, 680-687 (2016).
Brunette, T. J. et al. Exploring the repeat protein universe through computational protein design. Nature 528 580-584 (2015).
Chen, R. & Weng, Z. P. Docking unbound proteins using shape complementarity, desolvation, and electrostatics. Proteins 47, 281-294 (2002).
Chenna, R. et al. Multiple sequence alignment with the Clustal series of programs. Nucleic Acids Research 31, 3497-3500, doi:10.1093/nar/gkg500 (2003).
Davis, I. W. et al. MolProbity: all-atom contacts and structure validation for proteins and nucleic acids. Nucleic Acids Research 35, W375-W383, doi:10.1093/nar/gkm216 (2007).
DeBartolo, J., Dutta, S., Reich, L. & Keating, A. E. Predictive Bcl-2 family binding models rooted in experiment or structure. J. Mol. Biol. 422, 124-144 (2012).
Der, B. S. et al. Metal-mediated affinity and orientation specificity in a computationally designed protein homodimer. J. Am. Chem. Soc. 134, 375-385 (2012).
Dyer, K. N. et al. High-Throughput SAXS for the Characterization of Biomolecules in Solution: A Practical Approach. Structural Genomics: General Applications 1091, 245-258, doi:10.1007/978-1-62703-691-7_18 (2014).
Emsley, P. & Cowtan, K. Coot: model-building tools for molecular graphics. Acta Crystallographica Section D-Biological Crystallography 60, 2126-2132, doi:10.1107/s0907444904019158 (2004).

(Continued)

*Primary Examiner* — Manjunath N Rao
*Assistant Examiner* — Samuel W Liu
(74) *Attorney, Agent, or Firm* — McDonnell Boehnen Hulbert & Berghoff LLP

(57) ABSTRACT

Described herein are polypeptides capable of self-assembling to form homo-oligomers, and methods for designing such polypeptides.

13 Claims, 13 Drawing Sheets

Specification includes a Sequence Listing.

(56) References Cited

OTHER PUBLICATIONS

Fleishman, S. J. et al. RosettaScripts: a scripting language interface to the Rosetta macromolecular modeling suite. PLoS One 6, e20161 (2011).

Fletcher, J. M. et al. A basis set of de novo coiled-coil peptide oligomers for rational protein design and synthetic biology. ACS Synth. Biol. 1, 240-250 (2012).

Goodsell, D. S. & Olson, A. J. Structural symmetry and protein function. Annu. Rev. Biophys. Biomol. Struct. 29, 105-153 (2000).

Gray, J. J. & Baker, D. Protein—protein docking predictions with RosettaDock. Biophys. J. 86, 306A-306A (2004).

Gray, J. J. et al. Protein—protein docking with simultaneous optimization of rigid-body displacement and side-chain conformations. J. Mol. Biol. 331, 281-299 (2003).

Huang, P. S. et al. De novo design of an ideal TIM-barrel scaffold. Protein Sci. 24, 186-186 (2015).

Huang, P.-S. et al. High thermodynamic stability of parametrically designed helical bundles. Science 346, 481-485 (2014).

Janin, J., Bahadur, R. P. & Chakrabarti, P. Protein—protein interaction and quaternary structure. Q. Rev. Biophys. 41, 133-180 (2008).

Kabsch, W. XDS. Acta Crystallographica Section D-Biological Crystallography 66, 125-132, doi:10.1107/s0907444909047337 (2010).

Koga, N. et al. Principles for designing ideal protein structures. Nature 491, 222-227 (2012).

Leaver-Fay, A. et al. in Methods in Enzymology, vol. 487: Computer Methods, Pt C Methods in Enzymology (eds M. L. Johnson & L. Brand) 545-574 (Elsevier Academic Press Inc, 2011).

Levy, E. D. & Teichmann, S. in Oligomerization in Health and Disease (eds Giraldo, J. & Ciruela, F.) 25-51 (Progress in Molecular Biology and Translational Science 117, 2013).

Levy, E.D. and Teichmann, S., 2013. Structural, evolutionary, and assembly principles of protein oligomerization. Prog Mol Biol Transl Sci, 117, pp. 25-51.

Lin, Y.-R. et al. Control over overall shape and size in de novo designed proteins. Proc. Natl Acad. Sci. USA 112,E5478-E5485 (2015).

Lu, M., Dousis, A. D. & Ma, J. OPUS-PSP: an orientation-dependent statistical all-atom potential derived from side-chain packing. J. Mol. Biol. 376, 288-301 (2008).

Main, E. R. G., Xiong, Y., Cocco, M. J., D'Andrea, L. & Regan, L. Design of stable alpha-helical arrays from an idealized TPR motif. Structure 11, 497-508 (2003).

McCoy, A. J. et al. Phaser crystallographic software. Journal of Applied Crystallography 40, 658-674, doi:10.1107/s0021889807021206 (2007).

Menard, M. Blais, J.C., Hamon, L, Valéry, JM, and Xie, J. The Journal of organic chemistry 2005 vol. 70. / Issue 11 p. 4423-4430. Synthesis of orthogonally protected cyclic homooligomers from sugar amino acids.

Miles, et al. George Mason University. Geometry-based Computation of Symmetric Homooligomeric Protein Complexes, printed Mar. 2019.

Mou, Y., Huang, P. S., Hsu, F. C., Huang, S. J. & Mayo, S. L. Computational design and experimental verification of a symmetric protein homodimer. Proc. Natl Acad. Sci. USA 112, 10714-10719 (2015).

Nishi, H., Hashimoto, K., Madej, T. and Panchenko, A.R., 2013. Evolutionary, physicochemical, and functional mechanisms of protein homooligomerization. Progress in molecular biology and translational science, 117, p. 3.

Otwinowski, Z. & Minor, W. Processing of X-ray diffraction data collected in oscillation mode. Macromolecular Crystallography, Pt A 276, 307-326, doi:10.1016/s0076-6879(97)76066-x (1997).

Park, K. et al. Control of repeat-protein curvature by computational protein design. Nat. Struct. Mol. Biol. 22, 167-174 (2015).

Parmeggiani, F. et al. A general computational approach for repeat protein design. J. Mol. Biol. 427, 563-575 (2015).

Pechmann, S., Levy, E. D., Tartaglia, G. G. & Vendruscolo, M. Physicochemical principles that regulate the competition between functional and dysfunctional association of proteins. Proc. Natl Acad. Sci. USA 106, 10159-10164 (2009).

Pierce, B., Tong, W. W. & Weng, Z. P. M-Zdock: a grid-based approach for Cn symmetric multimer docking. Bioinformatics 21, 1472-1478 (2005).

Schneidman-Duhovny, D., Hammel, M. & Sali, A. FoXS: a web server for rapid computation and fitting of SAXS profiles. Nucleic Acids Res. 38, W540-W544 (2010).

Schneidman-Duhovny, D., Inbar, Y., Nussinov, R. & Wolfson, H. J. Patchdock and symmDock: servers for rigid and symmetric docking. Nucleic Acids Res. 33,3 W363-W367 (2005).

Sinha, S. K., Sirota, E. B., Garoff, S. & Stanley, H. B. X-Ray and Neutronscattering From Rough Surfaces. Physical Review B 38, 2297-2311, doi:10.1103/PhysRevB.38.2297 (1988).

Smart, O. S. et al. Exploiting structure similarity in refinement: automated NCS and target-structure restraints in BUSTER. Acta Crystallographica Section D-Biological Crystallography 68, 368-380, doi:10.1107/s0907444911056058 (2012).

Smock, R. G., Yadid, I., Dym, O., Clarke, J. & Tawfik, D. S. De novo evolutionary emergence of a symmetrical protein is shaped by folding constraints. Cell 164, 476-486 (2016).

Stranges, P. B., Machius, M., Miley, M. J., Tripathy, A. & Kuhlman, B. Computational design of a symmetric homodimer using β-strand assembly. Proc. Natl Acad. Sci. USA 108, 20562-20567 (2011).

Tyka, M. D. et al. Alternate States of Proteins Revealed by Detailed Energy Landscape Mapping. Journal of Molecular Biology 405, 607-618, doi:10.1016/j.jmb.2010.11.008 (2011).

Voet, A. R. D. et al. Computational design of a self-assembling symmetrical β-propeller protein. Proc. Natl Acad. Sci. USA 111, 15102-15107 (2014).

Wei, H. et al. Lysozyme-stabilized gold fluorescent cluster: synthesis and application as Hg2+ sensor. Analyst 135, 1406-1410 (2010).

Wyatt, P. J. Light-Scattering and the Absolute Characterization of Macromolecules. Analytica Chimica Acta 272, 1-40, doi:10.1016/0003-2670(93)80373-s (1993).

Zheng, W. H., Schafer, N. P., Davtyan, A., Papoian, G. A. & Wolynes, P. G. Predictive energy landscapes for protein—protein association. Proc. Natl Acad. Sci. USA 109, 19244-19249 (2012).

Zimm, B. H. Apparatus and Methods for Measurement and interpretation of the Angular Variation of Light Scattering. Journal of Chemical Physics 16, 1099-1116, doi:10.1063/1.1746740 (1948).

* cited by examiner

300

310 Determine a cycle of monomeric proteins using a computing device

↓

320 Determine a docking score for the cycle of monomeric proteins using the computing device, the docking score representing interaction between two or more monomeric proteins in the cycle of monomeric proteins with respect to a multi-dimensional rigid body transformation between one or more backbone atoms of the two or more monomeric proteins

↓

330 Determine whether the docking score for the cycle of monomeric proteins is a relatively-low docking score using the computing device

↓

340 After determining that the docking score for the cycle of monomeric proteins is a relatively-low docking score, determining one or more interfaces between the two or more monomeric proteins in the cycle of monomeric proteins using the computing device

↓

350 Generate an output related to the cycle of monomeric proteins

FIG. 3

| Res# | domain naORS | tpRS | 1 | 2 | 3 | 4 | 5 | 6 | 7 | 8 | 9 | 10 | 11 | 12 |
|---|---|---|---|---|---|---|---|---|---|---|---|---|---|---|
| 1 | Repeat 1 N | N | E | E | N | | | T | | N | E | | E | E |
| 2 | Repeat 1 S | D | R | E | L | E | S | L | | L | E | S | E | E |
| 3 | Repeat 1 A | A | E | E | E | | | R | S | E | E | | E | E |
| 4 | Repeat 1 E | E | M | L | K | L | A | V | S | K | L | A | L | L |
| 5 | Repeat 1 A | A | A | A | M | A | M | A | W | M | A | M | A | A |
| 6 | Repeat 1 W | W | A | L | K | D | K | L | V | K | L | K | L | L |
| 7 | Repeat 1 Y | K | L | L | A | L | M | L | M | A | L | M | L | L |
| 8 | Repeat 1 N | E | V | | | | | | L | | | K | | |
| 9 | Repeat 1 L | L | D | E | A | E | A | A | L | A | E | A | E | E |
| 10 | Repeat 1 G | G | A | L | M | A | A | L | L | M | L | A | L | L |
| 11 | Repeat 1 N | K | I | | | | | A | L | R | | | | |
| 12 | Repeat 1 A | V | M | A | A | A | A | A | S | A | A | | A | A |
| 13 | Repeat 1 Y | L | | L | R | | | A | L | R | K | | K | K |
| 14 | Repeat 1 Y | E | | | K | D | | Q | L | K | L | | L | L |
| 15 | Repeat 1 K | K | M | K | | E | | E | N | Q | | | | |
| 16 | Repeat 1 Q | Q | L | L | Q | | D | E | R | | E | D | E | E |
| 17 | Repeat 1 G | G | | | T | R | | | | T | R | I | R | R |
| 18 | Repeat 1 D | R | | E | | | D | | | | | | | |
| 19 | Repeat 1 Y | L | | | | | | | | | | | | |
| 20 | Repeat 1 D | D | R | R | T | R | I | E | S | T | R | I | R | R |

| # | Position | Residue | Extra |
|---|---|---|---|
| 63 | Repeat 2 A | A | |
| 64 | Repeat 2 L | L | |
| 65 | Repeat 2 E | E | |
| 66 | Repeat 2 L | L | |
| 67 | Repeat 2 D | D | |
| 68 | Repeat 2 P | P | |
| 69 | Repeat 3 N | N | |
| 70 | Repeat 3 N | D | |
| 71 | Repeat 3 A | A | |
| 72 | Repeat 3 E | E | |
| 73 | Repeat 3 A | A | |
| 74 | Repeat 3 W | W | |
| 75 | Repeat 3 Y | K | |
| 76 | Repeat 3 N | E | |
| 77 | Repeat 3 L | L | |
| 78 | Repeat 3 G | G | |
| 79 | Repeat 3 N | K | |
| 80 | Repeat 3 A | V | |
| 81 | Repeat 3 Y | L | |
| 82 | Repeat 3 Y | E | |
| 83 | Repeat 3 K | K | |

| Position | Repeat 4 | | | | | | |
|---|---|---|---|---|---|---|---|
| 105 | Repeat 4 | A | A | | | A | V | A |
| 106 | Repeat 4 | E | E | | | D | D | |
| 107 | Repeat 4 | A | A | | | A | | |
| 108 | Repeat 4 | K | W | | | L | I | |
| 109 | Repeat 4 | Q | K | | Q | K | E | |
| 110 | Repeat 4 | N | E | | | | | |
| 111 | Repeat 4 | L | L | | Q | L | L | |
| 112 | Repeat 4 | G | G | | L | L | I | |
| 113 | Repeat 4 | N | K | | N | N | E | |
| 114 | Repeat 4 | A | V | | | | | |
| 115 | Repeat 4 | K | L | | K | M | I | E |
| 116 | Repeat 4 | Q | E | | | M | A | E |
| 117 | Repeat 4 | K | K | | | D | R | |
| 118 | Repeat 4 | Q | K | E | | G | D | Q |
| 119 | Repeat 4 | G | L | E | | | G | |
| 120 | Repeat 4 | R | R | | | | | |
| 121 | Repeat 4 | - | L | | | | | |
| 122 | Repeat 4 | - | D | | | | | |
| 123 | Repeat 4 | - | E | | | | | |
| 124 | Repeat 4 | - | A | | | | | |
| 125 | Repeat 4 | - | A | | | | | |

| 126 | Repeat 4 - | E |
| 127 | Repeat 4 - | A |
| 128 | Repeat 4 - | Y |
| 129 | Repeat 4 - | K |
| 130 | Repeat 4 - | K |
| 131 | Repeat 4 - | A |
| 132 | Repeat 4 - | I |
| 133 | Repeat 4 - | E |
| 134 | Repeat 4 - | L |
| 135 | Repeat 4 - | D |
| 136 | Repeat 4 - | P |

FIGURE 4G

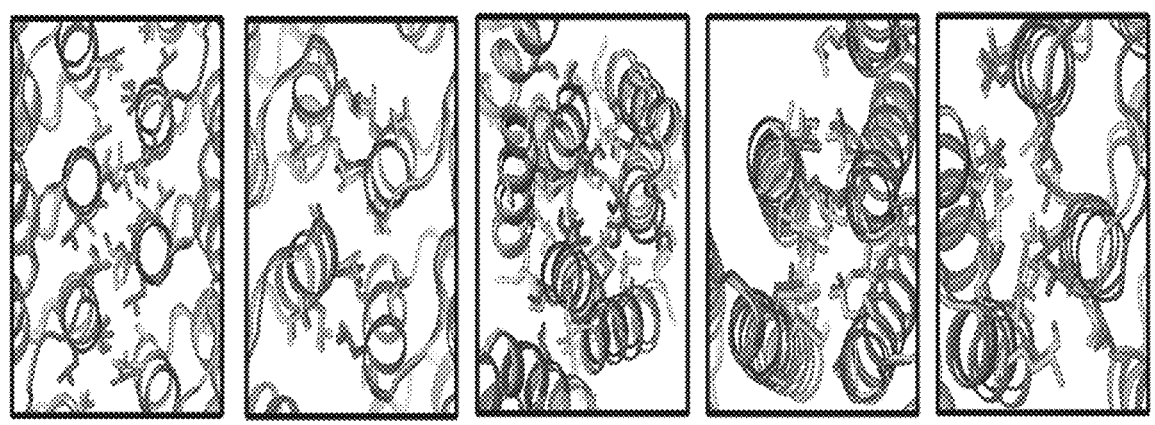
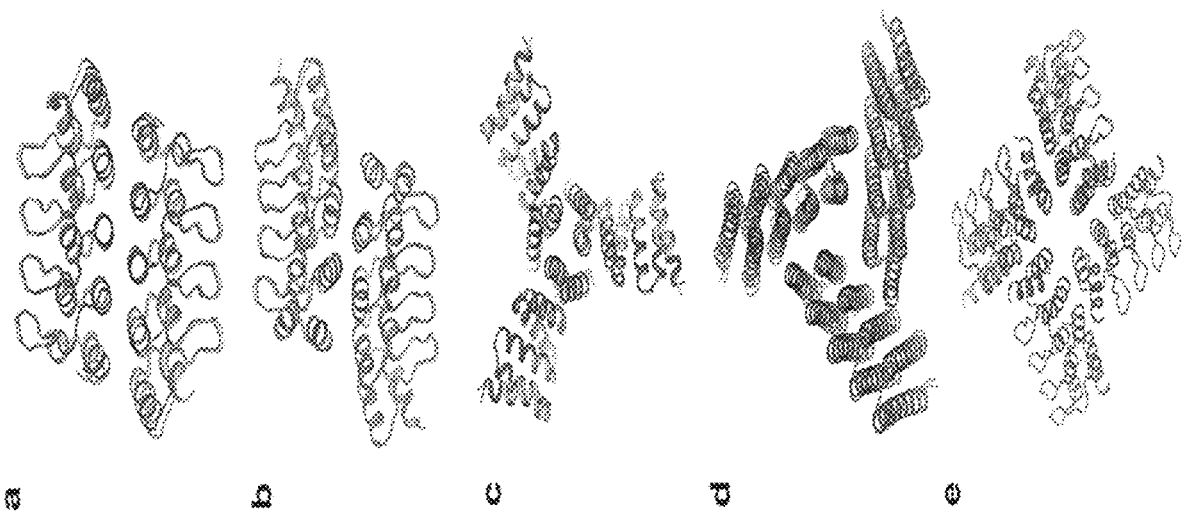
Figure 6

COMPUTATIONAL DESIGN OF SELF-ASSEMBLING CYCLIC PROTEIN HOMO-OLIGOMERS

RELATED APPLICATIONS

This application claims priority to U.S. Provisional Patent Application Ser. No. 62/422,872 filed Nov. 16, 2016, incorporated by reference herein in its entirety

BACKGROUND

Cyclic homo-oligomers assembled from multiple identical protein subunits symmetrically arranged around a central axis play key roles in many biological processes including catalysis, signaling and allostery. Despite their prevalence in natural systems, currently there is no systematic approach to design cyclic homo-oligomers starting from a monomeric protein structure.

SUMMARY OF THE INVENTION

In one aspect are provided polypeptides polypeptide comprising the general formula X1-X2-X3-X4-X5, wherein:
(a) X1 comprises the amino acid sequence that is selected from the group consisting of:
  (i) the amino acid sequence at least 50% identical along its length to SEQ ID NO:1,
  (ii) the amino acid sequence at least 50% identical along its length to SEQ ID NO: 2; and
  (iii) the amino acid sequence at least 50% identical along its length to SEQ ID NO:3;
(b) X2 comprises the amino acid sequence that is selected from the group consisting of:
  (i) the amino acid sequence at least 50% identical along its length to residues SEQ ID NO: 1, wherein X2 possesses changes from SEQ ID NO: 1 at least at residues 16, 20, and 24;
  (ii) the amino acid sequence at least 50% identical along its length to residues SEQ ID NO:2, wherein X2 possesses changes from SEQ ID NO:2 at least at residues 18, 22, and 26; and
  (iii) the amino acid sequence at least 50% identical along its length to residues SEQ ID NO:3, wherein X2 possesses changes from SEQ ID NO:3 at least at residues 18, 22, and 26; and
(c) X3, X4, and X5 are independently absent, or comprise the amino acid sequence that is selected from the group consisting of:
  (i) the amino acid sequence at least 50% identical along its length to SEQ ID NO:1,
  (ii) the amino acid sequence at least 50% identical along its length to SEQ ID NO:2; and
  (iii) the amino acid sequence at least 50% identical along its length to residues SEQ ID NO:3;
wherein the polypeptide does not comprise the amino acid sequence of SEQ ID NO: 5-7.

In another aspect, the invention provides polypeptides comprising the general formula X1-X2-X3-X4, wherein:
X1 is at least 50% identical along its length to residues 1-34 of the amino acid sequence of SEQ ID NO: 8, wherein the amino acid sequence of X1 differs from the amino acid sequence of residues 1-34 of SEQ ID NO: 8 at least at residues 6, 8, 13, 21, 25, and 28;
X2 is absent, or is at least 50% identical along its length to residues 36-68 of the amino acid sequence of SEQ ID NO: 8;
X3 is absent, or is at least 50% identical along its length to residues 69-102 of the amino acid sequence of SEQ ID NO: 8; and
X4 is absent, or is at least 50% identical along its length to residues 103-119 of the amino acid sequence of SEQ ID NO: 8.

In another aspect are provided polypeptides comprising the amino acid sequence at least 50% identical to the amino acid sequence of SEQ ID NO: 10, wherein all oligomerizing positions in SEQ ID NO: 10 have the amino acid residue shown in SEQ ID NO: 10, or conservative substitutions thereof, and wherein the polypeptide does not comprise acid sequence of SEQ ID NO: 9.

In a further aspect are provided polypeptides comprising the amino acid sequence at least 50% identical to SEQ ID NO: 11, wherein the polypeptide amino acid sequence differs from SEQ ID NO: 11 at least at residues 7, 8, 10, 14, 17, 118, 122, 146, 149, and 150.

In a still further aspect are provided polypeptides comprising the amino acid sequence that is at least 50% identical over its length to the amino acid sequence of a polypeptide selected from the group consisting of SEQ ID NOS: 10 and 12-40.

In a further aspect, a method is provided. A computing device determines a cycle of monomeric proteins. The computing device determines a docking score for the cycle of monomeric proteins. The docking score represents interaction between two or more monomeric proteins in the cycle of monomeric proteins with respect to a multi-dimensional rigid body transformation between three or more backbone atoms of the two or more monomeric proteins. The computing device determines whether the docking score for the cycle of monomeric proteins is a relatively-low docking score. After determining that the docking score for the cycle of monomeric proteins is a relatively-low docking score, the computing device determines one or more interfaces between the two or more monomeric proteins in the cycle of monomeric proteins. An output is generated related to the cycle of monomeric proteins.

In another aspect, a computing device is provided. The computing device includes one or more processors; and non-transitory data storage that is configured to store at least computer-readable instructions that, when executed by the one or more processors, cause the computing device to perform functions. The functions include: determining a cycle of monomeric proteins; determining a docking score for the cycle of monomeric proteins, the docking score representing interaction between two or more monomeric proteins in the cycle of monomeric proteins with respect to a multi-dimensional rigid body transformation between three or more backbone atoms of the two or more monomeric proteins; determining whether the docking score for the cycle of monomeric proteins is a relatively-low docking score; after determining that the docking score for the cycle of monomeric proteins is a relatively-low docking score, determining one or more interfaces between the two or more monomeric proteins in the cycle of monomeric proteins; and generating an output related to the cycle of monomeric proteins.

In another aspect, a non-transitory computer-readable medium is provided. The non-transitory computer-readable medium is configured to store at least computer-readable instructions that, when executed by one or more processors of a computing device, cause the computing device to perform functions. The functions include: determining a cycle of monomeric proteins; determining a docking score for the cycle of monomeric proteins, the docking score representing interaction between two or more monomeric proteins in the cycle of monomeric proteins with respect to a multi-dimensional rigid body transformation between three or more backbone atoms of the two or more monomeric proteins; determining whether the docking score for the cycle of monomeric proteins is a relatively-low docking score; after determining that the docking score for the cycle of monomeric proteins is a relatively-low docking score, determining one or more interfaces between the two or more monomeric proteins in the cycle of monomeric proteins; and generating an output related to the cycle of monomeric proteins.

In another aspect, a device is provided. The device includes: means for determining a cycle of monomeric proteins; determining a docking score for the cycle of monomeric proteins, the docking score representing interaction between two or more monomeric proteins in the cycle of monomeric proteins with respect to a multi-dimensional rigid body transformation between three or more backbone atoms of the two or more monomeric proteins; means for determining whether the docking score for the cycle of monomeric proteins is a relatively-low docking score; means for, after determining that the docking score for the cycle of monomeric proteins is a relatively-low docking score, determining one or more interfaces between the two or more monomeric proteins in the cycle of monomeric proteins; and means for generating an output related to the cycle of monomeric proteins.

BRIEF DESCRIPTION OF THE FIGURES

FIG. 3: A flowchart of a method.

FIG. 4A-G: Alignment of 1na0 or tpr repeat designed peptides with the 1na0 reference sequence (1naRS, SEQ ID NO: 8) or the tpr reference sequence (tpRS, SEQ ID NO: 41). Column 1: 1na0C3_1 (SEQ ID NO: 16); Column 2: 1na0C3_int2 (SEQ ID NO: 17); Column 3: 1na0C$_{3-3}$ (SEQ ID NO: 18); Column 4: 1na0C$_{3-5}$ (SEQ ID NO: 19); Column 5: 1na0C$_{3-7}$ (SEQ ID NO: 20); Column 6: 1na0C4_1 (SEQ ID NO: 21); Column 7: tpr1C4_2 (SEQ ID NO: 10); Column 8: T33_dn2A (SEQ ID NO: 33); Column 9: T33_dn2B (SEQ ID NO: 34); Column 10: T33_dn5A (SEQ ID NO: 35); Column 11: T33_dn10A (SEQ ID NO: 37); Column 12: I53_dn5B (SEQ ID NO: 40).

FIG. 6: Comparison between the experimentally determined crystal structures and corresponding design models. Crystal structures are shown in cyan and models in gray. Left column, full model and crystal structure superposition; Right column, superposition showing hydrophobic side chains at the designed interface. a, ank3C2_1 (r.ms.d. to model 1 Å) b, ank1C2_1 (r.ms.d. to model 0.9 Å) c, 1na0C3_3 (r.ms.d. to model 1 Å) d, HR00C3_2 (r.ms.d. to model 0.9 Å) e, ank1C4_2 pair of chains (r.ms.d. to model 1.1 Å)

DETAILED DESCRIPTION

Figure 1:
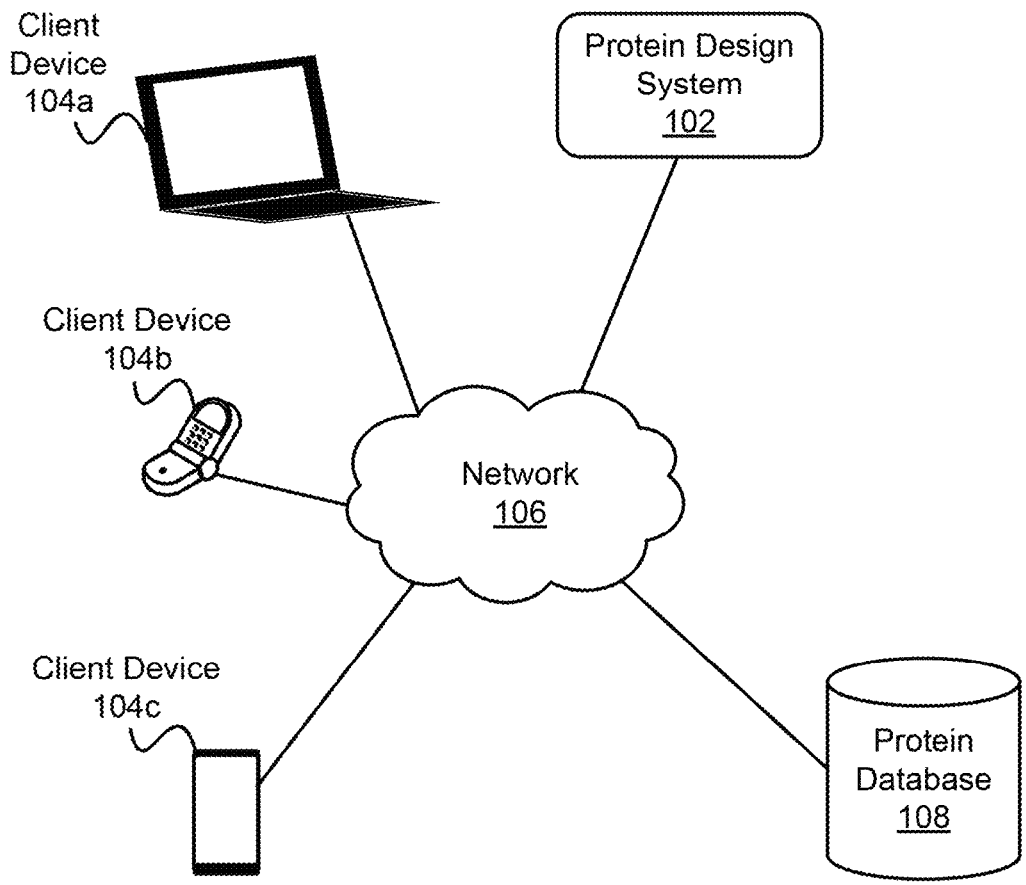
FIG. 1: A block diagram of an example computing network.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2$^{nd}$ Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In one aspect are provided isolated polypeptides comprising the general formula X1-X2-X3-X4-X5, wherein:
 (a) X1 comprises the amino acid sequence that is selected from the group consisting of:
  (i) the amino acid sequence at least 50% identical along its length to SEQ ID NO: 1,
  (ii) the amino acid sequence at least 50% identical along its length to SEQ ID NO: 2; and
  (iii) the amino acid sequence at least 50% identical along its length to SEQ ID NO:3;
 (b) X2 comprises the amino acid sequence that is selected from the group consisting of:
  (i) the amino acid sequence at least 50% identical along its length to residues SEQ ID NO:1, wherein X2 possesses changes from SEQ ID NO: 1 at least at residues 16, 20, and 24;
  (ii) the amino acid sequence at least 50% identical along its length to residues SEQ ID NO:2, wherein X2 possesses changes from SEQ ID NO:2 at least at residues 18, 22, and 26; and
  (iii) the amino acid sequence at least 50% identical along its length to residues SEQ ID NO:3, wherein X2 possesses changes from SEQ ID NO:3 at least at residues 18, 22, and 26; and (c) X3, X4, and X5 are independently absent, or comprise the amino acid sequence that is selected from the group consisting of:
 (i) the amino acid sequence at least 50% identical along its length to SEQ ID NO:1,
 (ii) the amino acid sequence at least 50% identical along its length to SEQ ID NO:2; and
 (iii) the amino acid sequence at least 50% identical along its length to residues SEQ ID NO:3;
wherein the polypeptide does not comprise the amino acid sequence of SEQ ID NO: 5-7.

Ank reference sequence (i.e.: includes SEQ ID NOS: 1, 2, and 3)

(SEQ ID NO: 4)
SELGKRLIEAAENGNKDRVKDLLENGADVNASDSDGKTPLHLAAENGHKE

VVKLL(I/L)S(Q/K)G(D/A)(P/D)(V/P/N)(N/T)(A/T/S)

(S/K)DSDG(K/R)TPLH(H/L/Y)AAENGHKE(V/I)VKLL(I/L)S (Q/K)G(D/A)(P/D)(V/P/N)(N/T)(A/T/S)(S/K)DSDG(K/R)T

PLH(H/L/Y)AAENGHKE(V/I)VKLL(I/L)S(Q/K)G(D/A)(P/D)

(V/P/N)(N/T)(A/T/S)SDSDGRTPLDLAREHGNEE(V/I)VKLLEKQ

Wild Type Ankyrins

> ank1
(SEQ ID NO: 5)
SELGKRLIEAAENGNKDRVKDLIENGADVNASDSDGRTPLHHAAENGHKE

VVKLLISKGADVNAKDSDGRTPLHHAAENGHKEVVKLLISKGADVNAKDS

DGRTPLHHAAENGHKEVVKLLISKGADVNTSDSDGRTPLDLAREHGNEEV

VKLLEKQ

> ank3
(SEQ ID NO: 6)
SELGKRLIEAAENGNKDRVKDLLENGADVNASDSDGKTPLHLAAENGHKE

VVKLLLSQGADPNAKDSDGKTPLHLAAENGHKEVVKLLLSQGADPNAKDS

DGKTPLHLAAENGHKEVVKLLLSQGADPNTSDSDGRTPLDLAREHGNEEV

VKLLEKQ

> ank4
(SEQ ID NO: 7)
SELGKRLIEAAENGNKDRVKDLLENGADPNASDSDGRTPLHYAAENGHKE

IVKLLLSKGADPNAKDSDGRTPLHYAAENGHKEIVKLLLSKGADPNAKDS

DGRTPLHYAAENGHKEIVKLLLSKGADPNTSDSDGRTPLDLAREHGNEEI

VKLLEKQ

As described in the examples that follow, the polypeptides of all aspects and embodiments of the invention were designed for their ability to self-assemble to cyclic homo-ligomers with tunable shape, size, and symmetry enables rigid display of binding domains at arbitrary orientations and distances for a range of biological applications.

In this aspect, design interfaces were grafted onto ankyrin repeat scaffolds, permitting the designed polypeptides to direct their assembly into homo-oligomeric complexes (such as dimers, trimers, tetramers, and pentamers).

The ankyrin-derived repeat polypeptides of the invention include between 2-5 repeat domains (X1-X5), depending on where the design interfaces (referred to herein as "oligomerizing positions") are located. Thus, if all of the oligomerizing positions are located in domains X1 and X2, then X3-X5 may be absent, or may be present. The repeat domains in the ankyrin-derived polypeptides are interchangeable, and thus each domain X1-X5 may be selected from modified regions of a scaffold ankyrin domain.

Oligomerizing positions for a variety of polypeptides of this aspect of the invention are shown Table 1 below, aligned with the wild-type ankyrin repeat consensus sequences.

| Position | Repeat domain designation | ank reference sequence | ank1C2_1 | ank1C4_2 | ank3C2_1 | ank4D2 |
|---|---|---|---|---|---|---|
| 1 | N-terminal Cap | S | | | | |
| 2 | N-terminal Cap | E | | E | | T |
| 3 | N-terminal Cap | L | | D | | E |
| 4 | N-terminal Cap | G | | | | |
| 5 | N-terminal Cap | K | | E | | K |
| 6 | N-terminal Cap | R | | L | | M |
| 7 | N-terminal Cap | L | | | | |
| 8 | N-terminal Cap | I | | | | |
| 9 | N-terminal Cap | E | | L | | I |
| 10 | N-terminal Cap | A | | A | | A |
| 11 | N-terminal Cap | A | | | | |
| 12 | N-terminal Cap | E | | | | R |
| 13 | N-terminal Cap | N | | L | | E |
| 14 | N-terminal Cap | G | | | | |
| 15 | N-terminal Cap | N | | I | | M |
| 16 | N-terminal Cap | K | K | A | K | I |
| 17 | N-terminal Cap | D | | E | D | I |
| 18 | N-terminal Cap | R | | A | | V |
| 19 | N-terminal Cap | V | | | | |
| 20 | N-terminal Cap | K | | R | K | I |
| 21 | N-terminal Cap | D | | M | | V |
| 22 | N-terminal Cap | L | | L | | L |
| 23 | N-terminal Cap | I/L | | | | |
| 24 | N-terminal Cap | E | | | | E |
| 25 | N-terminal Cap | N | | Q | | K |
| 26 | N-terminal Cap | G | | | | |
| 27 | N-terminal Cap | A | | | | |
| 28 | N-terminal Cap | D | | | | |
| 29 | N-terminal Cap | V/P | | | | |

-continued

| Position | Repeat domain designation | ank reference sequence | ank1C2_1 | ank1C4_2 | ank3C2_1 | ank4D2 |
|---|---|---|---|---|---|---|
| 30 | N-terminal Cap | N | | | | |
| 31 | N-terminal Cap | A | | | | |
| 32 | Internal Repeat 1 | S/K | | | | |
| 33 | Internal Repeat 1 | D | | | | |
| 34 | Internal Repeat 1 | S | | | D | |
| 35 | Internal Repeat 1 | D | | | | |
| 36 | Internal Repeat 1 | G | | | | |
| 37 | Internal Repeat 1 | K/R | | | | |
| 38 | Internal Repeat 1 | T | | | | |
| 39 | Internal Repeat 1 | P | | | | |
| 40 | Internal Repeat 1 | L | | | | |
| 41 | Internal Repeat 1 | H | | | | |
| 42 | Internal Repeat 1 | H/L/Y | | | | |
| 43 | Internal Repeat 1 | A | | | | |
| 44 | Internal Repeat 1 | A | | | | |
| 45 | Internal Repeat 1 | E | | | | |
| 46 | Internal Repeat 1 | N | | | | |
| 47 | Internal Repeat 1 | G | | | | |
| 48 | Internal Repeat 1 | H | | | | |
| 49 | Internal Repeat 1 | K | A | L | A | L |
| 50 | Internal Repeat 1 | E | E | A | K | I |
| 51 | Internal Repeat 1 | V/I | | | | |
| 52 | Internal Repeat 1 | V | | | | |
| 53 | Internal Repeat 1 | K | A | L | L | L |
| 54 | Internal Repeat 1 | L | | L | L | L |
| 55 | Internal Repeat 1 | L | | | | |
| 56 | Internal Repeat 1 | I/L | | | | |
| 57 | Internal Repeat 1 | S | E | L | E | E |
| 58 | Internal Repeat 1 | Q/K | | | | |
| 59 | Internal Repeat 1 | G | | | | |
| 60 | Internal Repeat 1 | D/A | | | | |
| 61 | Internal Repeat 1 | P/D | | | | |
| 62 | Internal Repeat 1 | V/P/N | | | | |
| 63 | Internal Repeat 1 | N/T | | | | |
| 64 | Internal Repeat 1 | A/T/S | | | | |
| 65 | Internal Repeat 2 | S/K | | | | |
| 66 | Internal Repeat 2 | D | | | | |
| 67 | Internal Repeat 2 | S | | | | |
| 68 | Internal Repeat 2 | D | | | | |
| 69 | Internal Repeat 2 | G | | | | |
| 70 | Internal Repeat 2 | K/R | | | | |
| 71 | Internal Repeat 2 | T | | | | |
| 72 | Internal Repeat 2 | P | | | | |
| 73 | Internal Repeat 2 | L | | | | |
| 74 | Internal Repeat 2 | H | | | | |
| 75 | Internal Repeat 2 | H/L/Y | | | | |
| 76 | Internal Repeat 2 | A | | | | |
| 77 | Internal Repeat 2 | A | | | | |
| 78 | Internal Repeat 2 | E | | | | |
| 79 | Internal Repeat 2 | N | | | | |
| 80 | Internal Repeat 2 | G | | | | |
| 81 | Internal Repeat 2 | H | | | | |
| 82 | Internal Repeat 2 | K | D | | A | |
| 83 | Internal Repeat 2 | E | E | T | V | |
| 84 | Internal Repeat 2 | V/I | | | | |
| 85 | Internal Repeat 2 | V | | | | |
| 86 | Internal Repeat 2 | K | L | L | A | |
| 87 | Internal Repeat 2 | L | I | L | L | |
| 88 | Internal Repeat 2 | L | | | | |
| 89 | Internal Repeat 2 | I/L | L | | K | |
| 90 | Internal Repeat 2 | S | L | L | M | |
| 91 | Internal Repeat 2 | Q/K | K | M | H | |
| 92 | Internal Repeat 2 | G | | | | |
| 93 | Internal Repeat 2 | D/A | | | | |
| 94 | Internal Repeat 2 | P/D | | | | |
| 95 | Internal Repeat 2 | V/P/N | | | | |
| 96 | Internal Repeat 2 | N/T | | | | |
| 97 | Internal Repeat 2 | A/T/S | | | | |
| 98 | Internal Repeat 3 | S/K | | | | |
| 99 | Internal Repeat 3 | D | | | | |
| 100 | Internal Repeat 3 | S | | | | |
| 101 | Internal Repeat 3 | D | | | | |
| 102 | Internal Repeat 3 | G | | | | |
| 103 | Internal Repeat 3 | K/R | | | | |
| 104 | Internal Repeat 3 | T | | | | |
| 105 | Internal Repeat 3 | P | | | | |

-continued

| Position | Repeat domain designation | ank reference sequence | ank1C2_1 | ank1C4_2 | ank3C2_1 | ank4D2 |
|---|---|---|---|---|---|---|
| 106 | Internal Repeat 3 | L | | | | |
| 107 | Internal Repeat 3 | H | | | | |
| 108 | Internal Repeat 3 | H/L/Y | | | | |
| 109 | Internal Repeat 3 | A | | | | |
| 110 | Internal Repeat 3 | A | | | | |
| 111 | Internal Repeat 3 | E | | | | |
| 112 | Internal Repeat 3 | N | | | | |
| 113 | Internal Repeat 3 | G | | | | |
| 114 | Internal Repeat 3 | H | | | | |
| 115 | Internal Repeat 3 | K | K | | | E |
| 116 | Internal Repeat 3 | E | R | | | E |
| 117 | Internal Repeat 3 | V/I | | | | |
| 118 | Internal Repeat 3 | V | | | | |
| 119 | Internal Repeat 3 | K | L | | | I |
| 120 | Internal Repeat 3 | L | V | | | L |
| 121 | Internal Repeat 3 | L | | | | |
| 122 | Internal Repeat 3 | I/L | I | | | |
| 123 | Internal Repeat 3 | S | L | | | A |
| 124 | Internal Repeat 3 | Q/K | A | K | | M |
| 125 | Internal Repeat 3 | G | | | | |
| 126 | Internal Repeat 3 | D/A | | | | |
| 127 | Internal Repeat 3 | P/D | | | | |
| 128 | Internal Repeat 3 | V/P/N | | | | |
| 129 | Internal Repeat 3 | N/T | | | | |
| 130 | Internal Repeat 3 | A/T/S | | | | |
| 131 | C-terminal Cap | S | | | | |
| 132 | C-terminal Cap | D | | | | |
| 133 | C-terminal Cap | S | | | | |
| 134 | C-terminal Cap | D | | | | |
| 135 | C-terminal Cap | G | | | | |
| 136 | C-terminal Cap | R | | | | |
| 137 | C-terminal Cap | T | | | | |
| 138 | C-terminal Cap | P | | | | |
| 139 | C-terminal Cap | L | | | | |
| 140 | C-terminal Cap | D | | | | |
| 141 | C-terminal Cap | L | | | | |
| 142 | C-terminal Cap | A | | | | |
| 143 | C-terminal Cap | R | | | | |
| 144 | C-terminal Cap | E | | | | |
| 145 | C-terminal Cap | H | | | | |
| 146 | C-terminal Cap | G | | | | |
| 147 | C-terminal Cap | N | | | | |
| 148 | C-terminal Cap | E | | | | |
| 149 | C-terminal Cap | E | E | | | E |
| 150 | C-terminal Cap | V/I | | | | |
| 151 | C-terminal Cap | V | | | | |
| 152 | C-terminal Cap | K | K | | | K |
| 153 | C-terminal Cap | L | A | | | V |
| 154 | C-terminal Cap | L | | | | |
| 155 | C-terminal Cap | E | | | | E |
| 156 | C-terminal Cap | K | K | | | D |
| 157 | C-terminal Cap | Q | Q | | | H |

Modifications to the ankyrin-repeat domain proteins (as well as the other starting scaffold repeat domains discussed herein) were all made at potential oligomerizing positions. These are the residues that drive homo-oligomerization; residues outside of these regions can be significantly modified without affecting oligomerization of the polypeptides.

In this first aspect, the recited alternative positions in X2 are modified in all designed peptides. In one further embodiment, X1 comprises the amino acid sequence at least 50% identical along its length to SEQ ID NO: 1, wherein (a) X1 possesses changes from SEQ ID NO:1 at least at one or more of residues 2, 3, 5, 6, 9, 12, 13, 15, 16, 17, 17, 20, 21, and 25, or (b) X1 possesses changes from SEQ ID NO:2 at least at one or more of residues 4, 5, 7, 8, 11, 14, 15, 17, 18, 19, 20, 22, 23, 26, and 27; or (c) X1 possesses changes from SEQ ID NO:3 at least at one or more of residues 4, 5, 7, 8, 11, 14, 15, 17, 18, 19, 20, 22, 23, 26, and 27. These are oligomerizing positions in a number of the designed peptides exemplified in Table 1.

In another embodiment, X3 is present, and wherein X3 has the amino acid sequence selected from the group consisting of (i) the amino acid sequence at least 50% identical along its length to SEQ ID NO: 1, wherein X2 possesses changes from SEQ ID NO: 1 at least at residues 20, 24, and 25;

(ii) the amino acid sequence at least 50% identical along its length to SEQ ID NO:2, wherein X2 possesses changes from SEQ ID NO:2 at least at residues 22, 26, and 27; and (iii) the amino acid sequence at least 50% identical along its length to SEQ ID NO:3, wherein X2 possesses changes from SEQ ID NO:3 at least at residues 22, 26, and 27.

In a further embodiment, X4 is present, and wherein X4 has the amino acid sequence selected from the group consisting of
(i) the amino acid sequence at least 50% identical along its length to SEQ ID NO: 1, wherein X2 possesses changes from SEQ ID NO: 1 at least at residue 25;
(ii) the amino acid sequence at least 50% identical along its length to SEQ ID NO:2, wherein X2 possesses changes from SEQ ID NO:2 at least at residue 27; and
(iii) the amino acid sequence at least 50% identical along its length to SEQ ID NO:3, wherein X2 possesses changes from SEQ ID NO:3 at least at residue 27.

In a still further embodiment, X5 is present, and wherein X5 has the amino acid sequence selected from the group consisting of
(i) the amino acid sequence at least 50% identical along its length to SEQ ID NO: 1, wherein X2 possesses changes from SEQ ID NO:1 at least at residue 23;
(ii) the amino acid sequence at least 50% identical along its length to SEQ ID NO:2, wherein X2 possesses changes from SEQ ID NO:2 at least at residue 25; and
(iii) the amino acid sequence at least 50% identical along its length to SEQ ID NO:3, wherein X2 possesses changes from SEQ ID NO:3 at least at residue 25.

In another aspect, the polypeptides are based on the ank1C2_1 scaffold (see Table 1). In this embodiment, the polypeptide comprises the general formula X1-X2-X3-X4-X5, wherein:
(a) X1 comprises the amino acid sequence that is selected from the group consisting of:
  (i) the amino acid sequence at least 50% identical along its length to SEQ ID NO:1, wherein residue 16 is K or a conservative substitution thereof;
  (ii) the amino acid sequence at least 50% identical along its length to SEQ ID NO: 2, wherein residue 18 is K or a conservative substitution thereof; and
  (iii) the amino acid sequence at least 50% identical along its length to SEQ ID NO:3, wherein residue 18 is K or a conservative substitution thereof;
(b) X2 comprises the amino acid sequence that is selected from the group consisting of:
  (i) the amino acid sequence at least 50% identical along its length to residues SEQ ID NO: 1, wherein residue 16 is A or a conservative substitution thereof, residue 17 is E or a conservative substitution thereof, residue 20 is A or a conservative substitution thereof, and residue 24 is E or a conservative substitution thereof;
  (ii) the amino acid sequence at least 50% identical along its length to residues SEQ ID NO:2, wherein residue 18 is A or a conservative substitution thereof, residue 19 is E or a conservative substitution thereof, residue 22 is A or a conservative substitution thereof, and residue 26 is E or a conservative substitution thereof; and
  (iii) the amino acid sequence at least 50% identical along its length to residues SEQ ID NO:3, wherein residue 18 is A or a conservative substitution thereof, residue 19 is E or a conservative substitution thereof, residue 22 is A or a conservative substitution thereof, and residue 26 is E or a conservative substitution thereof;
(c) X3 comprises the amino acid sequence that is selected from the group consisting of:
  (i) the amino acid sequence at least 50% identical along its length to residues SEQ ID NO: 1, wherein residue 16 is D or a conservative substitution thereof, residue 17 is E or a conservative substitution thereof, residue 20 is L or a conservative substitution thereof, residue 21 is I or a conservative substitution thereof, residue 23 is L or a conservative substitution thereof, residue 24 is L or a conservative substitution thereof, and residue 25 is K or a conservative substitution thereof;
  (ii) the amino acid sequence at least 50% identical along its length to residues SEQ ID NO:2, wherein residue 18 is D or a conservative substitution thereof, residue 19 is E or a conservative substitution thereof, residue 22 is L or a conservative substitution thereof, residue 23 is I or a conservative substitution thereof, residue 25 is L or a conservative substitution thereof, residue 26 is L or a conservative substitution thereof, and residue 27 is K or a conservative substitution thereof; and
  (iii) the amino acid sequence at least 50% identical along its length to residues SEQ ID NO:3, wherein residue 18 is D or a conservative substitution thereof, residue 19 is E or a conservative substitution thereof, residue 22 is L or a conservative substitution thereof, residue 23 is I or a conservative substitution thereof, residue 25 is L or a conservative substitution thereof, residue 26 is L or a conservative substitution thereof, and residue 27 is K or a conservative substitution thereof;
(d) X4 comprises the amino acid sequence that is selected from the group consisting of:
  (i) the amino acid sequence at least 50% identical along its length to residues SEQ ID NO: 1, wherein residue 16 is K or a conservative substitution thereof, residue 17 is R or a conservative substitution thereof, residue 20 is L or a conservative substitution thereof, residue 21 is V or a conservative substitution thereof, residue 23 is I or a conservative substitution thereof, residue 24 is L or a conservative substitution thereof, and residue 25 is A or a conservative substitution thereof;
  (ii) the amino acid sequence at least 50% identical along its length to residues SEQ ID NO:2, wherein residue 18 is K or a conservative substitution thereof, residue 19 is R or a conservative substitution thereof, residue 21 is L or a conservative substitution thereof, residue 23 is V or a conservative substitution thereof, residue 25 is I or a conservative substitution thereof, residue 26 is L or a conservative substitution thereof, and residue 27 is A or a conservative substitution thereof; and
  (iii) the amino acid sequence at least 50% identical along its length to residues SEQ ID NO:3, wherein residue 18 is K or a conservative substitution thereof, residue 19 is R or a conservative substitution thereof, residue 21 is L or a conservative substitution thereof, residue 23 is V or a conservative substitution thereof, residue 25 is I or a conservative substitution thereof, residue 26 is L or a conservative substitution thereof, and residue 27 is A or a conservative substitution thereof; and
(e) X5 comprises the amino acid sequence that is selected from the group consisting of:
  (i) the amino acid sequence at least 50% identical along its length to residues SEQ ID NO: 1, wherein residue 17 is E or a conservative substitution thereof, residue 20 is K or a conservative substitution thereof, residue 21 is A or a conservative substitution thereof, residue 24 is K or a conservative substitution thereof, and residue 25 is Q or a conservative substitution thereof;
  (ii) the amino acid sequence at least 50% identical along its length to residues SEQ ID NO:2, wherein residue 19 is E or a conservative substitution thereof, residue 21 is K or a conservative substitution thereof, residue 23 is A or a conservative substitution thereof, residue 26 is K or a conservative substitution thereof, and residue 27 is Q or a conservative substitution thereof; and (iii) the amino acid sequence at least 50% identical along its length to residues SEQ ID NO:3, wherein residue 19 is E or a conservative substitution thereof, residue 21 is K or a conservative substitution thereof, residue 23 is A or a conservative substitution thereof, residue 26 is K or a conservative substitution thereof, and residue 27 is Q or a conservative substitution thereof;

wherein the polypeptide does not comprise the amino acid sequence of SEQ ID NO: 5-7.

In one embodiment of the polypeptides based on the ank1C2_1 scaffold:

(a) X1 comprises the amino acid sequence that is selected from the group consisting of:
  (i) the amino acid sequence at least 50% identical along its length to SEQ ID NO:1, wherein residue 16 is K;
  (ii) the amino acid sequence at least 50% identical along its length to SEQ ID NO: 2, wherein residue 18 is K; and
  (iii) the amino acid sequence at least 50% identical along its length to SEQ ID NO:3, wherein residue 18 is K;

(b) X2 comprises the amino acid sequence that is selected from the group consisting of:
  (i) the amino acid sequence at least 50% identical along its length to residues SEQ ID NO:1, wherein residue 16 is A, residue 17 is E, residue 20 is A, and residue 24 is E;
  (ii) the amino acid sequence at least 50% identical along its length to residues SEQ ID NO:2, wherein residue 18 is A, residue 19 is E, residue 22 is A, and residue 26 is E; and
  (iii) the amino acid sequence at least 50% identical along its length to residues SEQ ID NO:3, wherein residue 18 is A, residue 19 is E, residue 22 is A, and residue 26 is E;

(c) X3 comprises the amino acid sequence that is selected from the group consisting of:
  (i) the amino acid sequence at least 50% identical along its length to residues SEQ ID NO:1, wherein residue 16 is D, residue 17 is E, residue 20 is L, residue 21 is I, residue 23 is L, residue 24 is L, and residue 25 is K;
  (ii) the amino acid sequence at least 50% identical along its length to residues SEQ ID NO:2, wherein residue 18 is D, residue 19 is E, residue 22 is L, residue 23 is I, residue 25 is L, residue 26 is L, and residue 27 is K; and
  (iii) the amino acid sequence at least 50% identical along its length to residues SEQ ID NO:3, wherein residue 18 is D, residue 19 is E, residue 22 is L, residue 23 is I, residue 25 is L, residue 26 is L, and residue 27 is K;

(d) X4 comprises the amino acid sequence that is selected from the group consisting of:
  (i) the amino acid sequence at least 50% identical along its length to residues SEQ ID NO: 1, wherein residue 16 is K, residue 17 is R, residue 20 is L, residue 21 is V, residue 23 is I, residue 24 is L, and residue 25 is A;
  (ii) the amino acid sequence at least 50% identical along its length to residues SEQ ID NO:2, wherein residue 18 is K, residue 19 is R, residue 21 is L, residue 23 is V, residue 25 is I, residue 26 is L, and residue 27 is A; and
  (iii) the amino acid sequence at least 50% identical along its length to residues SEQ ID NO:3, wherein residue 18 is K, residue 19 is R, residue 21 is L, residue 23 is V, residue 25 is I, residue 26 is L, and residue 27 is A; and (e) X5 comprises the amino acid sequence that is selected from the group consisting of:
  (i) the amino acid sequence at least 50% identical along its length to residues SEQ ID NO: 1, wherein residue 17 is E, residue 20 is K, residue 21 is A, residue 24 is K, and residue 25 is Q;
  (ii) the amino acid sequence at least 50% identical along its length to residues SEQ ID NO:2, wherein residue 19 is E, residue 21 is K, residue 23 is A, residue 26 is K, and residue 27 is Q; and
  (iii) the amino acid sequence at least 50% identical along its length to residues SEQ ID NO:3, wherein residue 19 is E, residue 21 is K, residue 23 is A, residue 26 is K, and residue 27 is Q.

In another aspect, the polypeptides are based on the ank1C4_2 scaffold (see Table 1). In this embodiment, the polypeptide comprises the general formula X1-X2-X3-X4-X5, wherein:

(a) X1 comprises the amino acid sequence that is selected from the group consisting of:
  (i) the amino acid sequence at least 50% identical along its length to SEQ ID NO: 1, wherein residue 2 is E or a conservative substitution thereof, residue 3 is D or a conservative substitution thereof, residue 5 is E or a conservative substitution thereof, residue 6 is L or a conservative substitution thereof, residue 9 is L or a conservative substitution thereof, residue 10 is A or a conservative substitution thereof, residue 13 is L or a conservative substitution thereof. residue 15 is I or a conservative substitution thereof. residue 16 is A or a conservative substitution thereof, residue 17 is E or a conservative substitution thereof, residue 18 is A or a conservative substitution thereof, residue 20 is R or a conservative substitution thereof, residue 21 is M or a conservative substitution thereof, residue 22 is L or a conservative substitution thereof, and residue 25 is Q or a conservative substitution thereof;
  (ii) the amino acid sequence at least 50% identical along its length to SEQ ID NO: 2, wherein residue 4 is E or a conservative substitution thereof, residue 5 is D or a conservative substitution thereof, residue 7 is E or a conservative substitution thereof, residue 8 is L or a conservative substitution thereof, residue 11 is L or a conservative substitution thereof, residue 12 is A or a conservative substitution thereof, residue 15 is L or a conservative substitution thereof. residue 17 is I or a conservative substitution thereof. residue 18 is A or a conservative substitution thereof, residue 19 is E or a conservative substitution thereof, residue 20 is A or a conservative substitution thereof, residue 22 is R or a conservative substitution thereof, residue 23 is M or a conservative substitution thereof, residue 24 is L or a conservative substitution thereof, and residue 27 is Q or a conservative substitution thereof; and
  (iii) the amino acid sequence at least 50% identical along its length to SEQ ID NO:3, wherein residue 4 is E or a conservative substitution thereof, residue 5 is D or a conservative substitution thereof, residue 7 is E or a conservative substitution thereof, residue 8 is L or a conservative substitution thereof, residue 11 is L or a conservative substitution thereof, residue 12 is A or a conservative substitution thereof, residue 15 is L or a conservative substitution thereof. residue 17 is I or a conservative substitution thereof. residue 18 is A or a conservative substitution thereof, residue 19 is E or a conservative substitution thereof, residue 20 is A or a conservative substitution thereof, residue 22 is R or a conservative substitution thereof, residue 23 is M or a conservative substitution thereof, residue 24 is L or a conservative substitution thereof, and residue 27 is Q or a conservative substitution thereof;

(b) X2 comprises the amino acid sequence that is selected from the group consisting of:
  (i) the amino acid sequence at least 50% identical along its length to residues SEQ ID NO: 1, wherein residue 16 is L or a conservative substitution thereof, residue 17 is A or a conservative substitution thereof, residue 20 is L or a conservative substitution thereof, residue 21 is L or a conservative substitution thereof, and residue 24 is L or a conservative substitution thereof;
  (ii) the amino acid sequence at least 50% identical along its length to residues SEQ ID NO:2, wherein residue 18 is L or a conservative substitution thereof, residue 19 is A or a conservative substitution thereof, residue 22 is L or a conservative substitution thereof, residue 23 is L or a conservative substitution thereof, and residue 26 is L or a conservative substitution thereof; and
  (iii) the amino acid sequence at least 50% identical along its length to residues SEQ ID NO:3, wherein residue 18 is L or a conservative substitution thereof, residue 19 is A or a conservative substitution thereof, residue 22 is L or a conservative substitution thereof, residue 23 is L or a conservative substitution thereof, and residue 26 is L or a conservative substitution thereof;

(c) X3 comprises the amino acid sequence that is selected from the group consisting of:
  (i) the amino acid sequence at least 50% identical along its length to residues SEQ ID NO: 1, wherein residue 17 is T or a conservative substitution thereof, residue 20 is L or a conservative substitution thereof, residue 21 is L or a conservative substitution thereof, residue 24 is L or a conservative substitution thereof, and residue 25 is M or a conservative substitution thereof;
  (ii) the amino acid sequence at least 50% identical along its length to residues SEQ ID NO:2, wherein residue 19 is T or a conservative substitution thereof, residue 21 is L or a conservative substitution thereof, residue 23 is L or a conservative substitution thereof, residue 26 is L or a conservative substitution thereof, and residue 27 is M or a conservative substitution thereof; and
  (iii) the amino acid sequence at least 50% identical along its length to residues SEQ ID NO:3, wherein residue 19 is T or a conservative substitution thereof, residue 21 is L or a conservative substitution thereof, residue 23 is L or a conservative substitution thereof, residue 26 is L or a conservative substitution thereof, and residue 27 is M or a conservative substitution thereof;

(d) X4 comprises the amino acid sequence that is selected from the group consisting of:
  (i) the amino acid sequence at least 50% identical along its length to residues SEQ ID NO: 1, wherein residue 25 is K or a conservative substitution thereof;
  (ii) the amino acid sequence at least 50% identical along its length to residues SEQ ID NO:2, wherein residue 27 is K or a conservative substitution thereof; and
  (iii) the amino acid sequence at least 50% identical along its length to residues SEQ ID NO:3, wherein residue 27 or a conservative substitution thereof; and (e) X5 is absent, or comprises the amino acid sequence that is selected from the group consisting of:
  (i) the amino acid sequence at least 50% identical along its length to residues SEQ ID NO: 1;
  (ii) the amino acid sequence at least 50% identical along its length to residues SEQ ID NO:2; and
  (iii) the amino acid sequence at least 50% identical along its length to residues SEQ ID NO:3;

wherein the polypeptide does not comprise the amino acid sequence of SEQ ID NOs: 5-7.

In one embodiment of the polypeptides based on the ank1C4_2 scaffold:

(a) X1 comprises the amino acid sequence that is selected from the group consisting of:
  (i) the amino acid sequence at least 50% identical along its length to SEQ ID NO:1, wherein residue 2 is E, residue 3 is D, residue 5 is E, residue 6 is L, residue 9 is L, residue 10 is A, residue 13 is L. residue 15 is I, residue 16 is A, residue 17 is E, residue 18 is A, residue 20 is R, residue 21 is M, residue 22 is L, and residue 25 is Q;
  (ii) the amino acid sequence at least 50% identical along its length to SEQ ID NO: 2, wherein residue 4 is E, residue 5 is D, residue 7 is E, residue 8 is L, residue 11 is L, residue 12 is A, residue 15 is L. residue 17 is I, residue 18 is A, residue 19 is E, residue 20 is A, residue 22 is R, residue 23 is M, residue 24 is L, and residue 27 is Q; and
  (iii) the amino acid sequence at least 50% identical along its length to SEQ ID NO:3, wherein residue 4 is E, residue 5 is D, residue 7 is E, residue 8 is L, residue 11 is L, residue 12 is A, residue 15 is L. residue 17 is I, residue 18 is A, residue 19 is E, residue 20 is A, residue 22 is R, residue 23 is M, residue 24 is L, and residue 27 is Q;

(b) X2 comprises the amino acid sequence that is selected from the group consisting of:
  (i) the amino acid sequence at least 50% identical along its length to residues SEQ ID NO:1, wherein residue 16 is L, residue 17 is A, residue 20 is L, residue 21 is L, and residue 24 is L;
  (ii) the amino acid sequence at least 50% identical along its length to residues SEQ ID NO:2, wherein residue 18 is L, residue 19 is A, residue 22 is L, residue 23 is L, and residue 26 is L; and
  (iii) the amino acid sequence at least 50% identical along its length to residues SEQ ID NO:3, wherein residue 18 is L, residue 19 is A, residue 22 is L, residue 23 is L, and residue 26 is L;

(c) X3 comprises the amino acid sequence that is selected from the group consisting of:
  (i) the amino acid sequence at least 50% identical along its length to residues SEQ ID NO: 1, wherein residue 17 is T, residue 20 is L, residue 21 is L, residue 24 is L, and residue 25 is M;
  (ii) the amino acid sequence at least 50% identical along its length to residues SEQ ID NO:2, wherein residue 19 is T, residue 21 is L, residue 23 is L, residue 26 is L, and residue 27 is M; and
  (iii) the amino acid sequence at least 50% identical along its length to residues SEQ ID NO:3, wherein residue 19 is T, residue 21 is L, residue 23 is L, residue 26 is L, and residue 27 is M;

(d) X4 comprises the amino acid sequence that is selected from the group consisting of:
  (i) the amino acid sequence at least 50% identical along its length to residues SEQ ID NO: 1, wherein residue 25 is K;
  (ii) the amino acid sequence at least 50% identical along its length to residues SEQ ID NO:2, wherein residue 27 is K; and (iii) the amino acid sequence at least 50% identical along its length to residues SEQ ID NO:3, wherein residue 27; and
(e) X5 is absent, or comprises the amino acid sequence that is selected from the group consisting of:
  (i) the amino acid sequence at least 50% identical along its length to residues SEQ ID NO: 1;
  (ii) the amino acid sequence at least 50% identical along its length to residues SEQ ID NO:2; and
  (iii) the amino acid sequence at least 50% identical along its length to residues SEQ ID NO:3;
wherein the polypeptide does not comprise the amino acid sequence of SEQ ID NOs: 5-7.

In another aspect, the polypeptides are based on the ank3C2_1 scaffold (see Table 1). In this embodiment, the polypeptide comprises the general formula X1-X2-X3-X4-X5, wherein:
(a) X1 comprises the amino acid sequence that is selected from the group consisting of:
  (i) the amino acid sequence at least 50% identical along its length to SEQ ID NO:1, wherein residue 16 is K or a conservative substitution thereof, residue 17 is D or a conservative substitution thereof, and residue 20 is K or a conservative substitution thereof;
  (ii) the amino acid sequence at least 50% identical along its length to SEQ ID NO: 2, wherein residue 18 is K or a conservative substitution thereof, residue 19 is D or a conservative substitution thereof, and residue 22 is K or a conservative substitution thereof; and
  (iii) the amino acid sequence at least 50% identical along its length to SEQ ID NO:3, wherein residue 18 is K or a conservative substitution thereof, residue 19 is D or a conservative substitution thereof, and residue 22 is K or a conservative substitution thereof;
(b) X2 comprises the amino acid sequence that is selected from the group consisting of:
  (i) the amino acid sequence at least 50% identical along its length to residues SEQ ID NO: 1, wherein residue 16 is A or a conservative substitution thereof, residue 17 is K or a conservative substitution thereof, residue 20 is L or a conservative substitution thereof, residue 21 is L or a conservative substitution thereof, and residue 24 is E or a conservative substitution thereof;
  (ii) the amino acid sequence at least 50% identical along its length to residues SEQ ID NO:2, wherein residue 18 is A or a conservative substitution thereof, residue 19 is K or a conservative substitution thereof, residue 22 is L or a conservative substitution thereof, residue 23 is L or a conservative substitution thereof, and residue 26 is E or a conservative substitution thereof; and
  (iii) the amino acid sequence at least 50% identical along its length to residues SEQ ID NO:3, wherein residue 18 is A or a conservative substitution thereof, residue 19 is K or a conservative substitution thereof, residue 22 is L or a conservative substitution thereof, residue 23 is L or a conservative substitution thereof, and residue 26 is E or a conservative substitution thereof;
(c) X3 comprises the amino acid sequence that is selected from the group consisting of:
  (i) the amino acid sequence at least 50% identical along its length to residues SEQ ID NO: 1, wherein residue 16 is A or a conservative substitution thereof; 17 is V or a conservative substitution thereof, residue 20 is A or a conservative substitution thereof, residue 21 is L or a conservative substitution thereof, residue 23 is L or a conservative substitution thereof, residue 24 is M or a conservative substitution thereof, and residue 25 is H or a conservative substitution thereof;
  (ii) the amino acid sequence at least 50% identical along its length to residues SEQ ID NO:2, wherein residue 18 is A or a conservative substitution thereof; 19 is V or a conservative substitution thereof, residue 22 is A or a conservative substitution thereof, residue 23 is L or a conservative substitution thereof, residue 25 is L or a conservative substitution thereof, residue 26 is M or a conservative substitution thereof, and residue 27 is H or a conservative substitution thereof; and
  (iii) the amino acid sequence at least 50% identical along its length to residues SEQ ID NO:3, wherein residue 18 is A or a conservative substitution thereof; 19 is V or a conservative substitution thereof, residue 22 is A or a conservative substitution thereof, residue 23 is L or a conservative substitution thereof, residue 25 is L or a conservative substitution thereof, residue 26 is M or a conservative substitution thereof, and residue 27 is H or a conservative substitution thereof;
(d) X4 comprises the amino acid sequence that is selected from the group consisting of:
  (i) the amino acid sequence at least 50% identical along its length to residues SEQ ID NO: 1, wherein residue 16 is E or a conservative substitution thereof, residue 17 is E or a conservative substitution thereof, residue 20 is I or a conservative substitution thereof, residue 21 is L or a conservative substitution thereof, residue 24 is A or a conservative substitution thereof, and residue 25 is M or a conservative substitution thereof;
  (ii) the amino acid sequence at least 50% identical along its length to residues SEQ ID NO:2, wherein residue 18 is E or a conservative substitution thereof, residue 19 is E or a conservative substitution thereof, residue 22 is I or a conservative substitution thereof, residue 23 is L or a conservative substitution thereof, residue 26 is A or a conservative substitution thereof, and residue 27 is M or a conservative substitution thereof; and
  (iii) the amino acid sequence at least 50% identical along its length to residues SEQ ID NO:3, wherein residue 18 is E or a conservative substitution thereof, residue 19 is E or a conservative substitution thereof, residue 22 is I or a conservative substitution thereof, residue 23 is L or a conservative substitution thereof, residue 26 is A or a conservative substitution thereof, and residue 27 is M or a conservative substitution thereof; and
(e) X5 comprises the amino acid sequence that is selected from the group consisting of:
  (i) the amino acid sequence at least 50% identical along its length to residues SEQ ID NO: 1, wherein residue 17 is E or a conservative substitution thereof, residue 20 is K or a conservative substitution thereof, residue 21 is V or a conservative substitution thereof, residue 23 is E or a conservative substitution thereof, residue 24 is D or a conservative substitution thereof, and residue 25 is H or a conservative substitution thereof;
  (ii) the amino acid sequence at least 50% identical along its length to residues SEQ ID NO:2, wherein residue 19 is E or a conservative substitution thereof, residue 22 is K or a conservative substitution thereof, residue 23 is V or a conservative substitution thereof, residue 25 is E or a conservative substitution thereof, residue 26 is D or a conservative substitution thereof, and residue 27 is H or a conservative substitution thereof; and
  (iii) the amino acid sequence at least 50% identical along its length to residues SEQ ID NO:3, wherein residue 19 is E or a conservative substitution thereof, residue 22 is K or a conservative substitution thereof, residue 23 is V or a conservative substitution thereof, residue 25 is E or a conservative substitution thereof, residue 26 is D or a conservative substitution thereof, and residue 27 is H or a conservative substitution thereof;

wherein the polypeptide does not comprise the amino acid sequence of SEQ ID NOs: 5-7.

In one embodiment of the polypeptides based on the ank3C2_1 scaffold (a) X1 comprises the amino acid sequence that is selected from the group consisting of:
   (i) the amino acid sequence at least 50% identical along its length to SEQ ID NO:1, wherein residue 16 is K, residue 17 is D, and residue 20 is K;
   (ii) the amino acid sequence at least 50% identical along its length to SEQ ID NO: 2, wherein residue 18 is K, residue 19 is D, and residue 22 is K; and
   (iii) the amino acid sequence at least 50% identical along its length to SEQ ID NO:3, wherein residue 18 is K, residue 19 is D, and residue 22 is K;

(b) X2 comprises the amino acid sequence that is selected from the group consisting of:
   (i) the amino acid sequence at least 50% identical along its length to residues SEQ ID NO: 1, wherein residue 16 is A, residue 17 is K, residue 20 is L, residue 21 is L, and residue 24 is E;
   (ii) the amino acid sequence at least 50% identical along its length to residues SEQ ID NO:2, wherein residue 18 is A, residue 19 is K, residue 22 is L, residue 23 is L, and residue 26 is E; and
   (iii) the amino acid sequence at least 50% identical along its length to residues SEQ ID NO:3, wherein residue 18 is A, residue 19 is K, residue 22 is L, residue 23 is L, and residue 26 is E;

(c) X3 comprises the amino acid sequence that is selected from the group consisting of:
   (i) the amino acid sequence at least 50% identical along its length to residues SEQ ID NO:1, wherein residue 16 is A; 17 is V, residue 20 is A, residue 21 is L, residue 23 is L, residue 24 is M, and residue 25 is H;
   (ii) the amino acid sequence at least 50% identical along its length to residues SEQ ID NO:2, wherein residue 18 is A; 19 is V, residue 22 is A, residue 23 is L, residue 25 is L, residue 26 is M, and residue 27 is H; and
   (iii) the amino acid sequence at least 50% identical along its length to residues SEQ ID NO:3, wherein residue 18 is A; 19 is V, residue 22 is A, residue 23 is L, residue 25 is L, residue 26 is M, and residue 27 is H;

(d) X4 comprises the amino acid sequence that is selected from the group consisting of:
   (i) the amino acid sequence at least 50% identical along its length to residues SEQ ID NO: 1, wherein residue 16 is E, residue 17 is E, residue 20 is I, residue 21 is L, residue 24 is A, and residue 25 is M;
   (ii) the amino acid sequence at least 50% identical along its length to residues SEQ ID NO:2, wherein residue 18 is E, residue 19 is E, residue 22 is I, residue 23 is L, residue 26 is A, and residue 27 is M; and
   (iii) the amino acid sequence at least 50% identical along its length to residues SEQ ID NO:3, wherein residue 18 is E, residue 19 is E, residue 22 is I, residue 23 is L, residue 26 is A, and residue 27 is M; and (e) X5 comprises the amino acid sequence that is selected from the group consisting of:
   (i) the amino acid sequence at least 50% identical along its length to residues SEQ ID NO: 1, wherein residue 17 is E, residue 20 is K, residue 21 is V, residue 23 is E, residue 24 is D, and residue 25 is H;
   (ii) the amino acid sequence at least 50% identical along its length to residues SEQ ID NO:2, wherein residue 19 is E, residue 22 is K, residue 23 is V, residue 25 is E, residue 26 is D, and residue 27 is H; and
   (iii) the amino acid sequence at least 50% identical along its length to residues SEQ ID NO:3, wherein residue 19 is E, residue 22 is K, residue 23 is V, residue 25 is E, residue 26 is D, and residue 27 is H;

In another aspect, the polypeptides are based on the ank4D2 scaffold (see Table 1). In this embodiment, the polypeptide comprises the general formula X1-X2-X3-X4-X5, wherein:

(a) X1 comprises the amino acid sequence that is selected from the group consisting of:
   (i) the amino acid sequence at least 50% identical along its length to SEQ ID NO:1, wherein residue 2 is T or a conservative substitution thereof, residue 3 is E or a conservative substitution thereof, residue 5 is K or a conservative substitution thereof, residue 6 is M or a conservative substitution thereof, residue 9 is I or a conservative substitution thereof, residue 10 is A or a conservative substitution thereof, residue 12 is R or a conservative substitution thereof, residue 13 is E or a conservative substitution thereof. residue 15 is M or a conservative substitution thereof. residue 16 is I or a conservative substitution thereof, residue 17 is I or a conservative substitution thereof, residue 18 is V or a conservative substitution thereof, residue 20 is R or a conservative substitution thereof, residue 21 is M or a conservative substitution thereof, residue 22 is L or a conservative substitution thereof, residue 24 is E or a conservative substitution thereof, and residue 25 is K or a conservative substitution thereof;
   (ii) the amino acid sequence at least 50% identical along its length to SEQ ID NO: 2, wherein residue 4 is T or a conservative substitution thereof, residue 5 is E or a conservative substitution thereof, residue 7 is K or a conservative substitution thereof, residue 8 is M or a conservative substitution thereof, residue 10 is I or a conservative substitution thereof, residue 12 is A or a conservative substitution thereof, residue 14 is R or a conservative substitution thereof, residue 15 is E or a conservative substitution thereof. residue 17 is M or a conservative substitution thereof. residue 18 is I or a conservative substitution thereof, residue 19 is I or a conservative substitution thereof, residue 20 is V or a conservative substitution thereof, residue 22 is R or a conservative substitution thereof, residue 23 is M or a conservative substitution thereof, residue 24 is L or a conservative substitution thereof, residue 26 is E or a conservative substitution thereof, and residue 27 is K or a conservative substitution thereof; and
   (iii) the amino acid sequence at least 50% identical along its length to SEQ ID NO:3, wherein residue 4 is T or a conservative substitution thereof, residue 5 is E or a conservative substitution thereof, residue 7 is K or a conservative substitution thereof, residue 8 is M or a conservative substitution thereof, residue 10 is I or a conservative substitution thereof, residue 12 is A or a conservative substitution thereof, residue 14 is R or a conservative substitution thereof, residue 15 is E or a conservative substitution thereof. residue 17 is M or a conservative substitution thereof. residue 18 is I or a conservative substitution thereof, residue 19 is I or a conservative substitution thereof, residue 20 is V or a conservative substitution thereof, residue 22 is R or a conservative substitution thereof, residue 23 is M or a conservative substitution thereof, residue 24 is L or a conservative substitution thereof, residue 26 is E or a conservative substitution thereof, and residue 27 is K or a conservative substitution thereof;

(b) X2 comprises the amino acid sequence that is selected from the group consisting of:
  (i) the amino acid sequence at least 50% identical along its length to residues SEQ ID NO: 1, wherein residue 16 is L or a conservative substitution thereof, residue 17 is I or a conservative substitution thereof, residue 20 is L or a conservative substitution thereof, residue 21 is L or a conservative substitution thereof, and residue 24 is E or a conservative substitution thereof;
  (ii) the amino acid sequence at least 50% identical along its length to residues SEQ ID NO:2, wherein residue 18 is L or a conservative substitution thereof, residue 19 is I or a conservative substitution thereof, residue 22 is L or a conservative substitution thereof, residue 23 is L or a conservative substitution thereof, and residue 26 is E or a conservative substitution thereof; and
  (iii) the amino acid sequence at least 50% identical along its length to residues SEQ ID NO:3, wherein residue 18 is L or a conservative substitution thereof, residue 19 is I or a conservative substitution thereof, residue 22 is L or a conservative substitution thereof, residue 23 is L or a conservative substitution thereof, and residue 26 is E or a conservative substitution thereof;

(c) X3 is absent or comprises the amino acid sequence that is selected from the group consisting of:
  (i) the amino acid sequence at least 50% identical along its length to residues SEQ ID NO: 1;
  (ii) the amino acid sequence at least 50% identical along its length to residues SEQ ID NO:2; and
  (iii) the amino acid sequence at least 50% identical along its length to residues SEQ ID NO:3;

(d) X4 is absent or comprises the amino acid sequence that is selected from the group consisting of:
  (i) the amino acid sequence at least 50% identical along its length to residues SEQ ID NO:1;
  (ii) the amino acid sequence at least 50% identical along its length to residues SEQ ID NO:2; and
  (iii) the amino acid sequence at least 50% identical along its length to residues SEQ ID NO:3; and (e) X5 is absent, or comprises the amino acid sequence that is selected from the group consisting of:
  (i) the amino acid sequence at least 50% identical along its length to residues SEQ ID NO: 1;
  (ii) the amino acid sequence at least 50% identical along its length to residues SEQ ID NO:2; and
  (iii) the amino acid sequence at least 50% identical along its length to residues SEQ ID NO:3;

wherein the polypeptide does not comprise the amino acid sequence of SEQ ID NOs: 5-7.

In one embodiment of the polypeptides based on the ank4D2 scaffold:

(a) X1 comprises the amino acid sequence that is selected from the group consisting of:
  (i) the amino acid sequence at least 50% identical along its length to SEQ ID NO:1, wherein residue 2 is T, residue 3 is E, residue 5 is K, residue 6 is M, residue 9 is I, residue 10 is A, residue 12 is R, residue 13 is E. residue 15 is M. residue 16 is I, residue 17 is I, residue 18 is V, residue 20 is R, residue 21 is M, residue 22 is L, residue 24 is E, and residue 25 is K;
  (ii) the amino acid sequence at least 50% identical along its length to SEQ ID NO: 2, wherein residue 4 is T, residue 5 is E, residue 7 is K, residue 8 is M, residue 10 is I, residue 12 is A, residue 14 is R, residue 15 is E. residue 17 is M. residue 18 is I, residue 19 is I, residue 20 is V, residue 22 is R, residue 23 is M, residue 24 is L, residue 26 is E, and residue 27 is K; and
  (iii) the amino acid sequence at least 50% identical along its length to SEQ ID NO:3, wherein residue 4 is T, residue 5 is E, residue 7 is K, residue 8 is M, residue 10 is I, residue 12 is A, residue 14 is R, residue 15 is E. residue 17 is M. residue 18 is I, residue 19 is I, residue 20 is V, residue 22 is R, residue 23 is M, residue 24 is L, residue 26 is E, and residue 27 is K; and (b) X2 comprises the amino acid sequence that is selected from the group consisting of:
  (i) the amino acid sequence at least 50% identical along its length to residues SEQ ID NO:1, wherein residue 16 is L, residue 17 is I, residue 20 is L, residue 21 is L, and residue 24 is E;
  (ii) the amino acid sequence at least 50% identical along its length to residues SEQ ID NO:2, wherein residue 18 is L, residue 19 is I, residue 22 is L, residue 23 is L, and residue 26 is E; and
  (iii) the amino acid sequence at least 50% identical along its length to residues SEQ ID NO:3, wherein residue 18 is L, residue 19 is I, residue 22 is L, residue 23 is L, and residue 26 is E.

In one embodiment of all of the various ankyrin-derived polypeptides of the invention, all oligomerizing positions in the amino acid sequence selected from the group consisting of SEQ ID NO: 12-15 have the amino acid residue shown in the amino acid sequence selected from the group consisting of SEQ ID NO: 12-15 or conservative substitutions thereof.

In another aspect, the invention provides isolated polypeptides comprising the general formula X1-X2-X3-X4, wherein:

X1 is at least 50% identical along its length to residues 1-34 of the amino acid sequence of SEQ ID NO: 8, wherein the amino acid sequence of X1 differs from the amino acid sequence of residues 1-34 of SEQ ID NO: 8 at least at residues 6, 8, 13, 21, 25, and 28;

X2 is absent, or is at least 50% identical along its length to residues 36-68 of the amino acid sequence of SEQ ID NO: 8;

X3 is absent, or is at least 50% identical along its length to residues 69-102 of the amino acid sequence of SEQ ID NO: 8; and X4 is absent, or is at least 50% identical along its length to residues 103-119 of the amino acid sequence of SEQ ID NO: 8;

wherein the polypeptide is not identical to SEQ ID NO:8 or SEQ ID NO:41 (the tpr reference sequence).

```
SEQ ID NO: 8: >1na0
NSAEAWYNLGNAYYKQGDYDEAIEYYQKALELDPNNAEAWYNLG-
NAYYKQGDY
DEAIEYYQKALELDPNNAEAWYNLGNAYYKQGDYDEAIEYYQKALELDPN-
NAE
AKQNLGNAKQKQG
```

In this aspect, design interfaces were grafted onto 1na0 or tpr repeat scaffolds which are examples of tetratricopeptide repeat proteins, permitting the designed polypeptides to direct their assembly into homo-oligomeric complexes (such as dimers, trimers, tetramers, and pentamers).

Figure 4B:
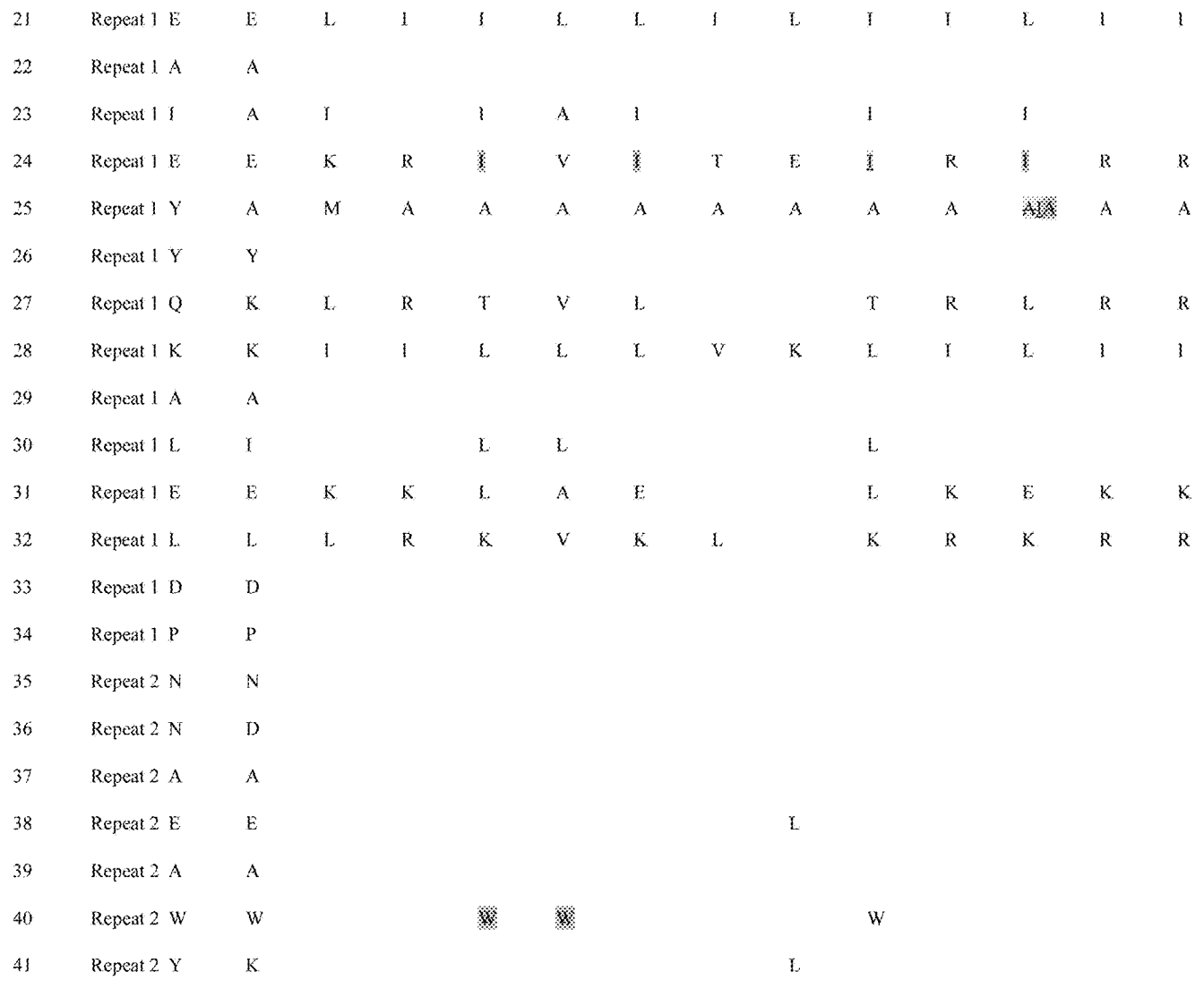
Figure 4C:
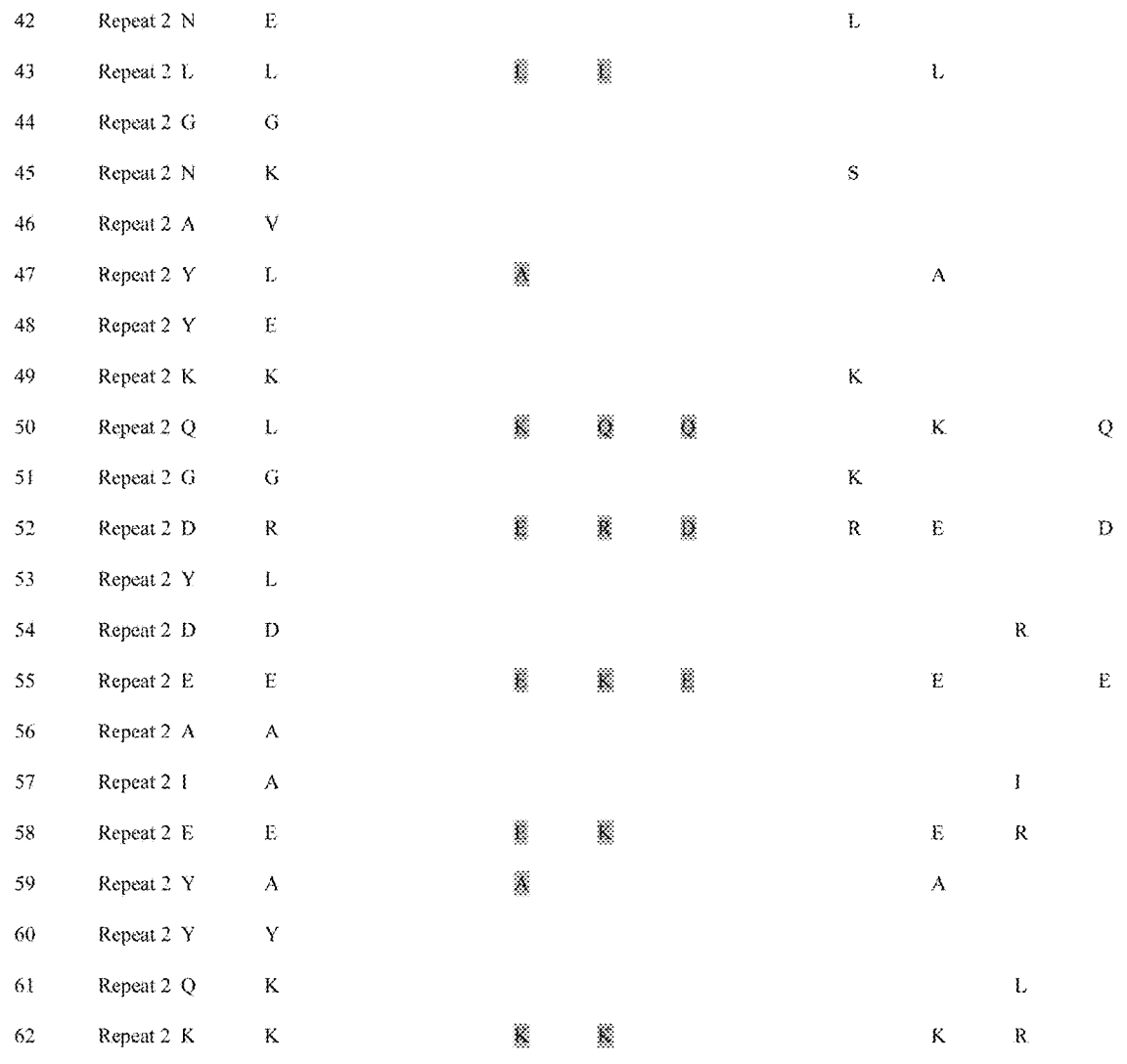
Figure 4E:
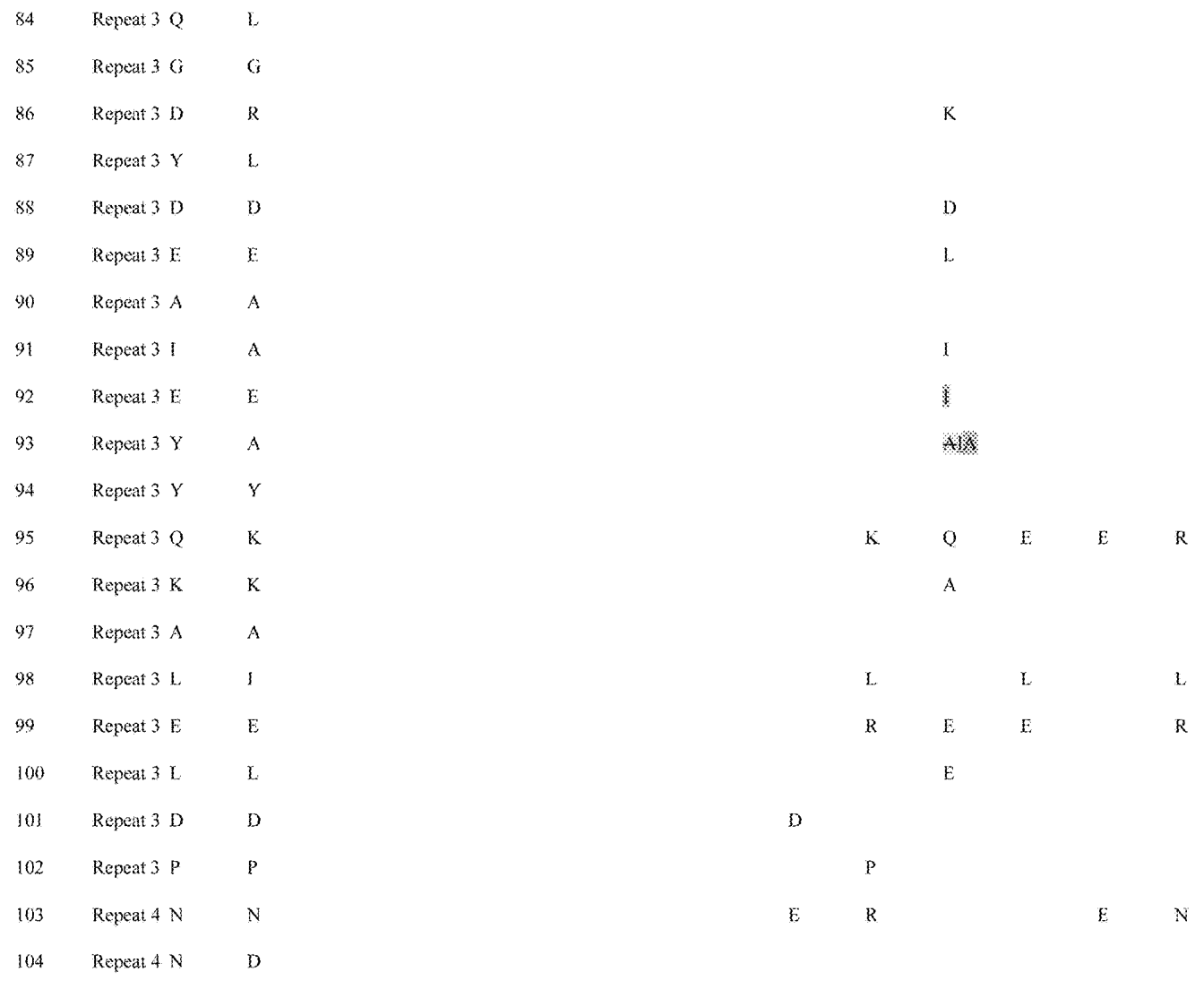

Oligomerizing positions for a variety of polypeptides of this aspect of the invention are shown FIG. 4, aligned with the wild-type reference sequences. These are the residues that drive homo-oligomerization of the polypeptides of this aspect; residues outside of these regions can be significantly modified without affecting oligomerization of the polypeptides.

In one embodiment, the amino acid sequence of X1 differs from the amino acid sequence of residues 1-34 of SEQ ID NO: 8 at least as follows:

W6 is substituted with A, M or conservative substitutions thereof;

N8 is substituted with I, L, K, D or conservative substitutions thereof;

Y13 is substituted with I, A, M or conservative substitutions thereof;

E21 is substituted with I, L or conservative substitutions thereof;

Y25 is substituted with M, A or conservative substitutions thereof; and

K28 is substituted with I, L, V or conservative substitutions thereof.

In another embodiment, the amino acid sequence of X1 further differs from the amino acid sequence of residues 1-34 of SEQ ID NO: 8 at least at residues 2, 5, 18, and 27.

In a further embodiment, the amino acid sequence of X1 differs from the amino acid sequence of residues 1-34 of SEQ ID NO: 8 at least as follows:

S2 is substituted with R, E, L or conservative substitutions thereof;

A5 is substituted with M, L, K, V or conservative substitutions thereof;

D18 is substituted with L, E, Q or conservative substitutions thereof; and

Q27 is substituted with L, R, T, V or conservative substitutions thereof.

In a further embodiment, X1 is at least 50% identical to residues 1-34 of the amino acid sequence of one of SEQ ID NOs:16-21. In another embodiment, all oligomerizing positions in residues 1-34 of the amino acid sequence selected from the group consisting of SEQ ID NOs: 16-21 have the amino acid residue shown in the amino acid sequence selected from the group consisting of SEQ ID NOs: 16-21 or conservative substitutions thereof.

In one embodiment, X2 is present; in one non-limiting embodiment, the amino acid sequence of X2 differs from the amino acid sequence of residues 35-68 of SEQ ID NO: 8 at one or more of residues 47, 50, 55, 58, and 59. In another embodiment, X2, X3, and X4 are present. In one such embodiment, the amino acid sequence of X3 differs from the amino acid sequence of residues 69-102 of SEQ ID NO: 8 at least at residue 95. In another embodiment, residue Q95 is substituted with K, E, R, or conservative substitutions thereof.

In another embodiment, the amino acid sequence of X4 differs from the amino acid sequence of residues 103-119 of SEQ ID NO: 8 at least at residues 108, 112, and 116. In one such embodiment, residue K108 is substituted with I, L, M, or conservative substitutions thereof; residue G112 is substituted with I, L or conservative substitutions thereof; and residue Q116 is substituted with E, A, D, M or conservative substitutions thereof.

In another aspect is provided polypeptides comprising the amino acid sequence at least 50% identical to the amino acid sequence of SEQ ID NO: 10, wherein all oligomerizing positions in SEQ ID NO: −10 have the amino acid residue shown in SEQ ID NO: 10 or conservative substitutions thereof, and wherein the polypeptide does not comprise acid sequence of SEQ ID NO: 9.

>tpr1C4_2 (tpr1C4_pm3 )
(SEQ ID NO: 10)
ASSWVMLGLLLSLLNRLSLAAEAYKKAIELDPNDALAWLLLGSVLE-
KLKRLD
EAAEAYKKAIELKPNDASAWKELGKVLEKLGRLDEAAEAYKKAIELD-
PEDAE
AWKELGKVLEKLGRLDEAAEAYKKAIELDPND >tpr1
(SEQ ID NO: 9)
AEAWKELGKVLEKLGRLDEAAEAYKKAIELDPNDAEAWKELGKVLEKL-
GRLD
EAAEAYKKAIELDPNDAEAWKELGKVLEKLGRLDEAAEAYKKAIELDPN-
DAE
AWKELGKVLEKLGRLDEAAEAYKKAIELDPND In another aspect are provided polypeptides comprising the amino acid sequence at least 50% identical to SEQ ID NO: 11, wherein the polypeptide amino acid sequence differs from SEQ ID NO: 11 at least at residues 7, 8, 10, 14, 17, 118, 122, 146, 149, and 150.

>3ltj
(SEQ ID NO: 11)
TDPEKVEMYIKNLQDDSYYVRRAAAYALGKIGDERAVEPLIKA-
LKDEDAWVR

RAAADALGQIGDERAVEPLIKALKDEDGWVRQSAAVALGQIGDERAVEP-
LIK

ALKDEDWFVRIAAAFALGEIGDERAVEPLIKALKDEDGWVRQSAADAL-
GEIG

GERVRAAMEKLAETGTGFARKVAVNYLETHK

In this aspect, design interfaces were grafted onto HEAT repeat scaffolds, permitting the designed polypeptides to direct their assembly into homo-oligomeric complexes (such as dimers, trimers, tetramers, and pentamers). "HEAT" is an acronym for four proteins in which this repeat structure is found: Huntingtin, elongation factor 3 (EF3), protein phosphatase 2A (PP2A), and the yeast kinase TOR1.

Oligomerizing positions for a variety of polypeptides of this aspect of the invention are shown Table 2, aligned with the wild-type reference sequences. These are the residues that drive homo-oligomerization of the polypeptides of this aspect; residues outside of these regions can be significantly modified without affecting oligomerization of the polypeptides.

TABLE 2

| Position | Heat reference sequence | 3ltjC3_int1 | 3ltjC3_int11 | T33_dn5B |
|---|---|---|---|---|
| 1 | — | — | R | — |
| 2 | — | — | R | — |
| 3 | — | — | E | — |
| 4 | T | — | E | — |
| 5 | D | D | D | D |
| 6 | P | P | P | P |
| 7 | E | L | L | L |
| 8 | K | A | A | A |
| 9 | V | | | |
| 10 | E | I | V | I |
| 11 | M | L | M | L |
| 12 | Y | Y | Y | Y |
| 13 | I | I | R | I |
| 14 | K | A | L | A |
| 15 | N | I | N | I |
| 16 | L | | | |

TABLE 2-continued

| Position | Heat reference sequence | 3ltjC3_int1 | 3ltjC3_int11 | T33_dn5B |
|---|---|---|---|---|
| 17 | Q | K | R | K |
| 18 | D | A |   | A |
| 19 | D | E |   | E |
| 20 | S | K |   | K |
| 21 | Y | S |   | S |
| 22 | Y | I |   | I |
| 23 | V | A |   | A |
| 24 | R |   |   |   |
| 25 | R | A |   | A |
| 26 | A | K |   | K |
| 27 | A |   |   |   |
| 28 | A |   |   |   |
| 29 | Y | E |   | E |
| 30 | A |   |   |   |
| 31 | L |   |   |   |
| 32 | G |   |   |   |
| 33 | K | K |   | K |
| 34 | I |   |   |   |
| 35 | G |   |   |   |
| 36 | D |   |   |   |
| 37 | E |   |   |   |
| 38 | R | R |   | R |
| 39 | A |   |   |   |
| 40 | V |   |   |   |
| 41 | E |   |   |   |
| 42 | P |   |   |   |
| 43 | L |   |   |   |
| 44 | I |   |   |   |
| 45 | K |   |   |   |
| 46 | A | A |   | A |
| 47 | L | L |   | L |
| 48 | K |   |   |   |
| 49 | D |   |   |   |
| 50 | E |   |   |   |
| 51 | D |   |   |   |
| 52 | A |   |   |   |
| 53 | W | L |   | L |
| 54 | V |   |   |   |
| 55 | R |   |   |   |
| 56 | R | L |   | L |
| 57 | A |   |   |   |
| 58 | A |   |   |   |
| 59 | A |   |   |   |
| 60 | D |   |   |   |
| 61 | A |   |   |   |
| 62 | L |   |   |   |
| 63 | G |   |   |   |
| 64 | Q |   |   |   |
| 65 | I |   |   |   |
| 66 | G |   |   |   |
| 67 | D |   |   |   |
| 68 | E |   |   |   |
| 69 | R |   |   |   |
| 70 | A |   |   |   |
| 71 | V |   |   |   |
| 72 | E |   |   |   |
| 73 | P |   |   |   |
| 74 | L |   |   |   |
| 75 | I |   |   |   |
| 76 | K |   |   |   |
| 77 | A |   |   |   |
| 78 | L |   |   |   |
| 79 | K |   |   |   |
| 80 | D |   |   |   |
| 81 | E |   |   |   |
| 82 | D | E |   | E |
| 83 | G |   |   |   |
| 84 | W | L |   | L |
| 85 | V |   |   |   |
| 86 | R |   |   |   |
| 87 | Q | A |   | A |
| 88 | S |   |   |   |
| 89 | A |   |   |   |
| 90 | A |   |   |   |
| 91 | V | I |   | I |
| 92 | A |   |   |   |
| 93 | L |   |   |   |
| 94 | G |   |   |   |
| 95 | Q |   |   |   |
| 96 | I |   |   |   |
| 97 | G |   |   |   |
| 98 | D |   |   |   |
| 99 | E |   |   |   |
| 100 | R |   |   |   |
| 101 | A |   |   |   |
| 102 | V |   |   | V |
| 103 | E |   |   | Q |
| 104 | P |   |   |   |
| 105 | L |   |   |   |
| 106 | I |   |   | I |
| 107 | K |   |   | K |
| 108 | A |   |   |   |
| 109 | L |   |   | L |
| 110 | K |   |   | T |
| 111 | D |   |   |   |
| 112 | E |   |   |   |
| 113 | D | R |   | R |
| 114 | W | D |   | D |
| 115 | F | L |   | L |
| 116 | V |   |   |   |
| 117 | R |   |   | R |
| 118 | I | V | A | V |
| 119 | A | A | A | A |
| 120 | A |   |   |   |
| 121 | A |   |   |   |
| 122 | F | V | A | V |
| 123 | A |   |   |   |
| 124 | L |   |   |   |
| 125 | G |   |   |   |
| 126 | E | R | R | R |
| 127 | I |   |   |   |
| 128 | G |   |   |   |
| 129 | D |   |   |   |
| 130 | E |   |   |   |
| 131 | R |   |   | K |
| 132 | A |   |   |   |
| 133 | V |   |   |   |
| 134 | E |   |   | R |
| 135 | P |   |   | P |
| 136 | L |   |   |   |
| 137 | I |   |   |   |
| 138 | K |   |   | I |
| 139 | A |   |   | V |
| 140 | L |   |   |   |
| 141 | K |   |   | K |
| 142 | D |   |   |   |
| 143 | E |   |   | E |
| 144 | D | E |   | E |
| 145 | G |   | E |   |
| 146 | W | E | M | E |
| 147 | V |   |   |   |
| 148 | R |   |   |   |
| 149 | Q | E | E | E |
| 150 | S | A | I | A |
| 151 | A |   |   |   |
| 152 | A |   |   |   |
| 153 | D | I | L | I |
| 154 | A |   |   |   |
| 155 | L |   |   |   |
| 156 | G |   |   |   |
| 157 | E | S | M | S |
| 158 | I |   |   |   |
| 159 | G |   |   |   |
| 160 | G |   |   |   |
| 161 | E |   |   |   |
| 162 | R |   |   |   |
| 163 | V |   |   |   |
| 164 | R |   |   |   |
| 165 | A |   |   |   |
| 166 | A |   |   |   |
| 167 | M |   |   |   |
| 168 | E |   |   |   |
| 169 | K |   |   |   |
| 170 | L |   |   |   |

TABLE 2-continued

| Position | Heat reference sequence | 3ltjC3_int1 | 3ltjC3_int11 | T33_dn5B |
|---|---|---|---|---|
| 171 | A | | | |
| 172 | E | | | |
| 173 | T | | | R |
| 174 | G | | | |
| 175 | T | | | |
| 176 | G | | | |
| 177 | F | | | |
| 178 | A | | | |
| 179 | R | | | |
| 180 | K | | | |
| 181 | V | | | |
| 182 | A | | | |
| 183 | V | | | |
| 184 | N | | | |
| 185 | Y | | | |
| 186 | L | | | |
| 187 | E | | | |
| 188 | T | | | |
| 189 | H | | | |
| 190 | K | | | |

In one embodiment of this aspect, the polypeptide amino acid sequence differs from SEQ ID NO: 11 at least as follows:

E7 is substituted with L or a conservative substitution thereof;

K8 is substituted with A or a conservative substitution thereof;

E10 is substituted with I, V or conservative substitutions thereof;

K14 is substituted with A, L or conservative substitutions thereof;

Q17 is substituted with R, K or conservative substitutions thereof;

I118 is substituted with A, V or conservative substitutions thereof;

F122 is substituted with A, V or conservative substitutions thereof;

W146 is substituted with E, M or conservative substitutions thereof;

Q149 is substituted with E or a conservative substitution thereof; and

S150 is substituted with I, A, or conservative substitutions thereof.

In another embodiment, the polypeptide amino acid sequence further differs from the amino acid sequence of SEQ ID NO: 11 at least at residues 11, 15, 18, 19, 20, 22, 23, 25, 26, 29, 82, 84, 87, 91, 113, 114, 115, and 144. In one such embodiment, the polypeptide amino acid sequence differs from SEQ ID NO: 11 at least as follows:

M11 is substituted with L or a conservative substitution thereof;

N15 is substituted with I or a conservative substitution thereof;

D18 is substituted with A or a conservative substitution thereof;

D19 is substituted with E or a conservative substitution thereof;

S20 is substituted with K or a conservative substitution thereof;

Y22 is substituted with I or a conservative substitution thereof;

V23 is substituted with A or a conservative substitution thereof;

R25 is substituted with A or a conservative substitution thereof;

A26 is substituted with K or a conservative substitution thereof;

Y29 is substituted with E or a conservative substitution thereof;

D82 is substituted with E or a conservative substitution thereof;

W84 is substituted with L or a conservative substitution thereof;

Q87 is substituted with A or a conservative substitution thereof;

V91 is substituted with I or a conservative substitution thereof;

D113 is substituted with R or a conservative substitution thereof;

W114 is substituted with D or a conservative substitution thereof;

F115 is substituted with L or a conservative substitution thereof; and

D144 is substituted with E or a conservative substitution thereof.

In another aspect, the invention provides polypeptides comprising or consisting of a polypeptide having at least 50% identity over its length with a polypeptide having the amino acid sequence selected from the group consisting of SEQ ID NOs: 10 and 12-40. As described in the examples that follow, the polypeptides of the invention were designed for their ability to self-assemble to cyclic homoligomers with tunable shape, size, and symmetry enables rigid display of binding domains at arbitrary orientations and distances for a range of biological applications.

In various embodiments, the polypeptides comprise or consist of a polypeptide having at least 55%, 60%, 65%, 70%, 75%, 80%, 85%, 90%, 95%, 96%, 97%, 98%, 99%, or 100% identity over its length with a polypeptide having the amino acid sequence selected from the group consisting of SEQ ID NOs: 10 and 12-40. Oligomerizing positions are in bold font.

Ankyrin Based Oligomers

>ank1C2_1 (ank1C2_G3)
(SEQ ID NO: 12)
SELGKRLIEAAENGNKDRVKDLIENGADVNASDSDGRTPLHHAAENG-
HAEVV
ALLIEKGADVNAKDSDGRTPLHHAAENGHDEVVLILLLKGADVNAKDS-
DGRT
PLHHAAENGHKRVVLVLILAGADVNTSDSDGRTPLDLAREHGNEEVVKA-
LEK
Q

>ank1C4_2 (ank1C4_7)
(SEQ ID NO: 13)
SEDGELLILAAELGIAEAVRMLIEQGADVNASDDDGRTPLH-
HAAENGHLAVV
LLLLLKGADVNAKDSDGRTPLHHAAENGHKTVVLLLILMGADVNAKDS-
DGRT
PLHHAAENGHKEVVKLLIRKGADVNTSDSDGRTPLDLAREH-
GNEEVVKLLEK
Q

>ank3C2_1
(SEQ ID NO: 14)
SELGKRLIEAAENGNKDRVKDLLENGADVNASDSDGKTPLHLAAENG-
HAKVV
LLLLEQGADPNAKDSDGKTPLHLAAENGHAVVVALLLMHGADPNAKDS-
DGKT
PLHLAAENGHEEVVILLLAMGADPNTSDSDGRTPLDLAREHGNEEVVKV-
LED
H

>ank4C4 (ank4C4.2, D2 residues selected here)
(SEQ ID NO: 15)
STEGKMLIIAAREGMIIVVIVLLEKGADPNASDKDGRTPLHYAAENGH-
LIIV
LLLLEKGADPNAKDSDGRTPLHYAAENGHKEIVEALLEHGADPNAKDS-
DGRT -continued
PLHYAAENGHKEIVKLLLSKGADPNTSDSDGRTPLDLAREHGNEE-
IVKLLEK
QLE TPR Based Oligomers >1na0C3_1
(SEQ ID NO: 16)
ERAEMAAIVGDAIYIMGLYRLAIKMYLIALKLDPNNAEAWYNLGNAYYKQ
GDYDEAIEYYQKALELDPNNAEAWYNLGNAYYKQGDYDEAIEYYQKALEL
DPNNAEAKQNLGNAKQKQG >1na0C3_int2*
(SEQ ID NO: 17)
EEAELAYLLGELAYKLGEYRIAIRAYRIALKRDPNNAEAWYNLGNAYYKQ
GDYDEAIEYYQKALELDPNNAEAWYNLGNAYYKQGDYDEAIEYYQKALEL
DPNNAEAKQNLGNAKQKQG >1na0C3_3
(SEQ ID NO: 18)
NLAEKMYKAGNAMYRKGQYTIAIIAYTLALLKDPNNAEAWYNLGNAAYKK
GEYDEAIEAYQKALELDPNNAEAWYNLGNAYYKQGDYDEAIEYYQKALEL
DPNNAEAKQNLGNAKQKQG >1na0C3_5 (1na0C3_6)
(SEQ ID NO: 19)
NEAELAYDLGNEAYKDGEYRLAAVAYVLALAVDPNNAEAWYNLGNAYYKQ
GRYDKAIKYYQKALELDPNNAEAWYNLGNAYYKQGDYDEAIEYYQKALEL
DPNNAEAKQNLGNAKQKQG >1na0C3_7 (1na0C3_G1)
(SEQ ID NO: 20)
NSAEAMYKMGNAAYKQGDYILAIIAYLLALEKDPNNAEAWYNLGNAAYKQ
GDYDEAIEYYQKALELDPNNAEAWYNLGNAYYKQGDYDEAIEYYQKALEL
DPNNAEAKQNLGNAKQKQG >1na0C4_1 (1na0C4_G1)
(SEQ ID NO: 21)
TLARVAYILGAIAYAQGEYDIAITAYQVALDLDPNNAEAWYNLGNAYYKQ
GDYDEAIEYYQKALELDPNNAEAWYNLGNAYYKQGDYDEAIEYYQKALEL
DPNNAEAKQNLGNAKQKQG >tpr 1 C4_2 (tpr1C4_pm3 )
(SEQ ID NO: 10)
ASSWVMLGLLLSLLNRLSLAAEAYKKAIELDPNDALAWLLLGSVLEKLKR
LDEAAEAYKKAIELKPNDASAWKELGKVLEKLGRLDEAAEAYKKAIELDP
EDAEAWKELGKVLEKLGRLDEAAEAYKKAIELDPND HEAT Based Oligomers >3ltjC3_int1*
(SEQ ID NO: 22)
TDPLAVILYIAILKAEKSIARAKAAEALGKIGDERAVEPLIK**ALKLDEDAL
VRAAAADALGQIGDERAVEPLIKALKDEEGLVRASAAI**ALGQIGDERAVE
PLIKALKDERDLVRVAAAVALGRIGDERAVEPLIKALKDEEGEVRE**AAAI
ALGS**IGGERVRAAMEKLAETGTGFARKVAVNYLETHK >3ltjC3_int11*
(SEQ ID NO: 23)
RREEDPLAVVMYRLNLRDDSYYVRRAAAYALGKIGDERAVEPLIKALKDE
DAWVRRAAADALGQIGDERAVEPLIKALKDEDGWVRQSAAVALGQIGDER
AVEPLIKALKDEDWFVRAAAAAALGRIGDERAVEPLIKALKDED**EMVREI
AALA**LGMIGGERVRAAMEKLAETGTGFARKVAVNYLETHK HR Based Oligomers >HR00C3_2
(SEQ ID NO: 24)
IEEVVAEMIDILAESSKKSIEELARAADNKTTEKAVAEAIEEEIARLATAAI
QLIEALAKNLASEEFMARAISAIAELAKKAIEAIYRLADNHTTDTFMARAI
AAIANLAVTAILAIAALASNHTTEEFMARAISAIAELAKKAIEAIYRLADN
HTTDKFMAAAIEAIALLATLAILAIALLASNHTTEEFMAKAISAIAELAKK

AIEAIYRLADNHTSPTYIEKAIEAIEKIARKAIKAIEMLAKNITTEEYKEK

AKSAIDEIREKAKEAIKRLEDNRT

>HR04C3_int2 (tj04C3_int5v2)*
(SEQ ID NO: 25)
DECEEKARRVAEKVERLKRSGTSEDEIAEEVAREISEVIRTLKESGSEYKV

ICRCVARIVAEIVEALKRSGTSEDEIAEIVARVISEVIRTLKESGSDYLII

CVCVAIIVAEIVEALKRSGTSEDEIAEIVARVISEVIRTLKESGSSYEVIK

ECVQIIVLAIILALMKSGTEVEEILLILLRVKTEVRRTLKESGS

>HR04C4_1 (tj10C4_G1)
(SEQ ID NO: 26)
DECEEKARRVAEKVERLKRSGTSEDEIAEEVAREISEVIRTLKESGSSYEV

ICECVARIVAEIVEALKRSGTSAVEIAKIVARVISEVIRTLKESGSSYEVI

CECVARIVAEIVEALKRSGTSAAIIALIVALVISEVIRTLKESGSSFEVIL

ECVIRIVLEIIEALKRSGTSEQDVMLIVMAVLLVVLATLQLSGS

>HR08C3 (tj08C3_V13)
(SEQ ID NO: 27)
DEMRKVMLALAIALVRALLNEDIEVAKEIARAADEIEEALRENNSDEMAKV

MLALAKAVLLAAKNNDDRVAEVIALAAAEIVKALRRNNSDEMAKVMLALAK

AVLLAAKNNDDEVAKEIAIAAMIIVIALRAENSDEMAKKMLELAKRVLDAA

KNNDDETAREIAEQAAEELEA

>HR10C2_2 (bex2C2_G2)
(SEQ ID NO: 28)
SSEKEELRERLVKIVVENAKRKGDDTEEAREAARAAFEIVRAAAKLAGIDS

SEVLELAIRLIKEVVENAQREGYDIAVAAIAAAVAFAVVAVAAAAADITSS

EVLELAIRLIKEVVENAQREGYVILLAALAAAAAFVVVAAAAKRAGITSSE

TLKRAIEEIRKRVEEAQREGNDISEAARQAAEEFRKKAEELK

>HR10C5_2 (bex2C5_G2)
(SEQ ID NO: 29)
SAEKLMLMAKLIIIVAENAKRKGDDTLIAIMAAKLAFEIVRIAAEEAGIDS

SEVLELAIRLIKEVVENAQREGYDISIAALAAAMAFALVAIAAKRAGITSS

EVLELAIRLIKEVVENAQREGYDIAEAARAAAEAFKRVAEAAKRAGITSSE

TLKRAIEEIRKRVEEAQREGNDISEAARQAAEEFRKKAEELK

>HR18C2 (tj18C2_V03)*
(SEQ ID NO: 30)
RIEKLCRIAEALAREARSKAEELRQRHPDSQAARDAQKLASQAEEAVKLAC

ELAQEHPNAIIAILCIVAAIAAAIAASMAAALAQRHPDSQAARDAIKLASQ

AAEAVKLACELAQEHPNAKIAVLCILAAALAAIAAALAALLAQLHPDSQAA

RDAIKLASQAAEAVKLACELAQEHPNADIAEKCILLAILAALLAILAALLA

MLHPDSQLARDLIDLASELAEEVKERCER

>HR79C2 (tj79C2_V01)
(SEQ ID NO: 31)
REDELRARLLILLAELAAERADIAAERTGDPRVRELARELKRLAQEEAAEEV

KRDPSSSDVNEALKLIVEMEAAVRALEAAERTGDPEVRELARELVRLAVEA

AEEVQRNPSSSDVNEALKLIVEAIEAAVRALEAAERTGDPEVRELARELVR

LAVEAAEEVQRNPSSKEVDMALLLILIAILEAVLSLLRAERSGDPEKREKA

RERVREAVERAEEVQRDPS

>HR81 C2 (tj 81 C2_V39)
(SEQ ID NO: 32)
EREELSELAERILQKARKLSEEARERGDLKELALALILEALAVLLLAIAAL

LRGNSEEAERASEKAQRVLEEARKVSEEAREQGDDEVLALALIAIALAVLA

LALVACCRGNSEEAERASEKAQRVLEEARKVSEEAREQGDDEVLALALIAI

ALAVLALAIVACCRGNKEEAERAAEDAIKVAMEALEVLLSAVEQGDLKVAL

AAVIAILLAIAALLMVIMCKG

>T33_dn2A* (Based on 1na0C3_3)
(SEQ ID NO: 33)
NLAEKMYKAGNAMYRKGQYTIAIIAYTLALLKDPNNAEAWYNLGNAAYK-
KGE
YDEAIEAYQKALELDPNNAEAWYNLGNAYYKQGDYDEAIEYYKKALRLD-
PRN
VDAIENLIEAEEKQG >T33_dn2B* (Based on 1na0C3_int2)
(SEQ ID NO: 34)
EEAELAYLLGELAYKLGEYRIAIRAYRIALKRDPNNAEAVVYNLG-
NAYYKQG
DYREAIRYYLRALKLDPENAEAWYNLGNALYKQGKYDLAIIAYQAA-
LEEDPN
NAEAKQNLGNAKQKQG >T33_dn5A* (Based on 1na0C3_G1)
(SEQ ID NO: 35)
NSAEAMYKMGNAAYKQGDYILAIIAYLLALEKDPNNAEAWYNLG-
NAAYKQG
DYDEAIEYYQKALELDPNNAEAWYNLGNAYYKQGDYDEAIEYYEKA-
LELDPN
NAEALKNLLEAIAEQD >T33_dn5B* (Based on 3LtjC3_int1)
(SEQ ID NO: 36)
TDPLAVILYIAILKAEKSIARAKAAEALGKIGDERAVEPLIKALKDED-
ALVR

AAAADALGQIGDERAVEPLIKALKDEEGLVRASAAIALGQIGDERAVQP-
LIK

ALTDERDLVRVAAAVALGRIGDEKAVRPLIIVLKDEEGEVREAAAIALG-
SIG

GERVRAAMEKLAERGTGFARKVAVNYLETHK

>T33_dn10A* (Based on 1na0C3_int2)
(SEQ ID NO: 37)
EEAELAYLLGELAYKLGEYRIAIRAYRIALKRDPNNAEAVVYNLG-
NAYYKQG
DYDEAIEYYQKALELDPNNAEAWYNLGNAYYKQGDYDEAIEYYEKA-
LELDPE
NLEALQNLLNAMDKQG >T33_dn10B* (Based on HR0003_2)
(SEQ ID NO: 38)
IEEVVAEMIDILAESSKKSIEELARAADNKTTEKAVAEAIEEIARLA-
TAAIQ

LIEALAKNLASEEFMARAISAIAELAKKAIEAIYRLADNHTTDTF-
MARAIAA

IANLAVTAILAIAALASNHTTEEFMARAISAIAELAKKAIEAIYRLAD-
NHTT

DKFMAAAIEAIALLATLAILAIALLASNHTTEKFMARAIMAIAI-
LAAKAIEA

IYRLADNHTSPTYIEKAIEAIEKIARKAIKAIEMLAKNITTEEYKEKAK-
KII

DIIRKLAKMAIKKLEDNRT

>T53_dn5A*
(SEQ ID NO: 39)
KYDGSKLRIGILHARVVNAEIILALVLGALKRLQEFGVKRENIIIET-
VPGSF
ELPYGSKLFVEKQKRLGKPLDAIIPIGVLIKGSTMHFEYICDSTTHQLM-
KLN
FELGIPVIFGVLTCLTDEQAEARAGLIEGKMHNHGEDWGAAAVEMATKFN

>T53_dn5B* (Based on 1na0C3_int2)
(SEQ ID NO: 40)
EEAELAYLLGELAYKLGEYRIAIRAYRIALKRDPNNAEAVVYNLG-
NAYYKQG
RYREAIEYYQKALELDPNNAEAVVYNLGNAYYERGEYEEAIEYYRKAL-
RLDPN
NADAMQNLLNAKMREE In another embodiment, all oligomerizing positions in the amino acid sequence selected from the group consisting of SEQ ID NO: 10 and 12-40 have the amino acid residue shown in the amino acid sequence selected from the group consisting of SEQ ID NO: 10 and 12-40, or conservative substitutions thereof.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by poly-ethylene gycol-ylation (PEGylation), hydroxyethl starch-ylation (HESylation), Pro, Ala, and/or Ser-ylation (PASylation), glycosylation, or may be produced as an Fc-fusion or in deimmunized variants. Such linkage can be covalent or non-covalent as is understood by those of skill in the art.

In various embodiments of all aspects and embodiments of the invention, the polypeptides and individual domains thereof may comprise or consist of the amino acid sequence having at least 55%, 60%, 65%, 70%, 75%, 80%, 85%, 90%, 95%, 96%, 97%, 98%, 99%, or 100% identity over its length with the reference sequence.

As will be understood by those of skill in the art, the polypeptides of the invention may include additional residues at the N-terminus, C-terminus, or both that are not present in the polypeptides disclosed herein; these additional residues are not included in determining the percent identity of the polypeptides of the invention relative to the reference polypeptide.

As used herein, "conservative amino acid substitution" means amino acid or nucleic acid substitutions that do not alter or substantially alter polypeptide or polynucleotide function or other characteristics. Amino acids can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As noted above, the polypeptides of the invention may include additional residues at the N-terminus, C-terminus, or both. Such residues may be any residues suitable for an intended use, including but not limited to detection tags (i.e.: fluorescent proteins, antibody epitope tags, etc.), linkers, ligands suitable for purposes of purification (His tags, etc.), and peptide domains that add functionality to the polypeptides, such as a polypeptide to be displayed on the surface of the homo-oligomers formed from the polypeptides of the invention (i.e.: a "cargo").

In another embodiment, the invention provides homooligomeric protein assemblies, comprising a plurality of polypeptides of the present invention having the same amino acid sequence. Such homo-oligomeric assemblies may comprise, for example, dimers, trimers, tetramers, and pentamers.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting host cells is well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In various embodiments, the expression vector may comprise a plasmid, viral-based vector, or any other suitable expression vector.

In a further aspect, the present invention provides host cells that comprise the recombinant expression vectors disclosed herein, wherein the host cells can be either prokaryotic or eukaryotic. The cells can be transiently or stably engineered to incorporate the expression vector of the invention, using standard techniques in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the person skilled in the art.

In another aspect, the invention provides computational methods for designing polypeptides that can self-assemble into homoligomers.

Example Computing Environment

FIG. 1 is a block diagram of an example computing network. Some or all of the above-mentioned techniques disclosed herein, such as but not limited to techniques disclosed as part of and/or being performed by software, the Rosetta software suite, RosettaDesign®, Rosetta applications, and/or other herein-described computer software and computer hardware, can be part of and/or performed by a computing device. For example, FIG. 1 shows protein design system 102 configured to communicate, via network 106, with client devices 104a, 104b, and 104c and protein database 108. In some embodiments, protein design system 102 and/or protein database 108 can be a computing device configured to perform some or all of the herein described methods and techniques, such as but not limited to, method 300 and functionality described as being part of or related to Rosetta. Protein database 108 can, in some embodiments, store information related to and/or used by Rosetta®.

Network 106 may correspond to a LAN, a wide area network (WAN), a corporate intranet, the public Internet, or any other type of network configured to provide a communications path between networked computing devices. Network 106 may also correspond to a combination of one or more LANs, WANs, corporate intranets, and/or the public Internet.

Although FIG. 1 only shows three client devices 104a, 104b, 104c, distributed application architectures may serve tens, hundreds, or thousands of client devices. Moreover, client devices 104a, 104b, 104c (or any additional client devices) may be any sort of computing device, such as an ordinary laptop computer, desktop computer, network terminal, wireless communication device (e.g., a cell phone or smart phone), and so on. In some embodiments, client devices 104a, 104b, 104c can be dedicated to problem solving/using the Rosetta software suite. In other embodiments, client devices 104a, 104b, 104c can be used as general purpose computers that are configured to perform a number of tasks and need not be dedicated to problem solving/using the Rosetta software suite. In still other embodiments, part or all of the functionality of protein design system 102 and/or protein database 108 can be incorporated in a client device, such as client device 104a, 104b, and/or 104c.

Computing Environment Architecture

Figure 2A:
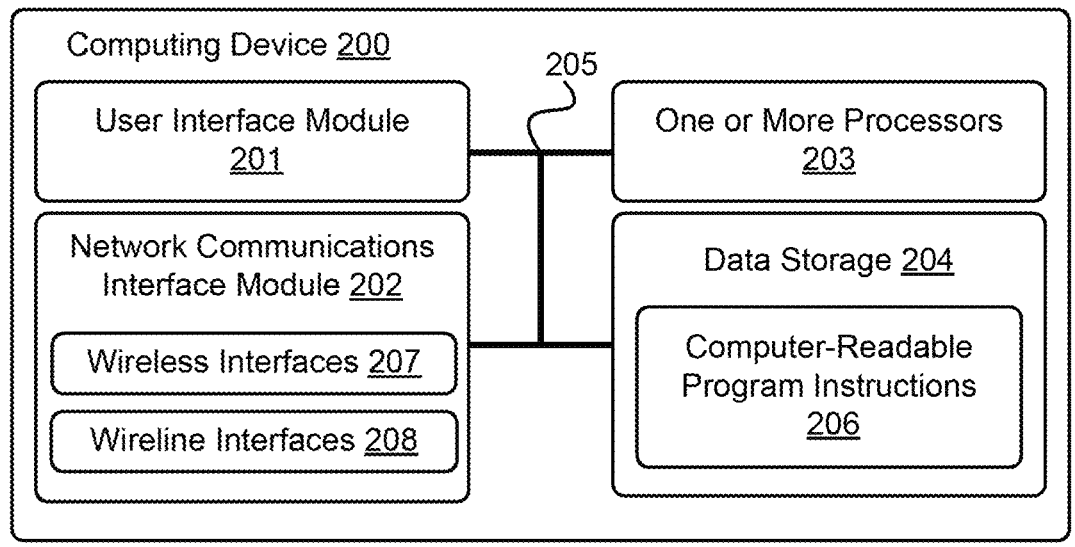
FIG. 2A: A block diagram of an example computing device.

FIG. 2A is a block diagram of an example computing device (e.g., system) In particular, computing device 200 shown in FIG. 2A can be configured to: include components of and/or perform one or more functions of some or all of the herein described methods and techniques, such as but not limited to, method 300 and functionality described as being part of or related to Rosetta. Computing device 200 may include a user interface module 201, a network-communication interface module 202, one or more processors 203, and data storage 204, all of which may be linked together via a system bus, network, or other connection mechanism 205.

User interface module 201 can be operable to send data to and/or receive data from external user input/output devices. For example, user interface module 201 can be configured to send and/or receive data to and/or from user input devices such as a keyboard, a keypad, a touch screen, a computer mouse, a track ball, a joystick, a camera, a voice recognition module, and/or other similar devices. User interface module 201 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 201 can also be configured to generate audible output(s), such as a speaker, speaker jack, audio output port, audio output device, earphones, and/or other similar devices.

Network-communications interface module 202 can include one or more wireless interfaces 207 and/or one or more wireline interfaces 208 that are configurable to communicate via a network, such as network 106 shown in FIG. 1. Wireless interfaces 207 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 208 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 202 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 203 can include one or more general purpose processors and/or one or more special purpose processors (e.g., digital signal processors, application specific integrated circuits, etc.). Processors 203 can be configured to execute computer-readable program instructions 206 contained in data storage 204 and/or other instructions as described herein. Data storage 204 can include one or more computer-readable storage media that can be read and/or accessed by at least one of processors 203. The one or more computer-readable storage media can include volatile and/or non-volatile storage components, such as optical, magnetic, organic or other memory or disc storage, which can be integrated in whole or in part with at least one of processors 203. In some embodiments, data storage 204 can be implemented using a single physical device (e.g., one optical, magnetic, organic or other memory or disc storage unit), while in other embodiments, data storage 204 can be implemented using two or more physical devices.

Data storage 204 can include computer-readable program instructions 206 and perhaps additional data. For example, in some embodiments, data storage 204 can store part or all of data utilized by a protein design system and/or a protein database; e.g., protein designs system 102, protein database 108. In some embodiments, data storage 204 can additionally include storage required to perform at least part of the herein-described methods and techniques and/or at least part of the functionality of the herein-described devices and networks.

Figure 2B:
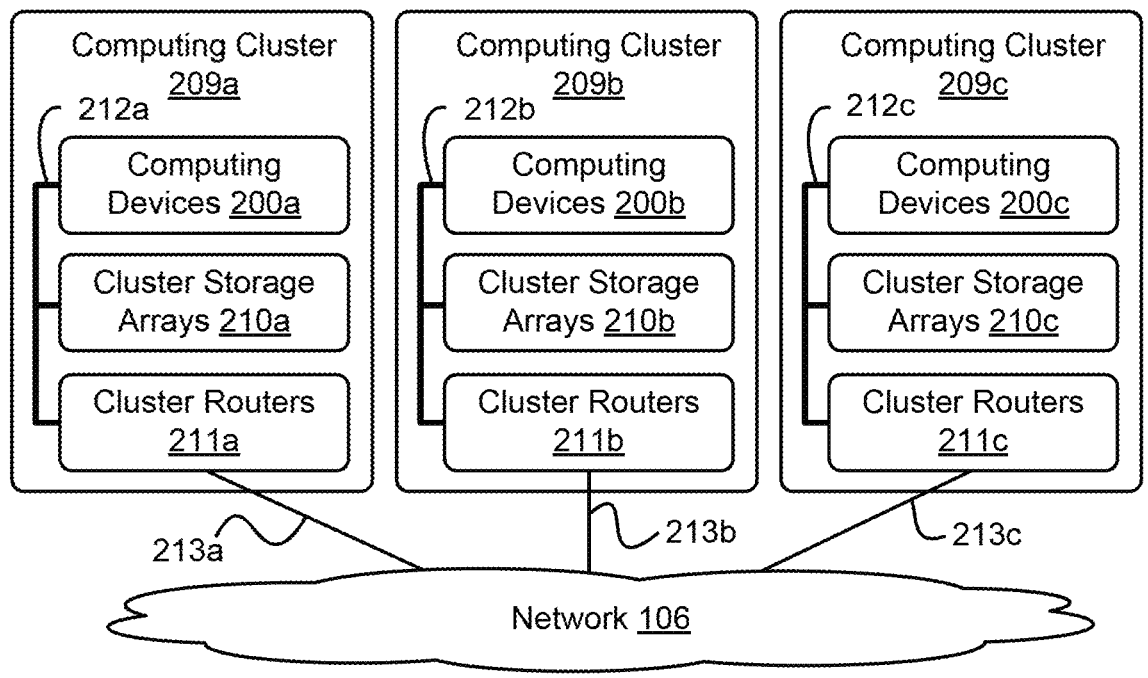
FIG. 2B: A block diagram of an example network of computing devices arranged as a cloud-based server system.

FIG. 2B depicts a network 106 of computing clusters 209a, 209b, 209c arranged as a cloud-based server system in accordance with an example embodiment. Data and/or software for protein design system 102 can be stored on one or more cloud-based devices that store program logic and/or data of cloud-based applications and/or services. In some embodiments, protein design system 102 can be a single computing device residing in a single computing center. In other embodiments, protein design system 102 can include multiple computing devices in a single computing center, or even multiple computing devices located in multiple computing centers located in diverse geographic locations.

In some embodiments, data and/or software for protein design system 102 can be encoded as computer readable information stored in tangible computer readable media (or computer readable storage media) and accessible by client devices 104a, 104b, and 104c, and/or other computing devices. In some embodiments, data and/or software for protein design system 102 can be stored on a single disk drive or other tangible storage media, or can be implemented on multiple disk drives or other tangible storage media located at one or more diverse geographic locations.

FIG. 2B depicts a cloud-based server system in accordance with an example embodiment. In FIG. 2B, the functions of protein design system 102 can be distributed among three computing clusters 209a, 209b, and 209c. Computing cluster 209a can include one or more computing devices 200a, cluster storage arrays 210a, and cluster routers 211a connected by a local cluster network 212a. Similarly, computing cluster 209b can include one or more computing devices 200b, cluster storage arrays 210b, and cluster routers 211b connected by a local cluster network 212b. Likewise, computing cluster 209c can include one or more computing devices 200c, cluster storage arrays 210c, and cluster routers 211c connected by a local cluster network 212c.

In some embodiments, each of the computing clusters 209a, 209b, and 209c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 209a, for example, computing devices 200a can be configured to perform various computing tasks of protein design system 102. In one embodiment, the various functionalities of protein design system 102 can be distributed among one or more of computing devices 200a, 200b, and 200c. Computing devices 200b and 200c in computing clusters 209b and 209c can be configured similarly to computing devices 200a in computing cluster 209a. On the other hand, in some embodiments, computing devices 200a, 200b, and 200c can be configured to perform different functions.

In some embodiments, computing tasks and stored data associated with protein design system 102 can be distributed across computing devices 200a, 200b, and 200c based at least in part on the processing requirements of protein design system 102, the processing capabilities of computing devices 200a, 200b, and 200c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 210a, 210b, and 210c of the computing clusters 209a, 209b, and 209c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of protein design system 102 can be distributed across computing devices 200a, 200b, and 200c of computing clusters 209a, 209b, and 209c, various active portions and/or backup portions of these components can be distributed across cluster storage arrays 210a, 210b, and 210c. For example, some cluster storage arrays can be configured to store one portion of the data and/or software of protein design system 102, while other cluster storage arrays can store a separate portion of the data and/or software of protein design system 102. Additionally, some cluster storage arrays can be configured to store backup versions of data stored in other cluster storage arrays.

The cluster routers 211a, 211b, and 211c in computing clusters 209a, 209b, and 209c can include networking equipment configured to provide internal and external communications for the computing clusters. For example, the cluster routers 211a in computing cluster 209a can include one or more internet switching and routing devices configured to provide (i) local area network communications between the computing devices 200a and the cluster storage arrays 201a via the local cluster network 212a, and (ii) wide area network communications between the computing cluster 209a and the computing clusters 209b and 209c via the wide area network connection 213a to network 106. Cluster routers 211b and 211c can include network equipment similar to the cluster routers 211a, and cluster routers 211b and 211c can perform similar networking functions for computing clusters 209b and 209b that cluster routers 211a perform for computing cluster 209a.

In some embodiments, the configuration of the cluster routers 211a, 211b, and 211c can be based at least in part on the data communication requirements of the computing devices and cluster storage arrays, the data communications capabilities of the network equipment in the cluster routers 211a, 211b, and 211c, the latency and throughput of local networks 212a, 212b, 212c, the latency, throughput, and cost of wide area network links 213a, 213b, and 213c, and/or other factors that can contribute to the cost, speed, fault-tolerance, resiliency, efficiency and/or other design goals of the moderation system architecture.

Example Methods of Operation

FIG. 3 is a flow chart of an example method 300. Method 300 can be carried out by a computing device, such as computing device 200 described in the context of at least FIG. 2A. At least the embodiments of method 300 mentioned below are discussed herein.

Method 300 can begin at block 310, where the computing device can determine a cycle of monomeric proteins.

At block 320, the computing device can determine a docking score for the cycle of monomeric proteins using the computing device, the docking score representing interaction between two or more monomeric proteins in the cycle of monomeric proteins with respect to a multi-dimensional rigid body transformation between one or more backbone atoms of the two or more monomeric proteins. In some embodiments, determining a docking score can include determining a docking score representing interaction between the two or more monomeric proteins in the cycle of monomeric proteins with respect to a six-or-more-dimensional rigid body transformation. In particular of these embodiments, determining the docking score representing interaction between the two or more monomeric proteins in the cycle of monomeric proteins with respect to the six-or-more-dimensional rigid body transformation can include:

determining that the two or more monomeric proteins come into contact; and after determining that the two or more monomeric proteins come into contact, reducing the six-or-more-dimensional rigid body transformation to a three-or-more-dimensional rigid body transformation. In other of these embodiments, determining that the two or more monomeric proteins come into contact can include determining that the two or more monomeric proteins come into contact based on a slide vector that brings the two or more monomeric proteins into contact. In even other of these embodiments, determining that the two or more monomeric proteins come into contact based on a slide vector that brings the two or more monomeric proteins into contact can include determining a slide distance between the two or more monomeric proteins using the slide vector. In still other of these embodiments, determining that the two or more monomeric proteins come into contact can include determining a slide distance between the two or more monomeric proteins using an octree.

At block 330, the computing device can determine whether the docking score for the cycle of monomeric proteins is a relatively-low docking score. In some embodiments, determining the docking score can include determining a plurality of bins for two or more monomeric proteins, each bin representing a particular position and a particular orientation of the two or more monomeric proteins. In particular of these embodiments, each bin of the plurality of bins can include a bin index determined using a hash transform computed for the particular position and the particular orientation of the two or more monomeric proteins. In some of these embodiments, the hash transform can receive backbone atom positions of the two or more monomeric proteins as inputs. In other of these embodiments, the hash transform can compute a rigid body transformation between at least three backbone atom positions of the two or more monomeric proteins. In still other of these embodiments, the at least three backbone atom positions comprise positions for at least one nitrogen atom, at least one alpha-carbon atom, and at least one carbon atom.

At block 340, after determining that the docking score for the cycle of monomeric proteins is a relatively-low docking score, the computing device can determine one or more interfaces between the two or more monomeric proteins in the cycle of monomeric proteins. In some embodiments, the cycle of monomeric proteins can include a particular monomer; then, determining whether the docking score for the cycle of monomeric proteins is a relatively-low docking score can include: determining a plurality of docking scores for a plurality of cycles of monomeric proteins that each include the particular monomer; determining a predetermined number of lowest docking scores of the plurality of docking scores; determining whether the docking score for the cycle of monomeric proteins is a docking score of the predetermined number of lowest docking scores; and after determining that the docking score for the cycle of monomeric proteins is a docking score of the predetermined number of lowest docking scores, determining that the docking score for the cycle of monomeric proteins is a relatively-low docking score. In other embodiments, the cycle of monomeric proteins includes a particular monomer; then, determining whether the docking score for the cycle of monomeric proteins is a relatively-low docking score can include: determining a plurality of docking scores for a plurality of cycles of monomeric proteins that each include the particular monomer; determining a threshold docking score value; determining whether the docking score for the cycle of monomeric proteins is less than the threshold docking score value; and after determining that the docking score for the cycle of monomeric proteins is less than the threshold docking score value, determining that the docking score for the cycle of monomeric proteins is a relatively-low docking score.

At block 350, the computing device and/or one or more other entities can generate an output related to the cycle of monomeric proteins. In some embodiments, generating the output related to the cycle of monomeric proteins can include designing one or more molecules based on the cycle of monomeric proteins. In other embodiments, generating the output related to the cycle of monomeric proteins can include: generating a synthetic gene that is based the cycle of monomeric proteins; expressing a particular protein in vivo using the synthetic gene; and purifying the particular protein. In some of these embodiments, expressing the particular protein sequence in vivo using the synthetic gene can include expressing the particular protein sequence in one or more *Escherichia coli* that include the synthetic gene. In even other embodiments, generating the output related to the cycle of monomeric proteins comprises generating one or more images that include at least part of the cycle of monomeric proteins.

In some examples, at least a portion of method 300 is performed by a computing device that includes: one or more processors; and non-transitory data storage, configured to store at least computer-readable instructions that, when executed, cause the computing device to perform the at least a portion of method 300.

In other examples, a non-transitory computer-readable medium is provided, where the computer-readable medium is configured to store at least computer-readable instructions that, when executed by one or more processors of a computing device, cause the computing device to perform at least a portion of method 300.

In still other examples, an apparatus is provided, where the apparatus can include means to perform at least a portion of method 300.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or nonvolatile storage systems. A computer readable medium may be considered a computer readable storage medium, for example, or a tangible storage device. Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

EXAMPLES

Self-assembling cyclic protein homo-oligomers play important roles in biology and the ability to generate custom homo-oligomeric structures could enable new approaches to probe biological function. Here we report a general approach to design cyclic homo-oligomers that employs a new residue pair transform method for assessing the designability of a protein-protein interface. This method is sufficiently rapid to allow systematic enumeration of cyclically docked arrangements of a monomer followed by sequence design of the newly formed interfaces. We use this method to design interfaces onto idealized repeat proteins that direct their assembly into complexes that possess cyclic symmetry. Of 96 designs that were experimentally characterized, 21 were found to form stable monodisperse homo-oligomers in solution, and 15 (4 homodimers, 6 homotrimers, 6 homotetramers and 1 homopentamer) had solution small angle X-ray scattering data consistent with the design models. X-ray crystal structures were obtained for five of the designs and each of these were shown to be very close to their design model.

Cyclic homo-oligomers assembled from multiple identical protein subunits symmetrically arranged around a central axis play key roles in many biological processes including catalysis, signaling and allostery. Despite their prevalence in natural systems, currently there is no systematic approach to design cyclic homo-oligomers starting from a monomeric protein structure.

Here we present a general method for designing cyclic homo-oligomers in silico and use it to design interfaces onto recently developed repeat proteins that direct their assembly into dimeric, trimeric, tetrameric and pentameric complexes. Structural characterization shows that many of the designs adopt the target oligomerization state and structure, demonstrating that we have a basic understanding of the determinants of oligomerization state. The capability of designing proteins with tunable shape, size, and symmetry enables rigid display of binding domains at arbitrary orientations and distances for a range of biological applications.

Results

Figure 5:
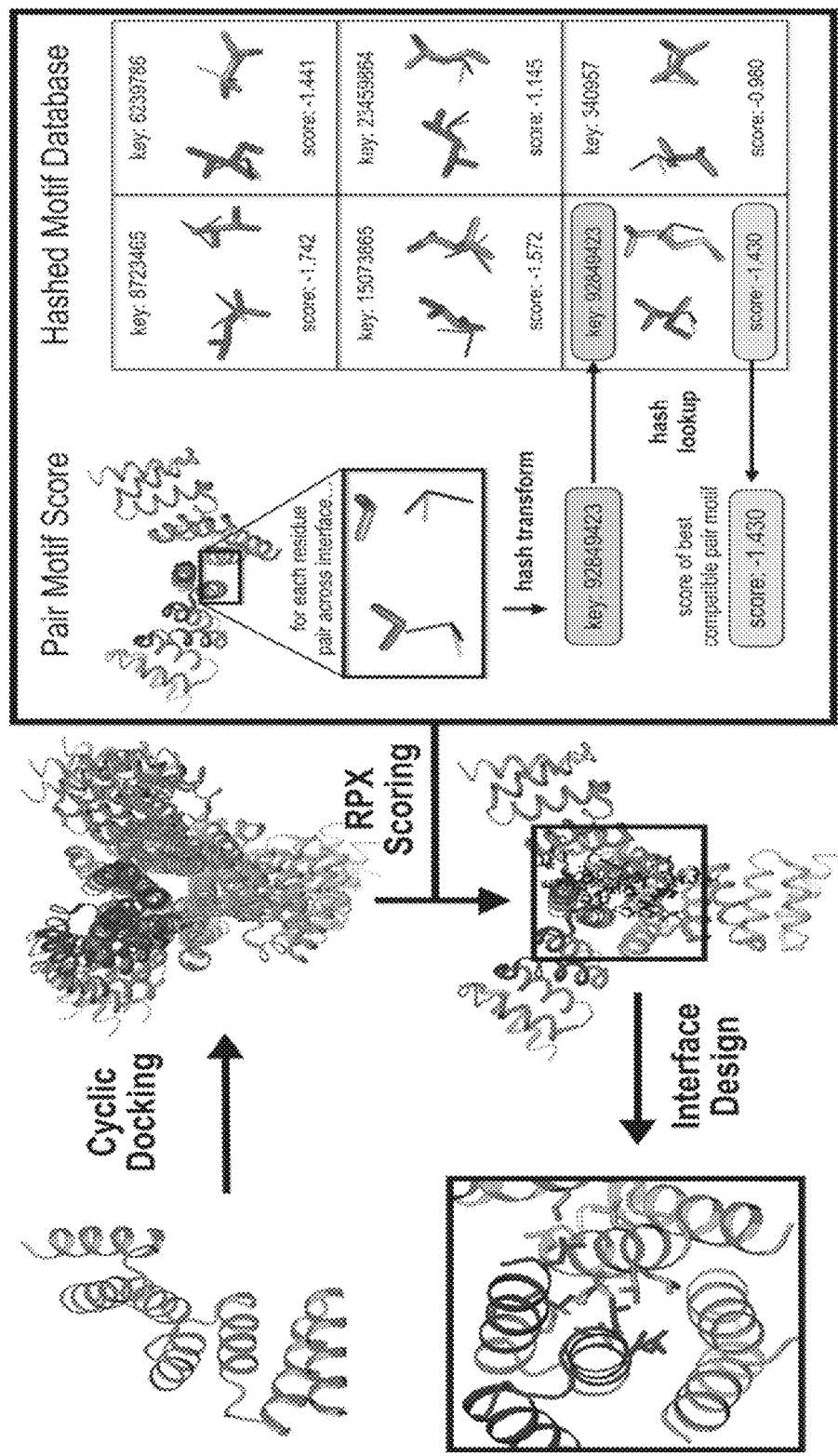
FIG. 5: Computational design protocol. Left, starting with a monomeric protein we exhaustively sample cyclic docked configurations, score them using the RPX model and generate sequences to drive the complex formation using a full atom RosettaDesign® calculation. Right, schematic representation of the RPX model scoring procedure.

The self-assembly of naturally occurring complexes is driven by chemical and shape complementarity. Protein-protein interfaces are generally comprised of a hydrophobic core that is buried upon binding and surrounded by a rim of polar residues that prevent non-specific aggregation. We developed a design strategy to generate such interfaces between protein monomers docked in a range of cyclic geometries. The strategy has two steps (FIG. 5): first, low resolution docking to sample and rank symmetric arrangements of a given scaffold protein based on their designability (the likelihood of finding an amino acid sequence that can stabilize a given rigid body conformation), and second, full atom RosettaDesign® calculations to optimize the sequence at the protein-protein interfaces for high affinity binding. To explore the generality of the method, symmetries ranging from C2 through C6 were designed. 96 designs were selected for experimental characterization, and 4 homodimers, 6 homotrimers, 6 homotetramers and 1 homopentamer were found to form stable monodisperse homooligomers in solution.

Computational Design

Existing methods for protein-protein docking fall into three general categories: (1) voxelized rigid representations with Fast Fourier Transform (FFT)-based docking, (2) docking based on patches of high-resolution local shape complementarity, and (3) Monte Carlo sampling with soft centroid models. The first two categories are not ideal for the protein design problem because the precise shape and chemical detail of the docked surfaces are unavailable, as the interface residues are not known in advance. The approach we take is one in which docked backbones are generated and then scored using a low-resolution representation of the proteins (requiring only the backbone coordinates and secondary structure assignments) but with two notable improvements. First, we employ a six-dimensional implicit side chain scoring methodology, which better predicts the result of subsequent full atom design calculation than a traditional coarse-grained model, and second, we use an enumerative strategy to generate docked backbones, which samples more robustly the low-dimensional docking space than a Monte Carlo search.

In past efforts, scoring at the docking stage has been accomplished using coarse-grained models in which the absent side chains are represented by one or two points in space, and the interaction potential between two amino acids is evaluated as a function of the distance or distances between these points, and in some cases an associated angle. These representations are incomplete since they do not capture the full six-dimensional rigid body relationship between pairs of side chains. To avoid loss of information, we have developed a Residue Pair Transform (RPX) model that represents the interaction between two residues by the full six dimensional rigid body transformation between their respective backbone N, Ca and C atoms. We employ a precompiled database of all favorable residue pair interactions found in structures from the Protein Data Bank involving alanine, isoleucine, leucine, valine, and methionine, binning these data based on the rigid body transform between amino acids. The score of a given docked configuration is the sum, over each pair of residues across the interface, of the lowest Rosetta full atom energy found in the associated spatial transformation bin of the database. This approach predicts the interface energy resulting from full atom sequence design calculation better than the Rosetta™ centroid energy function. As the residue-pair-transform database is compiled offline, arbitrary data selection (different subsets of amino acid identities) and processing (alternative smoothing and scoring schemes) can be employed with no impact on runtime of the docking calculations.

To best leverage the RPX scoring methodology described above, we employ deterministic sampling of the complete docking space. The configurational space for cyclic docking is four dimensional: the usual six degrees of freedom required for orienting a rigid body, minus translations along and rotations around the symmetry axis of the oligomer (to which the structure is invariant). These four degrees of freedom can be reduced effectively to three by the requirement that the subunits must be roughly in contact. We realize this dimensionality reduction using a fast slide-into-contact algorithm. To rapidly compute the translational distance along a slide vector, which will bring two rigid clouds of atoms into contact, we create a pair of two-dimensional arrays containing the leading face of each cloud along the slide vector. Corresponding cells of each array are checked, and the pair of atoms with least separation along the slide vectors defines an upper bound on the slide distance. The final slide distance is calculated using a local octree-like data structure (Methods). This results in a significant savings in the total number of samples that must be evaluated compared to a simpler brute force search.

In some examples, the slide vectors can be determined using a singular value decomposition (SVD) and/or the octree-like data structure can be a recursive structure used to divide 3-D spaces. In other examples, other data structures than slide vectors and/or octree-like data structures can be used in connection with other algorithms; e.g., stochastic Monte-Carlo based algorithms.

For the ten best RPX scoring docked arrangements of each monomer, low energy and shape complementary interfaces between protomers were generated using Rosetta™ sequence design calculations employing a Monte-Carlo simulated annealing protocol. Designs were filtered on number of mutations, buried surface area, shape complementarity and computed interaction energy, and 96 were selected for experimental characterization. The 11 dimers, 34 trimers, 19 tetramers, 17 pentamers and 15 hexamers are named according to the following nomenclature: the first 4 letters refer to the scaffold protein (as described in the supplementary information), the symmetry is denoted as Cn, and finally an integer is added to differentiate oligomers of identical symmetry and scaffold identity.

Protein Expression and Oligomerization State Screening

Synthetic genes encoding each of the 96 designs were synthesized and cloned into a vector with a T7 promoter system and either an N- or C-terminal (His)$_6$ tag, and the corresponding proteins expressed in $E.\ coli$. The proteins were purified by immobilized nickel-affinity chromatography (Ni$^{2+}$ IMAC) and size-exclusion chromatography (SEC). 64 designs were soluble and amenable to purification. The oligomerization states for 44 designs that eluted from SEC with a single predominant species were determined by size-exclusion chromatography in tandem with multi-angle light scattering (SEC-MALS). For 21 of the designs, the molecular weights determined by light scattering agreed with the designed oligomerization state.

Structural Characterization

To further assess the configuration of the designed proteins in solution, small-angle X-ray scattering (SAXS) measurements were performed on designs that had predominantly monodisperse traces in the SEC screen. A total of 26 designs (the 21 with consistent SEC-MALS data and 5 additional designs that had monodisperse SEC profiles) were characterized with this technique and the measured scattering profile was compared to that expected from the computational model. Designs with a deviation of less than or equal to 3.1 a.u. using the $\chi$ measure and a deviation of less than 11% between the computed and experimental radius of gyration were considered to be in the designed supramolecular arrangement (these thresholds were chosen based on the deviations between computed and measured values for designs with crystal structures consistent with the corresponding models; see below).

Of the 26 designs, 15 fulfill these criteria; 5 dimers, 6 trimers, 3 tetramers, and 1 pentamer. The docked configurations and designed interfaces of 13 of these are unique (three of the trimers have similar geometries with pairwise r.m.s.d. values between 1.9-2.5 Å; the lowest pairwise r.ms.d. among the remaining designs is 5.3 Å with no similarity in designed interface). Computational models, in silico symmetric docking energy landscapes, SEC-MALS chromatograms and SAXS experimental and computed profiles for the 30 designs are.

Crystal structures that contain the designed interface were obtained for five of the designed proteins: two dimers, two trimers and one tetramer, and are compared to the design models in FIG. 6. For each of the five cases the side chain rotamers of the hydrophobic residues are similar to those in the design model. The two dimers, ank3C2_1 and ank1C2_1, are both built from idealized ankyrin repeat proteins and are shown in FIGS. 6a and 6b. The ank3C2_1 design has a large hydrophobic patch (1100 Å$^2$) that is buried upon binding; all interface hydrophobic side chains are in the same rotameric state in the design model and the crystal structure with the exception of methionine 90 (FIG. 6a, right panel). The backbone r.m.s.d. between the design model and the crystal structure is 1.0 Å. The agreement between the model and the structure of ank1C2_1 (FIG. 6b) is even closer: both polar and hydrophobic side chain rotamers were correct and the r.m.s.d. to the model is only 0.9 Å.

The two trimeric designs with solved structures are 1na0C3_3 (FIG. 6c) built from a consensus designed tpr protein[16], and HR00C3_2 (FIG. 6d) built from a de novo designed repeat protein. 1na0C3_3 has a hydrophobic core that lies on the 3-fold axis formed by residues in all subunits. The r.m.s.d. between the crystal structure and design model is 1.0 Å. HR00C3_2 contains a pore on the symmetry axis and is stabilized by three separate heterologous interfaces. This trimer was designed using the computational model of a designed repeat protein whose structure had not previously been confirmed by X-ray crystallography. Thus the crystal structure, which has a backbone r.m.s.d. to the model of 0.9 Å, validates the design of both the monomer and oligomer simultaneously. This ability to accurately design higher order structures based on design models of monomers will considerably streamline future computational design of nanomaterials using monomers with custom designed properties.

For the two dimers and the two trimers, the $\chi$ values between the measured SAXS scattering profiles and the profiles computed from either the corresponding design models or crystal structures are less than 3.1. In contrast, the experimental SAXS data for the designed tetramer, ank1C4_2 (FIG. 6e), deviates considerably from that computed using the crystal structure (data not shown). The ank1C4_2 crystal structure adopts a C2 symmetric tetrameric structure in which 2 pairs of chains accurately match the design model (r.m.s.d. of 1.1 Å), but exhibit clear overall distortion relative to the C4 symmetric design model (r.m.s.d. of 4.5 Å). There are two distinct interfaces present in the structure, one of which corresponds to the designed interface. The experimental SAXS profile is closer to the design model of the tetramer than the crystal structure, and hence it seems likely that the symmetry breaking in the crystal is due to lattice contacts.

A sixth structure was solved for design ank4C4, which shows a single symmetric peak by SEC and forms a tetrameric complex in solution as determined by MALS. The SAXS profile of this design does not match that computed from the design model ($\chi$=3.8), and the crystal structure exhibits D2 symmetry rather than the target C4 symmetry. The SAXS profile computed from the D2 oligomer matches the measured scattering curve better than the target C4 model ($\chi$=1.2) indicating that the D2 state corresponds to the conformation of the design in solution (data not shown).

Subunit Extensions

Figure 7:
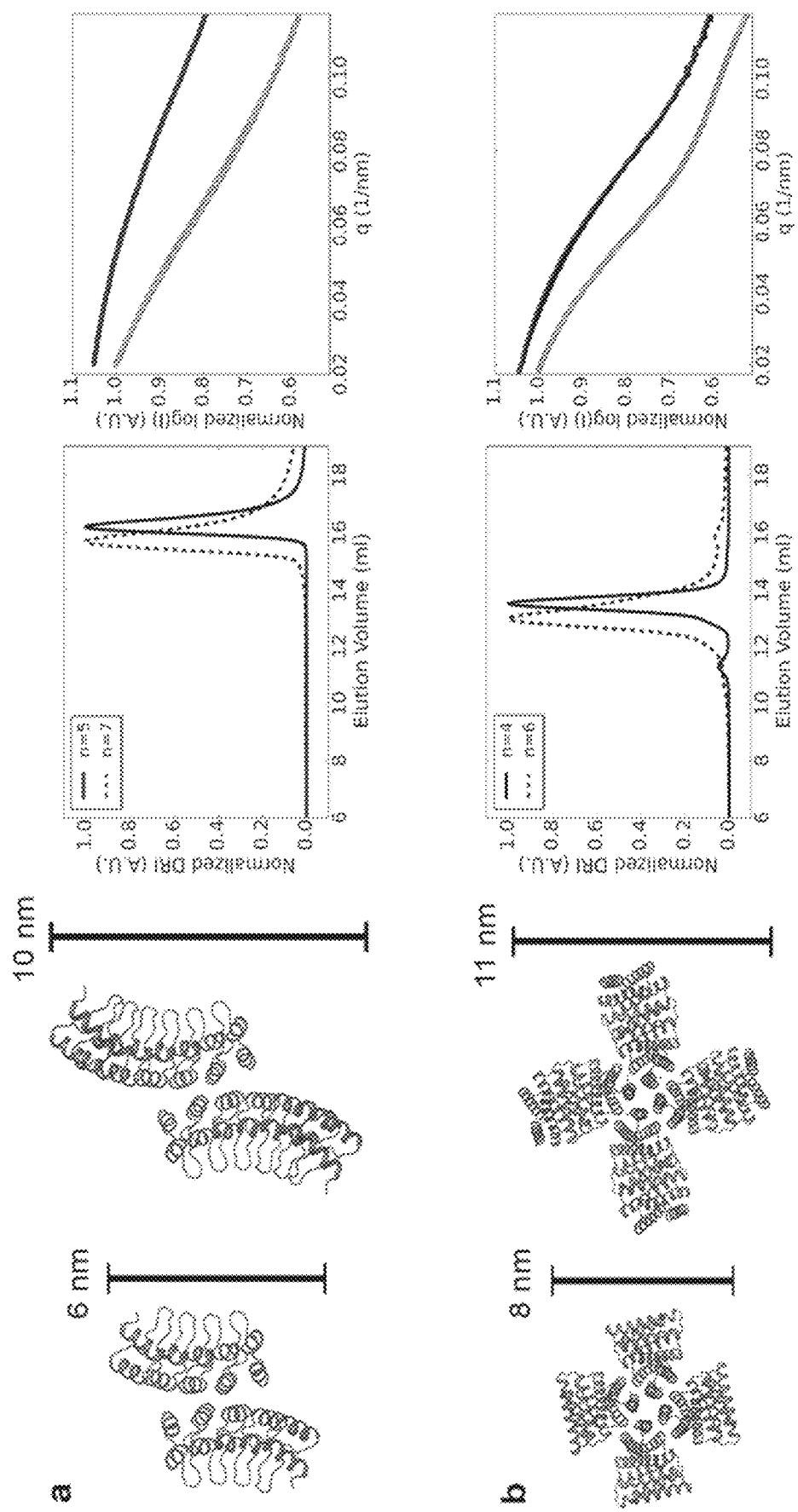
FIG. 7: Robustness of designs to subunit extension by repeat addition. From left to right: computational model of the original design, computational model of the extended design, SEC-MALS chromatogram used for molecular weight determination (n represents number of repeat modules in each monomer; original design: solid line; extended design: dotted line), SAXS scattering profiles (original design: experimental data in black circles, computed profile in red; extended design: experimental data open circles, computed profile in cyan). a, ank1C2_1. B, HR04C4_1.

To explore the modularity of the designs and the robustness of the designed interfaces, we extended two of the designed oligomers by appending two additional repeats to the original constructs. Extended versions of ank1C2_1 and HR04C4_1 were expressed and characterized as described above. SEC-MALS traces of the long constructs show the expected shifts to larger apparent sizes compared to the original constructs (FIG. 7, third column), and the calculated molecular weights are close to those expected. Experimental SAXS profiles of the extended designs are in good agreement with the extended computational models suggesting that the supramolecular arrangement of the subunits is maintained upon extending the scaffold protein. This ability to maintain oligomer geometry while extending the length of the monomers will be very useful for systematically varying the distance between binding moieties and for nanomaterial design.

Resilience to Guanidine Denaturation

The repeat protein scaffolds used to construct the designed oligomers are very stable proteins, and thus guanidine denaturation can be used to probe the stability of the designed interfaces independent of effects on the monomers. Four designed oligomers (one selected from each symmetry C2-C5) were purified in an initial round of IMAC and SEC, and subsequently run through SEC-MALS in TBS supplemented with 1M or 2M GuHCl. In both conditions, all four designs remained in their designed oligomeric state (as determined by MALS) without indications of smaller assembly formation (data not shown).

Discussion

Our results show that homo-oligomeric protein complexes with cyclic symmetry can be generated from repeat protein building blocks by computationally designing geometrically complementary, low-energy interfaces. A key advance is the new fast method for assessing designability that provides a reasonable estimate of the energy obtained after a full atom combinatorial sequence design calculation with roughly six orders of magnitude less computational cost. This allows exhaustive evaluation of the possible cyclically docked configurations of a monomer, which would not be possible with a combinatorial, all-atom sequence design calculation. The broad applicability of the computational pipeline developed here is highlighted by the number of successful designs (15) and symmetries (C2-C5). We have experimentally validated dimers, trimers, tetramers and pentamer—the broad range of structures and the variety of interface geometries and architectures far exceeds that reported in any previous study. The combination of RPX search for designable interfaces followed by Rosetta all atom design calculations can clearly generate a wide range of new interfaces involving three to five alpha helices; the ability of the approach to design new beta sheet and loop containing interfaces is an area for future investigation.

Progress in protein design will require study not only of the successes but also the failures. The results reported in this paper provide a valuable resource for understanding failure modes as the input scaffolds are all very stable designed proteins (in previous design studies, the often unknown stability of the starting native scaffolds and the robustness to amino acid substitutions were potentially confounding factors). We are able to distinguish distinct failure modes for the designs reported: 32 were not expressed solubly in E. Coli, 24 adopt multiple oligomerization states, 4 were monomeric, 15 were monodisperse but had an oligomerization state different from that designed, and 6 occupied the designed oligomerization state but had unanticipated configurations based on SAXS data. Analysis of the properties of the design models revealed that designs with (1) a high total charge (greater than −50), (2) small (under 750 Å$^2$) interfaces, (3) poor shape complementarity (sc<0.625), or (4) for which asymmetric pairwise docking calculations found much lower energy alternative arrangements than the two body interactions in the design model were generally unsuccessful. Furthermore, despite the success with HR00C3_2, designs based on monomers with crystal structures had higher success rates (19%) than those based on monomers validated only by SAXS (4%). The fraction of designs experimentally confirmed to be in the designed state increases from 15/96 in the overall population to 14/45 restricting to models that satisfy the above criteria (low electrostatic repulsion, larger shape complementary interfaces, absence of much lower energy competing dimeric states, and crystallographically validated monomer structures).

Our robust design pipeline can be combined with the modularity of computationally designed repeat proteins to control the three-dimensional arrangement of the protomers at multiple length scales. While the designed interfaces control the nanoscale three-dimensional arrangement, extensions of the repeat proteins allow for the placement of functional motifs with sub-nanometer resolution in each of the interacting proteins. Designed proteins can remain folded under strongly denaturing conditions, and the design process provides unparalleled control over their geometry and amino acid composition allowing for reactive chemical moieties, such as thiols or aromatic rings, to be reserved to engineer function in downstream applications. An immediate use for these designed oligomers is to probe how the geometry and valency of tethered signaling molecules affects the clustering of receptors and the cellular response. The relationship between ligand valency, spatial orientation, and signaling outcome is not well understood, and designed homoligomerization with systematically tunable lengths should be very well suited for investigating this and other basic biochemical questions.

Methods

Scaffold Set.

A set of 17 monomeric designed repeat proteins with high-resolution crystal structures as well as 6 computational models that were validated by SAXS were used as a scaffold set for our design protocol.

Motif Database and Scoring.

We construct Cartesian frames given two N-Cα-C backbone segments across the symmetric interface. The relative position and orientation of the two N—Cα-C segments form a six dimensional space that can be divided into bins, assigning to any possible position/orientation a bin index. The best-scoring, superimposable residue-pair available in a large database of candidates can then be found with a single memory lookup keyed on the bin index. The residue pair-motif database was constructed from residue pairs observed in a set of high quality structures from the Protein Data Bank (PDB), filtered for energetic favorability, separation by at least 10 residues in sequence, and residue composition of only alanine, isoleucine, leucine, valine, and methionine. To compute an aggregate score for each conformation, we consider all pairs of N—Cα-C backbone segments across the newly formed symmetric interface within 9 Å of one another. For each such pair, the score of the best superimposable residue pair motif is looked up, and the results are summed.

The bin index is based on the concept that a space of all rigid body transformations, as long as objects are closer than some maximum distance, is actually a finite 6D manifold. In one example, six coordinates are chosen that can be used to unequivocally map any point in the manifold, where the six coordinates include a 3D vector (x y z) for the relative translation and a pseudo-vector (a b g) of 3 Euler angles for the relative rotation. Other coordinates/parameters are possible as well. A grid is then placed on the 6D space to produce the bins. Each bin is assigned a unique index in the form of a 64 bit integer. When evaluating a pose, or a pair of proteins with a symmetric configuration, for docking, a relative transformation between pairs of amino acids that are interacting across the interface of the monomer pair and the respective 6d pseudo-vector (x1 y1 z1 a1 b1 g1) along with its bin index is calculated. This bin index allows us to check the content of a hash value that is filled prior to the docking calculation by collecting favorable interactions that are observed in natural proteins that have the same rigid body transformation and therefore the same bin index.

The above-mentioned hash value is determined using a hash function or hash transform. The hash function/hash transform can receive backbone atom positions of both residues as inputs, computes their relative rigid body transformation and returns the bin index as mentioned above. The keys are integer values (e.g., 16 bit integers, 32 bit integers, 64 bit integers, 128 bit integers, 256 bit integers, etc.) that are assigned when the hash is initially constructed prior to the docking calculation. In the hash function, data for at least three atoms for each residue are used (e.g., N, Cα, C) to construct a local orthonormal frame which encodes the geometric information regarding the position and orientation of each amino acid in the pair.

Cyclic Docking.

To generate cyclic homooligomeric arrangements of n copies of a protein monomer, we center it at the origin, finely sample the 3 rotational degrees of freedom, generate a symmetric copy by (360/n)° rotation around the Z-axis, and slide the two bodies into contact along the X-axis allowing a small range of X offsets close to the contact value. For each of these, the axis of symmetry is determined from the relative orientation of the two subunits, and the full oligomer is generated and evaluated using the residue pair motif database. A rapid slide into contact operation is required for this sampling strategy. Computing the slide distance along a given slide vector is accomplished using two two-dimensional arrays perpendicular to the slide direction into which the atoms along the leading face of each body are placed. Corresponding cells are checked, and the pair with the least separation provides an estimate of the slide distance. The bodies are placed according to this estimate, but may still have clashes. All contacting pairs of atoms across the bodies are checked using an octree-like data structure, and the bodies are backed off so as to relieve the largest clash found. This process is repeated until no clashes are found. In practice, only one or two iterations through the fast clash check are required in most cases, making the slide move rapid.

Interface Design.

An interface design protocol was implemented in RosettaScripts™ and is described briefly here. In each design trajectory, the protomer was initially perturbed by a small translation perpendicular to the axis of symmetry, as well as a random rotation around its center of mass. An oligomer with the specified cyclic symmetry was then generated using the information stored in the symmetry definition file. Amino acids at the interface were optimized using the Monte-Carlo simulated annealing protocol available in the Rosetta™ Macromolecular Modeling suite. An initial optimization step was executed with a modified score function with a soft repulsive term. Once a sequence was converged upon, designable positions were allowed to minimize side chain torsion angles using the same reduced repulsive term weight. A subsequent round of design and minimization was conducted, but with the standard score function in order to obtain a sequence that corresponds to a local minimum of the energy function. Initially, the extended rotamer library available in Rosetta™ was utilized but in later design rounds it was augmented with the rotamers available in the residue pair motif database. Individual design trajectories were filtered by the following criteria: difference between Rosetta energy of bound (oligomeric) and unbound (monomeric) states less than −20.0 Rosetta energy units, interface surface area greater than 700 Å$^2$, Rosetta shape complementarity greater than 0.65, and less than 45 mutations made from the respective native scaffold. Designs that passed these criteria were manually inspected and refined by single point reversions for mutations that were deemed as not contributing to stabilizing the bound state of the interface. The design with the best overall scores for each docked configuration was then added to a set of finalized proteins to be experimentally validated.

Size Exclusion Chromatography.

Elution samples for each designed protein were concentrated down using a 10,000 MWCO protein concentrator (Novagen) and fractionated by size on an AKTA pure chromatography system using a Superdex™ 200 10/300 GL gel filtration column (GE Life Sciences) in 25 mM Tris 150 mM Nacl pH 8 (TBS) unless otherwise. Sizing profiles were noted based on absorption at 220 nm and 280 nm wavelength light for each fraction. Molecular weights for predominant species in each protein trace were estimated by comparison to the corresponding monomeric profile.

Protein Expression and Purification.

Synthetic genes for these designed proteins were optimized for *E. coli* expression and assembled from purchased genes (Genscript) ligated into the pET21-NESG vector at restriction sites NdeI and XhoI. These plasmids were cloned into BL21 (DE3) *E. coli* competent cells. Transformants were inoculated and grown in either LB or TB medium with either 100 mg L$^{-1}$ carbenicillin or 150 mg L$^{-1}$ ampicillin at 37° C. until an OD$_{600}$ of 0.7. Isopropyl-thio-β-D-galactopyranoside was then added at a concentration of 1 mM to induce protein expression. Expression proceeded for 20 hours at 18° C. until the cell cultures were harvested by centrifugation. Cell pellets were resuspended in TBS and lysed by sonication. Each filtered lysate was then purified by Ni$^{2+}$ immobilized metal affinity chromatography with Ni-NTA Superflow™ resin (Qiagen). Resin with bound cell lysate was washed with five column volumes of 25 mM imidazole and five column volumes of 50 mM imidazole. The desired proteins were then eluted with five column volumes of 400 mM imidazole and further purified by size exclusion chromatography.

Size Exclusion Chromatography with Multi-Angle Light Scattering.

Fractions containing single predominant species from the initial round of size exclusion chromatography were concentrated down with 10,000 MWCO protein concentrators (Novagen) to a concentration of 1.0-2.0 mg mL$^{-1}$. 100 uL of each sample was then run through a high-performance liquid chromatography system (Agilent) using (unless otherwise noted) a Superdex 200 10/300 GL gel filtration column (GE Life Sciences) at an elution rate of 0.50 mL min$^{-1}$ in TBS. These fractionation runs were coupled to a multi-angle light scattering detector (Wyatt) in order to determine the absolute molecular weights for each designed protein. The following equation[1] derived from the Rayleigh-Debye-Gans theory of light scattering[2] was used in the ASTRA software to calculate the molecular weight of the major species present in each sample:

$$\frac{K^*c}{R(\theta, c)} = \frac{1}{M_w P(\theta)} + 2A_2c$$

where:
R(θ,c) is the excess Rayleigh ratio of the solution as a function of scattering angle θ and concentration c. It is directly proportional to the intensity of the scattered light in excess of the light scattered by the pure solvent.
c is the solute concentration.
$M_w$ is the weight-averaged solute molar mass.
$A_2$ is the second virial coefficient in the virial expansion of the osmotic pressure.
K* is the constant $4\pi^2(dn/dc)^2 n_0^2/N_a \lambda_0^4$.
$N_a$ is Avogadro's number. This number always appears when concentration is measured in g/mL and molar mass in g/mol.
P(θ) describes the angular dependence of the scattered light, and can be related to the rms radius.
$n_0$ is the index of refraction of the solvent
$\lambda_0$ is the vacuum wavelength of the laser Accounting for error in light scattering data acquisition, species with calculated molecular weights within 13% of the expected target molecular weight for each design were considered to be forming the anticipated oligomeric state.

Small-Angle X-Ray Scattering.

Designed proteins that predominantly formed the target oligomeric species were re-expressed and purified for low-resolution structure determination while in solution by small-angle X-ray scattering (SAXS). A purified elution sample and concentrated sample of each protein were sent for data collection at the SIBYLS High Throughput SAXS Advanced Light Source in Berkeley, Calif. A beam exposure time of between 0.5-2.0 seconds was used to obtain diffraction data, which we represent in plots of log intensity (I) vs. q.
where:
$q=(4\pi \sin \theta)/\lambda$
2θ is angle of diffraction from detector origin
λ is wavelength of the incident X-ray beam
Experimental diffraction data was then analyzed with the java-based application, Scatter. Minimum q values ($q_{min}$) and experimental radii of gyration (Rg) were determined by Guinier analysis. Data resolution, reflected by maximum q value ($q_{max}$), was determined by a characteristic asymptote in signal intensity described by Porod's Law. Refined data sets and corresponding designed model .pdb files were input to the FoXS web server to compute the agreement (evaluated as X) between the experimental and model-computed profiles[6].

Generation of Extension Ensemble and Determination of SAXS-Suggested Model.

A set of designed homooligomers, one each of C2 and C4 symmetry, that had been structurally validated by X-ray diffraction crystallography and/or SAXS were selected as candidates for extension. Because the repeating units of the initial scaffolds were not perfectly superimposable, each unique repeat unit (aside from N- and C-capping repeats) was propagated to generate several models with two additional repeat units (three for C2 oligomer, two for C4 oligomer). 100 trajectories of a Rosetta™ protocol that previously showed to conformationally sample the local energy landscape was then performed on each extended model. The total extension set was then input to FoXS with an experimentally-obtained profile to determine an ensemble of models that agreed within a threshold to the data.

Crystallography, Data Acquisition, Structure Determination and Refinement.

Selected designs were expressed as above and purified by IMAC and SEC on a Superdex™ 200 10/300 GL gel filtration column using a buffer containing 25 mM Tris pH 8.0 and 50 mM NaCl. Fractions corresponding to the designed oligomers were combined and concentrated for screening.

Crystallization trials for ank3C2_1 were performed at 16.5 mg/ml. The protein crystallized readily in a variety of conditions and optimization was performed using 100 mM Tris pH 8.5, 200 mM magnesium chloride and 30% (v/v) PEG 400. Initial crystallization for 1naOC3_3 trials were performed at 15 mg/ml and produced crystals in 2.4 M sodium malonate pH 7.0 that did not yield a diffraction pattern. Upon concentration crystals that diffracted up to 2.1 Angstroms grew in 2 months. Crystallization trials for ank1C4_2 were performed at 12 mg/ml and pyramidal crystals were observed within 2 weeks in 100 mM sodium acetate pH 4.6 and 2.0 M ammonium sulfate. Diffraction data were collected at Advanced Photon Source at Argonne National Laboratory in Lemont, Ill. Data reduction was carried out using XDS/SCALE™. Molecular Replacement was performed in the program PHASER™ using the design models as search models. Solutions were refined using the program PHENIX™ or BUSTER™. MR solutions were initially subjected to rigid body refinement and subsequently coordinate refinement. Individual atomic displacement parameter (ADP) refinement and automated water picking were also performed. Refinement protocols were run iteratively while the quality of the model was assessed by the R/R-free values. Finally, alternating cycles of refinement and model building in COOT were performed using the using the 2mFo-DFc map to obtain the final coordinates[12].

HR00C3_2 and ank1C2_1 were dialyzed against 25 mM Tris buffer pH 8.0 and 150 mM NaCl. The final concentration of HR00C3_2 and ank1C2_1 used for crystallization trials were 12 mg ml[-1]. The HR00C3_2 and ank1C2_1 protein were screened with a Phoenix Robot (Art Robbins Instruments) using the following crystallization screens: Crystal Screen, Natrix, PEG/Ion, Index and PEGRx (Hampton Research, Aliso Viejo, Calif.) and Berkeley Screen (Lawrence Berkeley National Laboratory). Crystals of HR00C3_2 and ank1C2_1 were found in Berkeley Screen conditions. HR00C3_2 was found in condition of 0.3 M Sodium Citrate, 0.1 M Hepes pH 7.5 and 15% PEG 3,350 and ank1C2_1 was found in 0.4 M Sodium Chloride, 0.1 M Tris-HCl pH 8.5 and 30% PEG 3,350. HR00C3_2 and ank1C2_1 crystals were obtained after 4 days by the sitting-drop vapor-diffusion method with the drops consisting of a mixture of 0.2 μl of protein solution and 0.2 μl of reservoir solution. Crystallization trials for ank4C4 were performed with a stock protein concentration of 15 mg/ml with three sample to condition ratios in the following crystallization screens: PEG/Ion, Index (Hampton Research, Aliso Viejo, Calif.), Morpheus (Molecular Dimensions). Hanging-drop optimization was performed with an evenly distributed pH and concentration gradient, and the protein produced crystals within 3 days in a mixture of 1 μl protein solution and 1 μl reservoir solution of 2.1 M DL-Malic Acid pH 7.0. Diffraction data were collected at Advanced Light Source (at Beamline 8.2.1) at Lawrence Berkeley National Laboratory in Berkeley, Calif. Integration, scaling and merging of the X-ray diffraction data were carried out with the HKL2000 package[13]. An analysis of the intensity statistics carried out on HR00C3_2 by Phenix xtriage program indicated that the data was merohedrally twinned with twin law (-h, -k, l) with an estimated twin fraction of 46%. Molecular replacement was carried out using PHASER™ in PHENIX™ suite (using a monomer predicted by Rosetta ab initio structure prediction as the initial search model. Refinement was carried out with phenix.refine, using a twin-based target for HR00C3_2 and a maximum likelihood target for ANK1C2-G3ank1C2_1. Reciprocal space refinement was complemented by rounds of manual model adjustment in COOT™. Root-mean-square deviation differences from ideal geometries for bond lengths, angles and dihedrals were calculated with Phenix™. The overall stereochemical quality of all final models was assessed using the program MOLPROBITYPRO™

REFERENCES

1 Ali, M. H. & Imperiali, B. Protein oligomerization: How and why. *Bioorganic & Medicinal Chemistry* 13, 5013-5020, doi:10.1016/j.bmc.2005.05.037 (2005).

2 Goodsell, D. S. & Olson, A. J. Structural symmetry and protein function. *Annual Review of Biophysics and Biomolecular Structure* 29, 105-153, doi:10.1146/annurev.biophys.29.1.105 (2000).

3 Nishi, H., Hashimoto, K., Madej, T. & Panchenko, A. R. Evolutionary, Physicochemical, and Functional Mechanisms of Protein Homooligomerization. *Oligomerization in Health and Disease* 117, 3-24, doi:10.1016/b978-0-12-386931-9.00001-5 (2013).

4 Fletcher, J. M. et al. A Basis Set of de Novo Coiled-Coil Peptide Oligomers for Rational Protein Design and Synthetic Biology. *Acs Synthetic Biology* 1, 240-250, doi:10.1021/sb300028q (2012).

5. Smock, R. G., Yadid, I., Dym, O., Clarke, J. & Tawfik, D. S. De Novo Evolutionary Emergence of a Symmetrical Protein Is Shaped by Folding Constraints. *Cell* 164, 476-486, doi:10.1016/j.cell.2015.12.024 (2016).
6. Voet, A. R. D., Nogushi, H., Addy, C., Simoncini, D., Terada, D., Unzai, S., Park, S.-Y., Zhang, K. Y. J. and Tame, J. R. H. Computational Design of a Self-assembling Symmetrical β-propeller protein. *PNAS* 111, 15102-15107, doi:10.1073/pnas.1412768111 (2014).
7. Stranges, P. B., Machius, M., Miley, M. J., Tripathy, A. & Kuhlman, B. Computational design of a Symmetric Homodimer Using Beta-strand Assembly. *Proceedings of the National Academy of Sciences of the United States of America* 108, 20562-20567, doi:10.1073/pnas.1115124108 (2011).
8. Der, B. S. et al. Metal-Mediated Affinity and Orientation Specificity in a Computationally Designed Protein Homodimer. *Journal of the American Chemical Society* 134, 375-385, doi:10.1021/ja208015j (2012).
9. Mou, Y., Huang, P. S., Hsu, F. C., Huang, S. J. & Mayo, S. L. Computational Design and Experimental Verification of a Symmetric Protein Homodimer. *Proceedings of the National Academy of Sciences of the United States of America* 112, 10714-10719, doi:10.1073/pnas.1505072112 (2015).
10. Huang, P. S. et al. De novo Design of an Ideal TIM-barrel Scaffold. *Protein Science* 24, 186-186 (2015).
11. Lin, Y.-R. et al. Control Over Overall Shape and Size in de novo Designed Proteins. *Proceedings of the National Academy of Sciences of the United States of America* 112, E5478-E5485, doi:10.1073/pnas.1509508112 (2015).
12. Koga, N. et al. Principles for Designing Ideal Protein Structures. *Nature* 491, 222-227, doi:10.1038/nature11600 (2012).
13. Parmeggiani, F. et al. A General Computational Approach for Repeat Protein Design. *Journal of Molecular Biology* 427, 563-575, doi:10.1016/j.jmb.2014.11.005 (2015).
14. Huang, P.-S. et al. High Thermodynamic Stability of Parametrically Designed Helical Bundles. *Science* 346, 481-485, doi:10.1126/science. 1257481 (2014).
15. Brunette, T. J. et al. Exploring the Repeat Protein Universe through Computational Protein Design. *Nature*, doi:10.1038/nature16162 (2015).
16. Main, E. R. G., Xiong, Y., Cocco, M. J., D'Andrea, L. & Regan, L. Design of Stable Alpha-helical arrays from an Idealized TPR Motif. *Structure* 11, 497-508, doi:10.1016/s0969-2126(03)00076-5 (2003).
17. Pechmann, S., Levy, E. D., Tartaglia, G. G. & Vendruscolo, M. Physicochemical Principles that Regulate the Competition between Functional and Dysfunctional Association of Proteins. *Proceedings of the National Academy of Sciences of the United States of America* 106, 10159-10164, doi:10.1073/pnas.0812414106 (2009).
18. Levy, E. D. & Teichmann, S. Structural, Evolutionary, and Assembly Principles of Protein Oligomerization. *Oligomerization in Health and Disease* 117, 25-51, doi:10.1016/b978-0-12-386931-9.00002-7 (2013).
19. Bahadur, R. P., Chakrabarti, P., Rodier, F. & Janin, J. Dissecting Subunit Interfaces in Homodimeric Proteins. *Proteins-Structure Function and Bioinformatics* 53, 708-719, doi:10.1002/prot.10461 (2003).
20. Bahadur, R. P., Chakrabarti, P., Rodier, F. & Janin, J. A Dissection of Specific and Non-specific Protein-Protein Interfaces. *Journal of Molecular Biology* 336, 943-955, doi:10.1016/j.jmb.2003.12.073 (2004).
21. Janin, J., Bahadur, R. P. & Chakrabarti, P. Protein-protein Interaction and Quaternary Structure. *Quarterly Reviews of Biophysics* 41, 133-180, doi:10.1017/s0033583508004708 (2008).
22. Leaver-Fay, A. et al. in *Methods in Enzymology*, Vol 487: *Computer Methods, Pt C Methods in Enzymology* 545-574 (Elsevier Academic Press Inc, 2011).
23. Chen, R. & Weng, Z. P. Docking Unbound Proteins Using Shape Complementarity, Desolvation, and Electrostatics. *Proteins-Structure Function and Genetics* 47, 281-294, doi:10.1002/prot.10092 (2002).
24. Pierce, B., Tong, W. W. & Weng, Z. P. M-ZDOCK: a Grid-based Approach for C-n Symmetric Multimer Docking. *Bioinformatics* 21, 1472-1478, doi:10.1093/bioinformatics/bti229 (2005).
25. Schneidman-Duhovny, D., Inbar, Y., Nussinov, R. & Wolfson, H. J. PatchDock and SymmDock: Servers for Rigid and Symmetric docking. *Nucleic Acids Research* 33, W363-W367, doi:10.1093/nar/gki481 (2005).
26. Gray, J. J. & Baker, D. Protein-protein Docking Predictions with RosettaDock. *Biophysical Journal* 86, 306A-306A (2004).
27. Gray, J. J. et al. Protein-protein Docking with Simultaneous Optimization of Rigid-body Displacement and Side-chain Conformations. *Journal of Molecular Biology* 331, 281-299, doi:10.1016/s0022-2836(03)00670-3 (2003).
28. Wei, H. et al. Lysozyme-stabilized gold fluorescent cluster: Synthesis and Application as Hg2+ Sensor. *Analyst* 135, 1406-1410, doi:10.1039/c0an00046a (2010).
29. Lu, M., Dousis, A. D. & Ma, J. OPUS-PSP: An Orientation-dependent Statistical All-atom Potential Derived from Side-chain Packing. *Journal of Molecular Biology* 376, 288-301, doi:10.1016/j.jmb.2007.11.033 (2008).
30. Zheng, W. H., Schafer, N. P., Davtyan, A., Papoian, G. A. & Wolynes, P. G. Predictive Energy Landscapes for Protein-protein Association. *Proceedings of the National Academy of Sciences of the United States of America* 109, 19244-19249, doi:10.1073/pnas.1216215109 (2012).
31. DeBartolo, J., Dutta, S., Reich, L. & Keating, A. E. Predictive Bcl-2 Family Binding Models Rooted in Experiment or Structure. *Journal of Molecular Biology* 422, 124-144, doi:10.1016/j.jmb.2012.05.022 (2012).
32. Fleishman, S. J. et al. RosettaScripts: A Scripting Language Interface to the Rosetta Macromolecular Modeling Suite. *Plos One* 6, doi:10.1371/journal.pone.0020161 (2011).
33. Schneidman-Duhovny, D., Hammel, M. & Sali, A. FoXS: a Web server for Rapid Computation and Fitting of SAXS Profiles. *Nucleic Acids Research* 38, W540-W544, doi:10.1093/nar/gkq461 (2010).
34. Boyken, S. E. et al. De novo Design of Protein Homooligomers with Modular Hydrogen-Bond Network-mediated Specificity. *Science* 352, 680-687, doi:10.1126/science.aad8865 (2016).
35. Park, K. et al. Control of Repeat-protein Curvature by Computational Protein Design. *Nature Structural & Molecular Biology* 22, 167-174, doi:10.1038/nsmb.2938 (2015).

We claim:

1. An isolated polypeptide comprising the amino acid sequence that has at least 70% sequence identity to the amino acid sequence of SEQ ID NO: 40, wherein the polypeptide is capable of self-assembly into homo-oligomers.

2. The isolated polypeptide of claim 1, wherein the polypeptide comprises the amino acid sequence having at least 75% sequence identity to the amino acid sequence of SEQ ID NO: 40.

3. The isolated polypeptide of claim 1, wherein the polypeptide comprises the amino acid sequence having at least 90% sequence identity to the amino acid sequence of SEQ ID NO: 40.

4. The isolated polypeptide of claim 1, wherein the polypeptide comprises the amino acid sequence having at least 95% sequence identity to the amino acid sequence of SEQ ID NO: 40.

5. The isolated polypeptide of claim 1, wherein the polypeptide comprises the amino acid sequence having at least 98% sequence identity to the amino acid sequence of SEQ ID NO: 40.

6. The polypeptide of claim 1, wherein the polypeptide comprises the amino acid sequence selected from the group consisting of SEQ ID NOS: 16-21, 34-35, 37, and 40.

7. The isolated polypeptide of claim 1, wherein the polypeptide comprises the amino acid sequence of SEQ ID NO: 40.

8. The isolated polypeptide of claim 1, wherein residues in bold font for SEQ ID NO: 40 are conserved in the polypeptide EEAELAYLLGELAYKLGEYRIAIRAYRIALKRDPNNAEAWYNLGNAYYKQGRYREAIEYYQKAL ELDPNNAEAWYNLGNAYYERGEYEEAIEYYRKALRLDPNNADAMQNLLNAKMREE (SEQ ID NO: 40).

9. An isolated polypeptide homo-oligomer comprising a plurality of polypeptides according to claim 8.

10. The isolated polypeptide homo-oligomer of claim 9, further comprising a plurality of polypeptides having at least 97% sequence identity to the amino acid sequence of SEQ ID NO: 39.

11. An isolated polypeptide homo-oligomer comprising a plurality of polypeptides according to claim 1.

12. The isolated polypeptide homo-oligomer of claim 11, further comprising a plurality of polypeptides having at least 97% sequence identity to the amino acid sequence of SEQ ID NO: 39.

13. The isolated polypeptide oligomer of claim 12, wherein residues in bold font for SEQ ID NO: 39 are conserved

```
                                    (SEQ ID NO: 39)
KYDGSKLRIGILHARWNAEIILALVLGALKRLQEFGVKRENIIIETVPGSF

ELPYGSKLFVEKQKRLGKPLDAIIPIGVLIKGSTMHFEYICDSTTHQLMKL

NFELGIPVIFGVLTCLTDEQAEARAGLIEGKMHNHGEDWGAAAVEMATKF

N.
```

* * * * *

SEQUENCE LISTING

<160> NUMBER OF SEQ ID NOS: 41

<210> SEQ ID NO 1
<211> LENGTH: 31
<212> TYPE: PRT
<213> ORGANISM: Artificial Sequence
<220> FEATURE:
<223> OTHER INFORMATION: Synthetic

<400> SEQUENCE: 1

Ser Glu Leu Gly Lys Arg Leu Ile Glu Ala Ala Glu Asn Gly Asn Lys
1               5                   10                  15

Asp Arg Val Lys Asp Leu Leu Glu Asn Gly Ala Asp Val Asn Ala
            20                  25                  30

<210> SEQ ID NO 2
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: X is I or L
<220> FEATURE:
<221> NAME/KEY: MISC_FEATURE
<222> LOCATION: (27)..(27)
<223> OTHER INFORMATION: X is K or Q
<220> FEATURE:
<221> NAME/KEY: MISC_FEATURE
<222> LOCATION: (29)..(29)
<223> OTHER INFORMATION: X is D or A
<220> FEATURE:
<221> NAME/KEY: MISC_FEATURE
<222> LOCATION: (30)..(30)
<223> OTHER INFORMATION: X is P or D
<220> FEATURE:
<221> NAME/KEY: MISC_FEATURE
<222> LOCATION: (31)..(31)
<223> OTHER INFORMATION: X is P, V or N
<220> FEATURE:
<221> NAME/KEY: MISC_FEATURE
<222> LOCATION: (32)..(32)
<223> OTHER INFORMATION: X is T or N
<220> FEATURE:
<221> NAME/KEY: MISC_FEATURE
<222> LOCATION: (33)..(33)
<223> OTHER INFORMATION: X is T, A or S

<400> SEQUENCE: 2

Ser Asp Ser Asp Gly Lys Thr Pro Leu His Leu Ala Ala Glu Asn Gly
1               5                   10                  15

His Lys Glu Val Val Lys Leu Leu Xaa Ser Xaa Gly Xaa Xaa Xaa Xaa
            20                  25                  30

Xaa

<210> SEQ ID NO 3
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is V or I

<400> SEQUENCE: 3

Ser Asp Ser Asp Gly Arg Thr Pro Leu Asp Leu Ala Arg Glu His Gly

```
                 1               5                  10                 15
Asn Glu Glu Xaa Val Lys Leu Leu Glu Lys Gln
              20                  25

<210> SEQ ID NO 4
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (56)..(56)
<223> OTHER INFORMATION: X is I or L
<220> FEATURE:
<221> NAME/KEY: MISC_FEATURE
<222> LOCATION: (58)..(58)
<223> OTHER INFORMATION: X is Q or K
<220> FEATURE:
<221> NAME/KEY: MISC_FEATURE
<222> LOCATION: (60)..(60)
<223> OTHER INFORMATION: X is D or A
<220> FEATURE:
<221> NAME/KEY: MISC_FEATURE
<222> LOCATION: (61)..(61)
<223> OTHER INFORMATION: X is D or P
<220> FEATURE:
<221> NAME/KEY: MISC_FEATURE
<222> LOCATION: (62)..(62)
<223> OTHER INFORMATION: X is V, N or P
<220> FEATURE:
<221> NAME/KEY: MISC_FEATURE
<222> LOCATION: (63)..(63)
<223> OTHER INFORMATION: X is N or T
<220> FEATURE:
<221> NAME/KEY: MISC_FEATURE
<222> LOCATION: (64)..(64)
<223> OTHER INFORMATION: X is A, S or T
<220> FEATURE:
<221> NAME/KEY: MISC_FEATURE
<222> LOCATION: (65)..(65)
<223> OTHER INFORMATION: X is S or K
<220> FEATURE:
<221> NAME/KEY: MISC_FEATURE
<222> LOCATION: (70)..(70)
<223> OTHER INFORMATION: X is R or K
<220> FEATURE:
<221> NAME/KEY: MISC_FEATURE
<222> LOCATION: (75)..(75)
<223> OTHER INFORMATION: X is H, L or Y
<220> FEATURE:
<221> NAME/KEY: MISC_FEATURE
<222> LOCATION: (84)..(84)
<223> OTHER INFORMATION: X is V or I
<220> FEATURE:
<221> NAME/KEY: MISC_FEATURE
<222> LOCATION: (89)..(89)
<223> OTHER INFORMATION: X is L or I
<220> FEATURE:
<221> NAME/KEY: MISC_FEATURE
<222> LOCATION: (91)..(91)
<223> OTHER INFORMATION: X is Q or K
<220> FEATURE:
<221> NAME/KEY: MISC_FEATURE
<222> LOCATION: (93)..(93)
<223> OTHER INFORMATION: X is D or A
<220> FEATURE:
<221> NAME/KEY: MISC_FEATURE
<222> LOCATION: (94)..(94)
<223> OTHER INFORMATION: X is D or P
<220> FEATURE:
<221> NAME/KEY: MISC_FEATURE
<222> LOCATION: (95)..(95)
<223> OTHER INFORMATION: X is N, V or P
<220> FEATURE:
<221> NAME/KEY: MISC_FEATURE
<222> LOCATION: (96)..(96)
```

```
<223> OTHER INFORMATION: X is N or T
<220> FEATURE:
<221> NAME/KEY: MISC_FEATURE
<222> LOCATION: (97)..(97)
<223> OTHER INFORMATION: X is A, S or T
<220> FEATURE:
<221> NAME/KEY: MISC_FEATURE
<222> LOCATION: (98)..(98)
<223> OTHER INFORMATION: X is S or K
<220> FEATURE:
<221> NAME/KEY: MISC_FEATURE
<222> LOCATION: (103)..(103)
<223> OTHER INFORMATION: X is R or K
<220> FEATURE:
<221> NAME/KEY: MISC_FEATURE
<222> LOCATION: (108)..(108)
<223> OTHER INFORMATION: X is H, L or Y
<220> FEATURE:
<221> NAME/KEY: MISC_FEATURE
<222> LOCATION: (117)..(117)
<223> OTHER INFORMATION: X is V or I
<220> FEATURE:
<221> NAME/KEY: MISC_FEATURE
<222> LOCATION: (122)..(122)
<223> OTHER INFORMATION: X is L or I
<220> FEATURE:
<221> NAME/KEY: MISC_FEATURE
<222> LOCATION: (124)..(124)
<223> OTHER INFORMATION: X is Q or K
<220> FEATURE:
<221> NAME/KEY: MISC_FEATURE
<222> LOCATION: (126)..(126)
<223> OTHER INFORMATION: X is D or A
<220> FEATURE:
<221> NAME/KEY: MISC_FEATURE
<222> LOCATION: (127)..(127)
<223> OTHER INFORMATION: X is D or P
<220> FEATURE:
<221> NAME/KEY: MISC_FEATURE
<222> LOCATION: (128)..(128)
<223> OTHER INFORMATION: X is V, N or P
<220> FEATURE:
<221> NAME/KEY: MISC_FEATURE
<222> LOCATION: (129)..(129)
<223> OTHER INFORMATION: X is N or T
<220> FEATURE:
<221> NAME/KEY: MISC_FEATURE
<222> LOCATION: (130)..(130)
<223> OTHER INFORMATION: X is A, S or T
<220> FEATURE:
<221> NAME/KEY: MISC_FEATURE
<222> LOCATION: (150)..(150)
<223> OTHER INFORMATION: X is V or I

<400> SEQUENCE: 4

Ser Glu Leu Gly Lys Arg Leu Ile Glu Ala Ala Glu Asn Gly Asn Lys
1               5                   10                  15

Asp Arg Val Lys Asp Leu Leu Glu Asn Gly Ala Asp Val Asn Ala Ser
                20                  25                  30

Asp Ser Asp Gly Lys Thr Pro Leu His Leu Ala Ala Glu Asn Gly His
            35                  40                  45

Lys Glu Val Val Lys Leu Leu Xaa Ser Xaa Gly Xaa Xaa Xaa Xaa Xaa
        50                  55                  60

Xaa Asp Ser Asp Gly Xaa Thr Pro Leu His Xaa Ala Ala Glu Asn Gly
65                  70                  75                  80

His Lys Glu Xaa Val Lys Leu Leu Xaa Ser Xaa Gly Xaa Xaa Xaa Xaa
                85                  90                  95

Xaa Xaa Asp Ser Asp Gly Xaa Thr Pro Leu His Xaa Ala Ala Glu Asn
            100                 105                 110

Gly His Lys Glu Xaa Val Lys Leu Leu Xaa Ser Xaa Gly Xaa Xaa Xaa
        115                 120                 125
```

```
Xaa Xaa Ser Asp Ser Asp Gly Arg Thr Pro Leu Asp Leu Ala Arg Glu
        130                 135                 140

His Gly Asn Glu Glu Xaa Val Lys Leu Leu Glu Lys Gln
145                 150                 155

<210> SEQ ID NO 5
<211> LENGTH: 157
<212> TYPE: PRT
<213> ORGANISM: Artificial Sequence
<220> FEATURE:
<223> OTHER INFORMATION: Synthetic

<400> SEQUENCE: 5

Ser Glu Leu Gly Lys Arg Leu Ile Glu Ala Ala Glu Asn Gly Asn Lys
1               5                   10                  15

Asp Arg Val Lys Asp Leu Ile Glu Asn Gly Ala Asp Val Asn Ala Ser
            20                  25                  30

Asp Ser Asp Gly Arg Thr Pro Leu His His Ala Ala Glu Asn Gly His
        35                  40                  45

Lys Glu Val Val Lys Leu Leu Ile Ser Lys Gly Ala Asp Val Asn Ala
50                  55                  60

Lys Asp Ser Asp Gly Arg Thr Pro Leu His His Ala Ala Glu Asn Gly
65                  70                  75                  80

His Lys Glu Val Val Lys Leu Leu Ile Ser Lys Gly Ala Asp Val Asn
                85                  90                  95

Ala Lys Asp Ser Asp Gly Arg Thr Pro Leu His His Ala Ala Glu Asn
            100                 105                 110

Gly His Lys Glu Val Val Lys Leu Leu Ile Ser Lys Gly Ala Asp Val
        115                 120                 125

Asn Thr Ser Asp Ser Asp Gly Arg Thr Pro Leu Asp Leu Ala Arg Glu
    130                 135                 140

His Gly Asn Glu Glu Val Val Lys Leu Leu Glu Lys Gln
145                 150                 155

<210> SEQ ID NO 6
<211> LENGTH: 157
<212> TYPE: PRT
<213> ORGANISM: Artificial Sequence
<220> FEATURE:
<223> OTHER INFORMATION: Synthetic

<400> SEQUENCE: 6

Ser Glu Leu Gly Lys Arg Leu Ile Glu Ala Ala Glu Asn Gly Asn Lys
1               5                   10                  15

Asp Arg Val Lys Asp Leu Leu Glu Asn Gly Ala Asp Val Asn Ala Ser
            20                  25                  30

Asp Ser Asp Gly Lys Thr Pro Leu His Leu Ala Ala Glu Asn Gly His
        35                  40                  45

Lys Glu Val Val Lys Leu Leu Leu Ser Gln Gly Ala Asp Pro Asn Ala
50                  55                  60

Lys Asp Ser Asp Gly Lys Thr Pro Leu His Leu Ala Ala Glu Asn Gly
65                  70                  75                  80

His Lys Glu Val Val Lys Leu Leu Leu Ser Gln Gly Ala Asp Pro Asn
                85                  90                  95

Ala Lys Asp Ser Asp Gly Lys Thr Pro Leu His Leu Ala Ala Glu Asn
            100                 105                 110

Gly His Lys Glu Val Val Lys Leu Leu Leu Ser Gln Gly Ala Asp Pro
```

```
                115                 120                 125

Asn Thr Ser Asp Ser Asp Gly Arg Thr Pro Leu Asp Leu Ala Arg Glu
        130                 135                 140

His Gly Asn Glu Glu Val Val Lys Leu Leu Glu Lys Gln
145                 150                 155

<210> SEQ ID NO 7
<211> LENGTH: 157
<212> TYPE: PRT
<213> ORGANISM: Artificial Sequence
<220> FEATURE:
<223> OTHER INFORMATION: Synthetic

<400> SEQUENCE: 7

Ser Glu Leu Gly Lys Arg Leu Ile Glu Ala Ala Glu Asn Gly Asn Lys
1               5                   10                  15

Asp Arg Val Lys Asp Leu Leu Glu Asn Gly Ala Asp Pro Asn Ala Ser
            20                  25                  30

Asp Ser Asp Gly Arg Thr Pro Leu His Tyr Ala Ala Glu Asn Gly His
        35                  40                  45

Lys Glu Ile Val Lys Leu Leu Leu Ser Lys Gly Ala Asp Pro Asn Ala
50                  55                  60

Lys Asp Ser Asp Gly Arg Thr Pro Leu His Tyr Ala Ala Glu Asn Gly
65                  70                  75                  80

His Lys Glu Ile Val Lys Leu Leu Leu Ser Lys Gly Ala Asp Pro Asn
                85                  90                  95

Ala Lys Asp Ser Asp Gly Arg Thr Pro Leu His Tyr Ala Ala Glu Asn
            100                 105                 110

Gly His Lys Glu Ile Val Lys Leu Leu Leu Ser Lys Gly Ala Asp Pro
        115                 120                 125

Asn Thr Ser Asp Ser Asp Gly Arg Thr Pro Leu Asp Leu Ala Arg Glu
        130                 135                 140

His Gly Asn Glu Glu Ile Val Lys Leu Leu Glu Lys Gln
145                 150                 155

<210> SEQ ID NO 8
<211> LENGTH: 119
<212> TYPE: PRT
<213> ORGANISM: Artificial Sequence
<220> FEATURE:
<223> OTHER INFORMATION: Synthetic

<400> SEQUENCE: 8

Asn Ser Ala Glu Ala Trp Tyr Asn Leu Gly Asn Ala Tyr Tyr Lys Gln
1               5                   10                  15

Gly Asp Tyr Asp Glu Ala Ile Glu Tyr Tyr Gln Lys Ala Leu Glu Leu
            20                  25                  30

Asp Pro Asn Asn Ala Glu Ala Trp Tyr Asn Leu Gly Asn Ala Tyr Tyr
        35                  40                  45

Lys Gln Gly Asp Tyr Asp Glu Ala Ile Glu Tyr Tyr Gln Lys Ala Leu
    50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Gln Lys
                85                  90                  95

Ala Leu Glu Leu Asp Pro Asn Asn Ala Glu Ala Lys Gln Asn Leu Gly
            100                 105                 110
```

Asn Ala Lys Gln Lys Gln Gly
        115

<210> SEQ ID NO 9
<211> LENGTH: 136
<212> TYPE: PRT
<213> ORGANISM: Artificial Sequence
<220> FEATURE:
<223> OTHER INFORMATION: Synthetic

<400> SEQUENCE: 9

Ala Glu Ala Trp Lys Glu Leu Gly Lys Val Leu Glu Lys Leu Gly Arg
1               5                   10                  15

Leu Asp Glu Ala Ala Glu Ala Tyr Lys Lys Ala Ile Glu Leu Asp Pro
            20                  25                  30

Asn Asp Ala Glu Ala Trp Lys Glu Leu Gly Lys Val Leu Glu Lys Leu
        35                  40                  45

Gly Arg Leu Asp Glu Ala Ala Glu Ala Tyr Lys Lys Ala Ile Glu Leu
    50                  55                  60

Asp Pro Asn Asp Ala Glu Ala Trp Lys Glu Leu Gly Lys Val Leu Glu
65                  70                  75                  80

Lys Leu Gly Arg Leu Asp Glu Ala Ala Glu Ala Tyr Lys Lys Ala Ile
                85                  90                  95

Glu Leu Asp Pro Asn Asp Ala Glu Ala Trp Lys Glu Leu Gly Lys Val
            100                 105                 110

Leu Glu Lys Leu Gly Arg Leu Asp Glu Ala Ala Glu Ala Tyr Lys Lys
        115                 120                 125

Ala Ile Glu Leu Asp Pro Asn Asp
    130                 135

<210> SEQ ID NO 10
<211> LENGTH: 136
<212> TYPE: PRT
<213> ORGANISM: Artificial Sequence
<220> FEATURE:
<223> OTHER INFORMATION: Synthetic

<400> SEQUENCE: 10

Ala Ser Ser Trp Val Met Leu Gly Leu Leu Ser Leu Leu Asn Arg
1               5                   10                  15

Leu Ser Leu Ala Ala Glu Ala Tyr Lys Lys Ala Ile Glu Leu Asp Pro
            20                  25                  30

Asn Asp Ala Leu Ala Trp Leu Leu Leu Gly Ser Val Leu Glu Lys Leu
        35                  40                  45

Lys Arg Leu Asp Glu Ala Ala Glu Ala Tyr Lys Lys Ala Ile Glu Leu
    50                  55                  60

Lys Pro Asn Asp Ala Ser Ala Trp Lys Glu Leu Gly Lys Val Leu Glu
65                  70                  75                  80

Lys Leu Gly Arg Leu Asp Glu Ala Ala Glu Ala Tyr Lys Lys Ala Ile
                85                  90                  95

Glu Leu Asp Pro Glu Asp Ala Glu Ala Trp Lys Glu Leu Gly Lys Val
            100                 105                 110

Leu Glu Lys Leu Gly Arg Leu Asp Glu Ala Ala Glu Ala Tyr Lys Lys
        115                 120                 125

Ala Ile Glu Leu Asp Pro Asn Asp
    130                 135

<210> SEQ ID NO 11

<211> LENGTH: 187
<212> TYPE: PRT
<213> ORGANISM: Artificial Sequence
<220> FEATURE:
<223> OTHER INFORMATION: Synthetic

<400> SEQUENCE: 11

```
Thr Asp Pro Glu Lys Val Glu Met Tyr Ile Lys Asn Leu Gln Asp Asp
1               5                   10                  15

Ser Tyr Tyr Val Arg Arg Ala Ala Tyr Ala Leu Gly Lys Ile Gly
            20                  25                  30

Asp Glu Arg Ala Val Glu Pro Leu Ile Lys Ala Leu Lys Asp Glu Asp
            35                  40                  45

Ala Trp Val Arg Ala Ala Ala Asp Ala Leu Gly Gln Ile Gly Asp
    50                  55                  60

Glu Arg Ala Val Glu Pro Leu Ile Lys Ala Leu Lys Asp Glu Asp Gly
65                  70                  75                  80

Trp Val Arg Gln Ser Ala Ala Val Ala Leu Gly Gln Ile Gly Asp Glu
                85                  90                  95

Arg Ala Val Glu Pro Leu Ile Lys Ala Leu Lys Asp Glu Asp Trp Phe
                100                 105                 110

Val Arg Ile Ala Ala Ala Phe Ala Leu Gly Glu Ile Gly Asp Glu Arg
            115                 120                 125

Ala Val Glu Pro Leu Ile Lys Ala Leu Lys Asp Glu Asp Gly Trp Val
            130                 135                 140

Arg Gln Ser Ala Ala Asp Ala Leu Gly Glu Ile Gly Gly Glu Arg Val
145                 150                 155                 160

Arg Ala Ala Met Glu Lys Leu Ala Glu Thr Gly Thr Gly Phe Ala Arg
                165                 170                 175

Lys Val Ala Val Asn Tyr Leu Glu Thr His Lys
            180                 185
```

<210> SEQ ID NO 12
<211> LENGTH: 157
<212> TYPE: PRT
<213> ORGANISM: Artificial Sequence
<220> FEATURE:
<223> OTHER INFORMATION: Synthetic

<400> SEQUENCE: 12

```
Ser Glu Leu Gly Lys Arg Leu Ile Glu Ala Ala Glu Asn Gly Asn Lys
1               5                   10                  15

Asp Arg Val Lys Asp Leu Ile Glu Asn Gly Ala Asp Val Asn Ala Ser
            20                  25                  30

Asp Ser Asp Gly Arg Thr Pro Leu His His Ala Ala Glu Asn Gly His
            35                  40                  45

Ala Glu Val Val Ala Leu Leu Ile Glu Lys Gly Ala Asp Val Asn Ala
    50                  55                  60

Lys Asp Ser Asp Gly Arg Thr Pro Leu His His Ala Ala Glu Asn Gly
65                  70                  75                  80

His Asp Glu Val Val Leu Ile Leu Leu Lys Gly Ala Asp Val Asn
                85                  90                  95

Ala Lys Asp Ser Asp Gly Arg Thr Pro Leu His His Ala Ala Glu Asn
            100                 105                 110

Gly His Lys Arg Val Val Leu Val Leu Ile Leu Ala Gly Ala Asp Val
            115                 120                 125

Asn Thr Ser Asp Ser Asp Gly Arg Thr Pro Leu Asp Leu Ala Arg Glu
```

```
                130                 135                 140
His Gly Asn Glu Glu Val Val Lys Ala Leu Glu Lys Gln
145                 150                 155

<210> SEQ ID NO 13
<211> LENGTH: 157
<212> TYPE: PRT
<213> ORGANISM: Artificial Sequence
<220> FEATURE:
<223> OTHER INFORMATION: Synthetic

<400> SEQUENCE: 13

Ser Glu Asp Gly Glu Leu Leu Ile Leu Ala Ala Glu Leu Gly Ile Ala
1               5                   10                  15

Glu Ala Val Arg Met Leu Ile Glu Gln Gly Ala Asp Val Asn Ala Ser
                20                  25                  30

Asp Asp Asp Gly Arg Thr Pro Leu His Ala Ala Glu Asn Gly His
            35                  40                  45

Leu Ala Val Val Leu Leu Leu Leu Lys Gly Ala Asp Val Asn Ala
        50                  55                  60

Lys Asp Ser Asp Gly Arg Thr Pro Leu His Ala Ala Glu Asn Gly
65                  70                  75                  80

His Lys Thr Val Val Leu Leu Ile Leu Met Gly Ala Asp Val Asn
                85                  90                  95

Ala Lys Asp Ser Asp Gly Arg Thr Pro Leu His Ala Ala Glu Asn
                100                 105                 110

Gly His Lys Glu Val Val Lys Leu Leu Ile Arg Lys Gly Ala Asp Val
            115                 120                 125

Asn Thr Ser Asp Ser Asp Gly Arg Thr Pro Leu Asp Leu Ala Arg Glu
            130                 135                 140

His Gly Asn Glu Glu Val Val Lys Leu Leu Glu Lys Gln
145                 150                 155

<210> SEQ ID NO 14
<211> LENGTH: 157
<212> TYPE: PRT
<213> ORGANISM: Artificial Sequence
<220> FEATURE:
<223> OTHER INFORMATION: Synthetic

<400> SEQUENCE: 14

Ser Glu Leu Gly Lys Arg Leu Ile Glu Ala Ala Glu Asn Gly Asn Lys
1               5                   10                  15

Asp Arg Val Lys Asp Leu Leu Glu Asn Gly Ala Asp Val Asn Ala Ser
                20                  25                  30

Asp Ser Asp Gly Lys Thr Pro Leu His Leu Ala Ala Glu Asn Gly His
            35                  40                  45

Ala Lys Val Val Leu Leu Leu Leu Glu Gln Gly Ala Asp Pro Asn Ala
        50                  55                  60

Lys Asp Ser Asp Gly Lys Thr Pro Leu His Leu Ala Ala Glu Asn Gly
65                  70                  75                  80

His Ala Val Val Val Ala Leu Leu Leu Met His Gly Ala Asp Pro Asn
                85                  90                  95

Ala Lys Asp Ser Asp Gly Lys Thr Pro Leu His Leu Ala Ala Glu Asn
                100                 105                 110

Gly His Glu Glu Val Val Ile Leu Leu Leu Ala Met Gly Ala Asp Pro
            115                 120                 125
```

```
Asn Thr Ser Asp Ser Asp Gly Arg Thr Pro Leu Asp Leu Ala Arg Glu
    130                 135                 140

His Gly Asn Glu Glu Val Val Lys Val Leu Glu Asp His
145                 150                 155

<210> SEQ ID NO 15
<211> LENGTH: 159
<212> TYPE: PRT
<213> ORGANISM: Artificial Sequence
<220> FEATURE:
<223> OTHER INFORMATION: Synthetic

<400> SEQUENCE: 15

Ser Thr Glu Gly Lys Met Leu Ile Ile Ala Ala Arg Glu Gly Met Ile
1               5                   10                  15

Ile Val Val Ile Val Leu Leu Glu Lys Gly Ala Asp Pro Asn Ala Ser
            20                  25                  30

Asp Lys Asp Gly Arg Thr Pro Leu His Tyr Ala Ala Glu Asn Gly His
        35                  40                  45

Leu Ile Ile Val Leu Leu Leu Glu Lys Gly Ala Asp Pro Asn Ala
    50                  55                  60

Lys Asp Ser Asp Gly Arg Thr Pro Leu His Tyr Ala Ala Glu Asn Gly
65                  70                  75                  80

His Lys Glu Ile Val Glu Ala Leu Leu Glu His Gly Ala Asp Pro Asn
                85                  90                  95

Ala Lys Asp Ser Asp Gly Arg Thr Pro Leu His Tyr Ala Ala Glu Asn
            100                 105                 110

Gly His Lys Glu Ile Val Lys Leu Leu Leu Ser Lys Gly Ala Asp Pro
        115                 120                 125

Asn Thr Ser Asp Ser Asp Gly Arg Thr Pro Leu Asp Leu Ala Arg Glu
    130                 135                 140

His Gly Asn Glu Glu Ile Val Lys Leu Leu Glu Lys Gln Leu Glu
145                 150                 155

<210> SEQ ID NO 16
<211> LENGTH: 119
<212> TYPE: PRT
<213> ORGANISM: Artificial Sequence
<220> FEATURE:
<223> OTHER INFORMATION: Synthetic

<400> SEQUENCE: 16

Glu Arg Ala Glu Met Ala Ala Ile Val Gly Asp Ala Ile Tyr Ile Met
1               5                   10                  15

Gly Leu Tyr Arg Leu Ala Ile Lys Met Tyr Leu Ile Ala Leu Lys Leu
            20                  25                  30

Asp Pro Asn Asn Ala Glu Ala Trp Tyr Asn Leu Gly Asn Ala Tyr Tyr
        35                  40                  45

Lys Gln Gly Asp Tyr Asp Glu Ala Ile Glu Tyr Tyr Gln Lys Ala Leu
    50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Gln Lys
                85                  90                  95

Ala Leu Glu Leu Asp Pro Asn Asn Ala Glu Ala Lys Gln Asn Leu Gly
            100                 105                 110

Asn Ala Lys Gln Lys Gln Gly
        115
```

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

```
Glu Glu Ala Glu Leu Ala Tyr Leu Leu Gly Glu Leu Ala Tyr Lys Leu
1               5                   10                  15
Gly Glu Tyr Arg Ile Ala Ile Arg Ala Tyr Arg Ile Ala Leu Lys Arg
                20                  25                  30
Asp Pro Asn Asn Ala Glu Ala Trp Tyr Asn Leu Gly Asn Ala Tyr Tyr
            35                  40                  45
Lys Gln Gly Asp Tyr Asp Glu Ala Ile Glu Tyr Tyr Gln Lys Ala Leu
        50                  55                  60
Glu Leu Asp Pro Asn Asn Ala Glu Ala Trp Tyr Asn Leu Gly Asn Ala
65                  70                  75                  80
Tyr Tyr Lys Gln Gly Asp Tyr Asp Glu Ala Ile Glu Tyr Tyr Gln Lys
                85                  90                  95
Ala Leu Glu Leu Asp Pro Asn Asn Ala Glu Ala Lys Gln Asn Leu Gly
            100                 105                 110
Asn Ala Lys Gln Lys Gln Gly
        115
```

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

```
Asn Leu Ala Glu Lys Met Tyr Lys Ala Gly Asn Ala Met Tyr Arg Lys
1               5                   10                  15
Gly Gln Tyr Thr Ile Ala Ile Ile Ala Tyr Thr Leu Ala Leu Leu Lys
                20                  25                  30
Asp Pro Asn Asn Ala Glu Ala Trp Tyr Asn Leu Gly Asn Ala Ala Tyr
            35                  40                  45
Lys Lys Gly Glu Tyr Asp Glu Ala Ile Glu Ala Tyr Gln Lys Ala Leu
        50                  55                  60
Glu Leu Asp Pro Asn Asn Ala Glu Ala Trp Tyr Asn Leu Gly Asn Ala
65                  70                  75                  80
Tyr Tyr Lys Gln Gly Asp Tyr Asp Glu Ala Ile Glu Tyr Tyr Gln Lys
                85                  90                  95
Ala Leu Glu Leu Asp Pro Asn Asn Ala Glu Ala Lys Gln Asn Leu Gly
            100                 105                 110
Asn Ala Lys Gln Lys Gln Gly
        115
```

<210> SEQ ID NO 19
<211> LENGTH: 119
<212> TYPE: PRT
<213> ORGANISM: Artificial Sequence
<220> FEATURE:
<223> OTHER INFORMATION: Synthetic

<400> SEQUENCE: 19

Asn Glu Ala Glu Leu Ala Tyr Asp Leu Gly Asn Glu Ala Tyr Lys Asp
1               5                   10                  15

Gly Glu Tyr Arg Leu Ala Val Ala Tyr Val Leu Ala Leu Ala Val
            20                  25                  30

Asp Pro Asn Asn Ala Glu Ala Trp Tyr Asn Leu Gly Asn Ala Tyr Tyr
            35                  40                  45

Lys Gln Gly Arg Tyr Asp Lys Ala Ile Lys Tyr Tyr Gln Lys Ala Leu
        50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Gln Lys
                85                  90                  95

Ala Leu Glu Leu Asp Pro Asn Asn Ala Glu Ala Lys Gln Asn Leu Gly
            100                 105                 110

Asn Ala Lys Gln Lys Gln Gly
            115

<210> SEQ ID NO 20
<211> LENGTH: 119
<212> TYPE: PRT
<213> ORGANISM: Artificial Sequence
<220> FEATURE:
<223> OTHER INFORMATION: Synthetic

<400> SEQUENCE: 20

Asn Ser Ala Glu Ala Met Tyr Lys Met Gly Asn Ala Ala Tyr Lys Gln
1               5                   10                  15

Gly Asp Tyr Ile Leu Ala Ile Ile Ala Tyr Leu Leu Ala Leu Glu Lys
            20                  25                  30

Asp Pro Asn Asn Ala Glu Ala Trp Tyr Asn Leu Gly Asn Ala Ala Tyr
            35                  40                  45

Lys Gln Gly Asp Tyr Asp Glu Ala Ile Glu Tyr Tyr Gln Lys Ala Leu
        50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Gln Lys
                85                  90                  95

Ala Leu Glu Leu Asp Pro Asn Asn Ala Glu Ala Lys Gln Asn Leu Gly
            100                 105                 110

Asn Ala Lys Gln Lys Gln Gly
            115

<210> SEQ ID NO 21
<211> LENGTH: 119
<212> TYPE: PRT
<213> ORGANISM: Artificial Sequence
<220> FEATURE:
<223> OTHER INFORMATION: Synthetic

<400> SEQUENCE: 21

Thr Leu Ala Arg Val Ala Tyr Ile Leu Gly Ala Ile Ala Tyr Ala Gln
1               5                   10                  15

Gly Glu Tyr Asp Ile Ala Ile Thr Ala Tyr Gln Val Ala Leu Asp Leu
            20                  25                  30

Asp Pro Asn Asn Ala Glu Ala Trp Tyr Asn Leu Gly Asn Ala Tyr Tyr
            35                  40                  45

Lys Gln Gly Asp Tyr Asp Glu Ala Ile Glu Tyr Tyr Gln Lys Ala Leu
        50                  55                  60

```
Glu Leu Asp Pro Asn Asn Ala Glu Ala Trp Tyr Asn Leu Gly Asn Ala
 65                  70                  75                  80

Tyr Tyr Lys Gln Gly Asp Tyr Asp Glu Ala Ile Glu Tyr Tyr Gln Lys
                 85                  90                  95

Ala Leu Glu Leu Asp Pro Asn Asn Ala Glu Ala Lys Gln Asn Leu Gly
            100                 105                 110

Asn Ala Lys Gln Lys Gln Gly
        115

<210> SEQ ID NO 22
<211> LENGTH: 187
<212> TYPE: PRT
<213> ORGANISM: Artificial Sequence
<220> FEATURE:
<223> OTHER INFORMATION: Synthetic

<400> SEQUENCE: 22

Thr Asp Pro Leu Ala Val Ile Leu Tyr Ile Ala Ile Leu Lys Ala Glu
  1               5                  10                  15

Lys Ser Ile Ala Arg Ala Lys Ala Ala Glu Ala Leu Gly Lys Ile Gly
             20                  25                  30

Asp Glu Arg Ala Val Glu Pro Leu Ile Lys Ala Leu Lys Asp Glu Asp
         35                  40                  45

Ala Leu Val Arg Ala Ala Ala Asp Ala Leu Gly Gln Ile Gly Asp
     50                  55                  60

Glu Arg Ala Val Glu Pro Leu Ile Lys Ala Leu Lys Asp Glu Glu Gly
 65                  70                  75                  80

Leu Val Arg Ala Ser Ala Ala Ile Ala Leu Gly Gln Ile Gly Asp Glu
                 85                  90                  95

Arg Ala Val Glu Pro Leu Ile Lys Ala Leu Lys Asp Glu Arg Asp Leu
            100                 105                 110

Val Arg Val Ala Ala Val Ala Leu Gly Arg Ile Gly Asp Glu Arg
        115                 120                 125

Ala Val Glu Pro Leu Ile Lys Ala Leu Lys Asp Glu Glu Gly Glu Val
    130                 135                 140

Arg Glu Ala Ala Ala Ile Ala Leu Gly Ser Ile Gly Gly Glu Arg Val
145                 150                 155                 160

Arg Ala Ala Met Glu Lys Leu Ala Glu Thr Gly Thr Gly Phe Ala Arg
                165                 170                 175

Lys Val Ala Val Asn Tyr Leu Glu Thr His Lys
            180                 185

<210> SEQ ID NO 23
<211> LENGTH: 190
<212> TYPE: PRT
<213> ORGANISM: Artificial Sequence
<220> FEATURE:
<223> OTHER INFORMATION: Synthetic

<400> SEQUENCE: 23

Arg Arg Glu Glu Asp Pro Leu Ala Val Val Met Tyr Arg Leu Asn Leu
  1               5                  10                  15

Arg Asp Asp Ser Tyr Tyr Val Arg Arg Ala Ala Ala Tyr Ala Leu Gly
             20                  25                  30

Lys Ile Gly Asp Glu Arg Ala Val Glu Pro Leu Ile Lys Ala Leu Lys
         35                  40                  45

Asp Glu Asp Ala Trp Val Arg Arg Ala Ala Ala Asp Ala Leu Gly Gln
```

```
            50                  55                  60
Ile Gly Asp Glu Arg Ala Val Glu Pro Leu Ile Lys Ala Leu Lys Asp
 65                  70                  75                  80

Glu Asp Gly Trp Val Arg Gln Ser Ala Ala Val Ala Leu Gly Gln Ile
                 85                  90                  95

Gly Asp Glu Arg Ala Val Glu Pro Leu Ile Lys Ala Leu Lys Asp Glu
            100                 105                 110

Asp Trp Phe Val Arg Ala Ala Ala Ala Ala Leu Gly Arg Ile Gly
        115                 120                 125

Asp Glu Arg Ala Val Glu Pro Leu Ile Lys Ala Leu Lys Asp Glu Asp
        130                 135                 140

Glu Met Val Arg Glu Ile Ala Ala Leu Ala Leu Gly Met Ile Gly Gly
145                 150                 155                 160

Glu Arg Val Arg Ala Ala Met Glu Lys Leu Ala Glu Thr Gly Thr Gly
                165                 170                 175

Phe Ala Arg Lys Val Ala Val Asn Tyr Leu Glu Thr His Lys
            180                 185                 190
```

<210> SEQ ID NO 24
<211> LENGTH: 279
<212> TYPE: PRT
<213> ORGANISM: Artificial Sequence
<220> FEATURE:
<223> OTHER INFORMATION: Synthetic

<400> SEQUENCE: 24

```
Ile Glu Glu Val Val Ala Glu Met Ile Asp Ile Leu Ala Glu Ser Ser
 1               5                  10                  15

Lys Lys Ser Ile Glu Glu Leu Ala Arg Ala Ala Asp Asn Lys Thr Thr
             20                  25                  30

Glu Lys Ala Val Ala Glu Ala Ile Glu Glu Ile Ala Arg Leu Ala Thr
         35                  40                  45

Ala Ala Ile Gln Leu Ile Glu Ala Leu Ala Lys Asn Leu Ala Ser Glu
     50                  55                  60

Glu Phe Met Ala Arg Ala Ile Ser Ala Ile Ala Glu Leu Ala Lys Lys
 65                  70                  75                  80

Ala Ile Glu Ala Ile Tyr Arg Leu Ala Asp Asn His Thr Thr Asp Thr
                 85                  90                  95

Phe Met Ala Arg Ala Ile Ala Ala Ile Ala Asn Leu Ala Val Thr Ala
            100                 105                 110

Ile Leu Ala Ile Ala Ala Leu Ala Ser Asn His Thr Thr Glu Glu Phe
        115                 120                 125

Met Ala Arg Ala Ile Ser Ala Ile Ala Glu Leu Ala Lys Lys Ala Ile
    130                 135                 140

Glu Ala Ile Tyr Arg Leu Ala Asp Asn His Thr Thr Asp Lys Phe Met
145                 150                 155                 160

Ala Ala Ala Ile Glu Ala Ile Ala Leu Leu Ala Thr Leu Ala Ile Leu
                165                 170                 175

Ala Ile Ala Leu Leu Ala Ser Asn His Thr Thr Glu Glu Phe Met Ala
            180                 185                 190

Lys Ala Ile Ser Ala Ile Ala Glu Leu Ala Lys Lys Ala Ile Glu Ala
        195                 200                 205

Ile Tyr Arg Leu Ala Asp Asn His Thr Ser Pro Thr Tyr Ile Glu Lys
    210                 215                 220

Ala Ile Glu Ala Ile Glu Lys Ile Ala Arg Lys Ala Ile Lys Ala Ile
```

```
                  225                 230                 235                 240
Glu Met Leu Ala Lys Asn Ile Thr Thr Glu Glu Tyr Lys Glu Lys Ala
                      245                 250                 255

Lys Ser Ala Ile Asp Glu Ile Arg Glu Lys Ala Lys Glu Ala Ile Lys
                      260                 265                 270

Arg Leu Glu Asp Asn Arg Thr
                      275

<210> SEQ ID NO 25
<211> LENGTH: 197
<212> TYPE: PRT
<213> ORGANISM: Artificial Sequence
<220> FEATURE:
<223> OTHER INFORMATION: Synthetic

<400> SEQUENCE: 25

Asp Glu Cys Glu Glu Lys Ala Arg Arg Val Ala Glu Lys Val Glu Arg
1               5                   10                  15

Leu Lys Arg Ser Gly Thr Ser Glu Asp Glu Ile Ala Glu Glu Val Ala
                20                  25                  30

Arg Glu Ile Ser Glu Val Ile Arg Thr Leu Lys Glu Ser Gly Ser Glu
            35                  40                  45

Tyr Lys Val Ile Cys Arg Cys Val Ala Arg Ile Val Ala Glu Ile Val
        50                  55                  60

Glu Ala Leu Lys Arg Ser Gly Thr Ser Glu Asp Glu Ile Ala Glu Ile
65                  70                  75                  80

Val Ala Arg Val Ile Ser Glu Val Ile Arg Thr Leu Lys Glu Ser Gly
                85                  90                  95

Ser Asp Tyr Leu Ile Ile Cys Val Cys Val Ala Ile Ile Val Ala Glu
            100                 105                 110

Ile Val Glu Ala Leu Lys Arg Ser Gly Thr Ser Glu Asp Glu Ile Ala
        115                 120                 125

Glu Ile Val Ala Arg Val Ile Ser Glu Val Ile Arg Thr Leu Lys Glu
    130                 135                 140

Ser Gly Ser Ser Tyr Glu Val Ile Lys Glu Cys Val Gln Ile Ile Val
145                 150                 155                 160

Leu Ala Ile Ile Leu Ala Leu Met Lys Ser Gly Thr Glu Val Glu Glu
                165                 170                 175

Ile Leu Leu Ile Leu Leu Arg Val Lys Thr Glu Val Arg Arg Thr Leu
            180                 185                 190

Lys Glu Ser Gly Ser
        195

<210> SEQ ID NO 26
<211> LENGTH: 197
<212> TYPE: PRT
<213> ORGANISM: Artificial Sequence
<220> FEATURE:
<223> OTHER INFORMATION: Synthetic

<400> SEQUENCE: 26

Asp Glu Cys Glu Glu Lys Ala Arg Arg Val Ala Glu Lys Val Glu Arg
1               5                   10                  15

Leu Lys Arg Ser Gly Thr Ser Glu Asp Glu Ile Ala Glu Glu Val Ala
                20                  25                  30

Arg Glu Ile Ser Glu Val Ile Arg Thr Leu Lys Glu Ser Gly Ser Ser
            35                  40                  45
```

```
Tyr Glu Val Ile Cys Glu Cys Val Ala Arg Ile Val Ala Glu Ile Val
         50                  55                  60

Glu Ala Leu Lys Arg Ser Gly Thr Ser Ala Val Glu Ile Ala Lys Ile
 65                  70                  75                  80

Val Ala Arg Val Ile Ser Glu Val Ile Arg Thr Leu Lys Glu Ser Gly
                 85                  90                  95

Ser Ser Tyr Glu Val Ile Cys Glu Cys Val Ala Arg Ile Val Ala Glu
            100                 105                 110

Ile Val Glu Ala Leu Lys Arg Ser Gly Thr Ser Ala Ala Ile Ile Ala
            115                 120                 125

Leu Ile Val Ala Leu Val Ile Ser Glu Val Ile Arg Thr Leu Lys Glu
        130                 135                 140

Ser Gly Ser Ser Phe Glu Val Ile Leu Glu Cys Val Ile Arg Ile Val
145                 150                 155                 160

Leu Glu Ile Ile Glu Ala Leu Lys Arg Ser Gly Thr Ser Glu Gln Asp
                165                 170                 175

Val Met Leu Ile Val Met Ala Val Leu Leu Val Leu Ala Thr Leu
        180                 185                 190

Gln Leu Ser Gly Ser
        195

<210> SEQ ID NO 27
<211> LENGTH: 174
<212> TYPE: PRT
<213> ORGANISM: Artificial Sequence
<220> FEATURE:
<223> OTHER INFORMATION: Synthetic

<400> SEQUENCE: 27

Asp Glu Met Arg Lys Val Met Leu Ala Leu Ala Ile Ala Leu Val Arg
 1               5                  10                  15

Ala Leu Leu Asn Glu Asp Ile Glu Val Ala Lys Glu Ile Ala Arg Ala
                 20                  25                  30

Ala Asp Glu Ile Glu Glu Ala Leu Arg Glu Asn Asn Ser Asp Glu Met
            35                  40                  45

Ala Lys Val Met Leu Ala Leu Ala Lys Ala Val Leu Leu Ala Ala Lys
        50                  55                  60

Asn Asn Asp Asp Arg Val Ala Glu Val Ile Ala Leu Ala Ala Ala Glu
 65                  70                  75                  80

Ile Val Lys Ala Leu Arg Arg Asn Asn Ser Asp Glu Met Ala Lys Val
                 85                  90                  95

Met Leu Ala Leu Ala Lys Ala Val Leu Leu Ala Ala Lys Asn Asn Asp
            100                 105                 110

Asp Glu Val Ala Lys Glu Ile Ala Ile Ala Ala Met Ile Ile Val Ile
        115                 120                 125

Ala Leu Arg Ala Glu Asn Ser Asp Glu Met Ala Lys Lys Met Leu Glu
        130                 135                 140

Leu Ala Lys Arg Val Leu Asp Ala Ala Lys Asn Asn Asp Asp Glu Thr
145                 150                 155                 160

Ala Arg Glu Ile Ala Glu Gln Ala Ala Glu Glu Leu Glu Ala
                165                 170

<210> SEQ ID NO 28
<211> LENGTH: 195
<212> TYPE: PRT
<213> ORGANISM: Artificial Sequence
<220> FEATURE:
```

<223> OTHER INFORMATION: Synthetic

<400> SEQUENCE: 28

```
Ser Ser Glu Lys Glu Leu Arg Glu Arg Leu Val Lys Ile Val Val
1               5                   10                  15

Glu Asn Ala Lys Arg Lys Gly Asp Asp Thr Glu Glu Ala Arg Glu Ala
            20                  25                  30

Ala Arg Ala Ala Phe Glu Ile Val Arg Ala Ala Lys Leu Ala Gly
            35                  40                  45

Ile Asp Ser Ser Glu Val Leu Glu Leu Ala Ile Arg Leu Ile Lys Glu
    50                  55                  60

Val Val Glu Asn Ala Gln Arg Glu Gly Tyr Asp Ile Ala Val Ala Ala
65                  70                  75                  80

Ile Ala Ala Ala Val Ala Phe Ala Val Val Ala Val Ala Ala Ala
                85                  90                  95

Ala Asp Ile Thr Ser Ser Glu Val Leu Glu Leu Ala Ile Arg Leu Ile
            100                 105                 110

Lys Glu Val Val Glu Asn Ala Gln Arg Glu Gly Tyr Val Ile Leu Leu
            115                 120                 125

Ala Ala Leu Ala Ala Ala Ala Phe Val Val Val Ala Ala Ala
            130                 135                 140

Lys Arg Ala Gly Ile Thr Ser Ser Glu Thr Leu Lys Arg Ala Ile Glu
145                 150                 155                 160

Glu Ile Arg Lys Arg Val Glu Ala Gln Arg Gly Asn Asp Ile
            165                 170                 175

Ser Glu Ala Ala Arg Gln Ala Ala Glu Glu Phe Arg Lys Lys Ala Glu
            180                 185                 190

Glu Leu Lys
        195
```

<210> SEQ ID NO 29
<211> LENGTH: 195
<212> TYPE: PRT
<213> ORGANISM: Artificial Sequence
<220> FEATURE:
<223> OTHER INFORMATION: Synthetic

<400> SEQUENCE: 29

```
Ser Ala Glu Lys Leu Met Leu Met Ala Lys Leu Ile Ile Ile Val Ala
1               5                   10                  15

Glu Asn Ala Lys Arg Lys Gly Asp Asp Thr Leu Ile Ala Ile Met Ala
            20                  25                  30

Ala Lys Leu Ala Phe Glu Ile Val Arg Ile Ala Ala Glu Glu Ala Gly
            35                  40                  45

Ile Asp Ser Ser Glu Val Leu Glu Leu Ala Ile Arg Leu Ile Lys Glu
    50                  55                  60

Val Val Glu Asn Ala Gln Arg Glu Gly Tyr Asp Ile Ser Ile Ala Ala
65                  70                  75                  80

Leu Ala Ala Ala Met Ala Phe Ala Leu Val Ala Ile Ala Ala Lys Arg
                85                  90                  95

Ala Gly Ile Thr Ser Ser Glu Val Leu Glu Leu Ala Ile Arg Leu Ile
            100                 105                 110

Lys Glu Val Val Glu Asn Ala Gln Arg Glu Gly Tyr Asp Ile Ala Glu
            115                 120                 125

Ala Ala Arg Ala Ala Ala Glu Ala Phe Lys Arg Val Ala Glu Ala Ala
            130                 135                 140
```

```
Lys Arg Ala Gly Ile Thr Ser Ser Glu Thr Leu Lys Arg Ala Ile Glu
145                 150                 155                 160

Glu Ile Arg Lys Arg Val Glu Glu Ala Gln Arg Glu Gly Asn Asp Ile
            165                 170                 175

Ser Glu Ala Ala Arg Gln Ala Glu Glu Phe Arg Lys Lys Ala Glu
        180                 185                 190

Glu Leu Lys
        195
```

<210> SEQ ID NO 30
<211> LENGTH: 233
<212> TYPE: PRT
<213> ORGANISM: Artificial Sequence
<220> FEATURE:
<223> OTHER INFORMATION: Synthetic

<400> SEQUENCE: 30

```
Arg Ile Glu Lys Leu Cys Arg Ile Ala Glu Ala Leu Ala Arg Glu Ala
1               5                   10                  15

Arg Ser Lys Ala Glu Glu Leu Arg Gln Arg His Pro Asp Ser Gln Ala
            20                  25                  30

Ala Arg Asp Ala Gln Lys Leu Ala Ser Gln Ala Glu Glu Ala Val Lys
        35                  40                  45

Leu Ala Cys Glu Leu Ala Gln Glu His Pro Asn Ala Ile Ile Ala Ile
50                  55                  60

Leu Cys Ile Val Ala Ala Ile Ala Ala Ile Ala Ala Ser Met Ala
65                  70                  75                  80

Ala Ala Leu Ala Gln Arg His Pro Asp Ser Gln Ala Ala Arg Asp Ala
            85                  90                  95

Ile Lys Leu Ala Ser Gln Ala Ala Glu Ala Val Lys Leu Ala Cys Glu
        100                 105                 110

Leu Ala Gln Glu His Pro Asn Ala Lys Ile Ala Val Leu Cys Ile Leu
            115                 120                 125

Ala Ala Ala Leu Ala Ala Ile Ala Ala Ala Leu Ala Ala Leu Leu Ala
130                 135                 140

Gln Leu His Pro Asp Ser Gln Ala Ala Arg Asp Ala Ile Lys Leu Ala
145                 150                 155                 160

Ser Gln Ala Ala Glu Ala Val Lys Leu Ala Cys Glu Leu Ala Gln Glu
                165                 170                 175

His Pro Asn Ala Asp Ile Ala Glu Lys Cys Ile Leu Leu Ala Ile Leu
            180                 185                 190

Ala Ala Leu Leu Ala Ile Leu Ala Ala Leu Leu Ala Met Leu His Pro
        195                 200                 205

Asp Ser Gln Leu Ala Arg Asp Leu Ile Asp Leu Ala Ser Glu Leu Ala
    210                 215                 220

Glu Glu Val Lys Glu Arg Cys Glu Arg
225                 230
```

<210> SEQ ID NO 31
<211> LENGTH: 224
<212> TYPE: PRT
<213> ORGANISM: Artificial Sequence
<220> FEATURE:
<223> OTHER INFORMATION: Synthetic

<400> SEQUENCE: 31

```
Arg Glu Asp Glu Leu Arg Ala Arg Leu Leu Ile Leu Leu Ala Glu Leu
```

```
1               5                   10                  15
Ala Ala Glu Arg Ala Asp Ile Ala Ala Glu Arg Thr Gly Asp Pro Arg
            20                  25                  30
Val Arg Glu Leu Ala Arg Glu Leu Lys Arg Leu Ala Gln Glu Ala Ala
            35                  40                  45
Glu Glu Val Lys Arg Asp Pro Ser Ser Ser Asp Val Asn Glu Ala Leu
    50                  55                  60
Lys Leu Ile Val Glu Ala Ile Glu Ala Val Arg Ala Leu Glu Ala
65                  70                  75                  80
Ala Glu Arg Thr Gly Asp Pro Glu Val Arg Glu Leu Ala Arg Glu Leu
                85                  90                  95
Val Arg Leu Ala Val Glu Ala Ala Glu Val Gln Arg Asn Pro Ser
            100                 105                 110
Ser Ser Asp Val Asn Glu Ala Leu Lys Leu Ile Val Glu Ala Ile Glu
            115                 120                 125
Ala Ala Val Arg Ala Leu Glu Ala Ala Glu Arg Thr Gly Asp Pro Glu
            130                 135                 140
Val Arg Glu Leu Ala Arg Glu Leu Val Arg Leu Ala Val Glu Ala Ala
145                 150                 155                 160
Glu Glu Val Gln Arg Asn Pro Ser Ser Lys Glu Val Asp Met Ala Leu
                165                 170                 175
Leu Leu Ile Leu Ile Ala Ile Leu Glu Ala Val Leu Ser Leu Leu Arg
                180                 185                 190
Ala Glu Arg Ser Gly Asp Pro Glu Lys Arg Glu Lys Ala Arg Glu Arg
                195                 200                 205
Val Arg Glu Ala Val Glu Arg Ala Glu Glu Val Gln Arg Asp Pro Ser
    210                 215                 220

<210> SEQ ID NO 32
<211> LENGTH: 225
<212> TYPE: PRT
<213> ORGANISM: Artificial Sequence
<220> FEATURE:
<223> OTHER INFORMATION: Synthetic

<400> SEQUENCE: 32

Glu Arg Glu Glu Leu Ser Glu Leu Ala Glu Arg Ile Leu Gln Lys Ala
1               5                   10                  15
Arg Lys Leu Ser Glu Glu Ala Arg Glu Arg Gly Asp Leu Lys Glu Leu
            20                  25                  30
Ala Leu Ala Leu Ile Leu Glu Ala Leu Ala Val Leu Leu Leu Ala Ile
            35                  40                  45
Ala Ala Leu Leu Arg Gly Asn Ser Glu Glu Ala Glu Arg Ala Ser Glu
    50                  55                  60
Lys Ala Gln Arg Val Leu Glu Ala Arg Lys Val Ser Glu Glu Ala
65                  70                  75                  80
Arg Glu Gln Gly Asp Asp Glu Val Leu Ala Leu Ala Leu Ile Ala Ile
                85                  90                  95
Ala Leu Ala Val Leu Ala Leu Ala Leu Val Ala Cys Cys Arg Gly Asn
            100                 105                 110
Ser Glu Glu Ala Glu Arg Ala Ser Glu Lys Ala Gln Arg Val Leu Glu
            115                 120                 125
Glu Ala Arg Lys Val Ser Glu Glu Ala Arg Glu Gln Gly Asp Asp Glu
            130                 135                 140
Val Leu Ala Leu Ala Leu Ile Ala Ile Ala Leu Ala Val Leu Ala Leu
```

```
145                 150                 155                 160
Ala Ile Val Ala Cys Cys Arg Gly Asn Lys Glu Glu Ala Arg Ala
                165                 170                 175

Ala Glu Asp Ala Ile Lys Val Ala Met Glu Ala Leu Glu Val Leu Leu
            180                 185                 190

Ser Ala Val Glu Gln Gly Asp Leu Lys Val Ala Leu Ala Ala Val Ile
            195                 200                 205

Ala Ile Leu Leu Ala Ile Ala Ala Leu Leu Met Val Ile Met Cys Lys
210                 215                 220

Gly
225

<210> SEQ ID NO 33
<211> LENGTH: 119
<212> TYPE: PRT
<213> ORGANISM: Artificial Sequence
<220> FEATURE:
<223> OTHER INFORMATION: Synthetic

<400> SEQUENCE: 33

Asn Leu Ala Glu Lys Met Tyr Lys Ala Gly Asn Ala Met Tyr Arg Lys
1               5                   10                  15

Gly Gln Tyr Thr Ile Ala Ile Ile Ala Tyr Thr Leu Ala Leu Leu Lys
            20                  25                  30

Asp Pro Asn Asn Ala Glu Ala Trp Tyr Asn Leu Gly Asn Ala Ala Tyr
        35                  40                  45

Lys Lys Gly Glu Tyr Asp Glu Ala Ile Glu Ala Tyr Gln Lys Ala Leu
    50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Lys Lys
                85                  90                  95

Ala Leu Arg Leu Asp Pro Arg Asn Val Asp Ala Ile Glu Asn Leu Ile
            100                 105                 110

Glu Ala Glu Glu Lys Gln Gly
        115

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34

Glu Glu Ala Glu Leu Ala Tyr Leu Leu Gly Glu Leu Ala Tyr Lys Leu
1               5                   10                  15

Gly Glu Tyr Arg Ile Ala Ile Arg Ala Tyr Arg Ile Ala Leu Lys Arg
            20                  25                  30

Asp Pro Asn Asn Ala Glu Ala Trp Tyr Asn Leu Gly Asn Ala Tyr Tyr
        35                  40                  45

Lys Gln Gly Asp Tyr Arg Glu Ala Ile Arg Tyr Tyr Leu Arg Ala Leu
    50                  55                  60

Lys Leu Asp Pro Glu Asn Ala Glu Ala Trp Tyr Asn Leu Gly Asn Ala
65                  70                  75                  80

Leu Tyr Lys Gln Gly Lys Tyr Asp Leu Ala Ile Ile Ala Tyr Gln Ala
                85                  90                  95
```

```
Ala Leu Glu Glu Asp Pro Asn Asn Glu Ala Lys Gln Asn Leu Gly
            100                 105                 110

Asn Ala Lys Gln Lys Gln Gly
        115
```

<210> SEQ ID NO 35
<211> LENGTH: 119
<212> TYPE: PRT
<213> ORGANISM: Artificial Sequence
<220> FEATURE:
<223> OTHER INFORMATION: Synthetic

<400> SEQUENCE: 35

```
Asn Ser Ala Glu Ala Met Tyr Lys Met Gly Asn Ala Ala Tyr Lys Gln
1               5                   10                  15

Gly Asp Tyr Ile Leu Ala Ile Ile Ala Tyr Leu Leu Ala Leu Glu Lys
            20                  25                  30

Asp Pro Asn Asn Ala Glu Ala Trp Tyr Asn Leu Gly Asn Ala Ala Tyr
        35                  40                  45

Lys Gln Gly Asp Tyr Asp Glu Ala Ile Glu Tyr Tyr Gln Lys Ala Leu
    50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Glu Lys
                85                  90                  95

Ala Leu Glu Leu Asp Pro Asn Asn Ala Glu Ala Leu Lys Asn Leu Leu
            100                 105                 110

Glu Ala Ile Ala Glu Gln Asp
        115
```

<210> SEQ ID NO 36
<211> LENGTH: 187
<212> TYPE: PRT
<213> ORGANISM: Artificial Sequence
<220> FEATURE:
<223> OTHER INFORMATION: Synthetic

<400> SEQUENCE: 36

```
Thr Asp Pro Leu Ala Val Ile Leu Tyr Ile Ala Ile Leu Lys Ala Glu
1               5                   10                  15

Lys Ser Ile Ala Arg Ala Lys Ala Ala Glu Ala Leu Gly Lys Ile Gly
            20                  25                  30

Asp Glu Arg Ala Val Glu Pro Leu Ile Lys Ala Leu Lys Asp Glu Asp
        35                  40                  45

Ala Leu Val Arg Ala Ala Ala Asp Ala Leu Gly Gln Ile Gly Asp
    50                  55                  60

Glu Arg Ala Val Glu Pro Leu Ile Lys Ala Leu Lys Asp Glu Glu Gly
65                  70                  75                  80

Leu Val Arg Ala Ser Ala Ala Ile Ala Leu Gly Gln Ile Gly Asp Glu
                85                  90                  95

Arg Ala Val Gln Pro Leu Ile Lys Ala Leu Thr Asp Glu Arg Asp Leu
            100                 105                 110

Val Arg Val Ala Ala Val Ala Leu Gly Arg Ile Gly Asp Glu Lys
        115                 120                 125

Ala Val Arg Pro Leu Ile Ile Val Leu Lys Asp Glu Glu Gly Glu Val
    130                 135                 140

Arg Glu Ala Ala Ala Ile Ala Leu Gly Ser Ile Gly Gly Glu Arg Val
145                 150                 155                 160
```

Arg Ala Ala Met Glu Lys Leu Ala Glu Arg Gly Thr Gly Phe Ala Arg
                165                 170                 175

Lys Val Ala Val Asn Tyr Leu Glu Thr His Lys
            180                 185

<210> SEQ ID NO 37
<211> LENGTH: 119
<212> TYPE: PRT
<213> ORGANISM: Artificial Sequence
<220> FEATURE:
<223> OTHER INFORMATION: Synthetic

<400> SEQUENCE: 37

Glu Glu Ala Glu Leu Ala Tyr Leu Leu Gly Glu Leu Ala Tyr Lys Leu
1               5                   10                  15

Gly Glu Tyr Arg Ile Ala Ile Arg Ala Tyr Arg Ile Ala Leu Lys Arg
                20                  25                  30

Asp Pro Asn Asn Ala Glu Ala Trp Tyr Asn Leu Gly Asn Ala Tyr Tyr
            35                  40                  45

Lys Gln Gly Asp Tyr Asp Glu Ala Ile Glu Tyr Tyr Gln Lys Ala Leu
        50                  55                  60

Glu Leu Asp Pro Asn Asn Ala Glu Ala Trp Tyr Asn Leu Gly Asn Ala
65                  70                  75                  80

Tyr Tyr Lys Gln Gly Asp Tyr Asp Glu Ala Ile Glu Tyr Tyr Glu Lys
                85                  90                  95

Ala Leu Glu Leu Asp Pro Glu Asn Leu Glu Ala Leu Gln Asn Leu Leu
            100                 105                 110

Asn Ala Met Asp Lys Gln Gly
        115

<210> SEQ ID NO 38
<211> LENGTH: 279
<212> TYPE: PRT
<213> ORGANISM: Artificial Sequence
<220> FEATURE:
<223> OTHER INFORMATION: Synthetic

<400> SEQUENCE: 38

Ile Glu Glu Val Val Ala Glu Met Ile Asp Ile Leu Ala Glu Ser Ser
1               5                   10                  15

Lys Lys Ser Ile Glu Glu Leu Ala Arg Ala Ala Asp Asn Lys Thr Thr
                20                  25                  30

Glu Lys Ala Val Ala Glu Ala Ile Glu Glu Ile Ala Arg Leu Ala Thr
            35                  40                  45

Ala Ala Ile Gln Leu Ile Glu Ala Leu Ala Lys Asn Leu Ala Ser Glu
        50                  55                  60

Glu Phe Met Ala Arg Ala Ile Ser Ala Ile Ala Glu Leu Ala Lys Lys
65                  70                  75                  80

Ala Ile Glu Ala Ile Tyr Arg Leu Ala Asp Asn His Thr Thr Asp Thr
                85                  90                  95

Phe Met Ala Arg Ala Ile Ala Ala Ile Ala Asn Leu Ala Val Thr Ala
            100                 105                 110

Ile Leu Ala Ile Ala Ala Leu Ala Ser Asn His Thr Thr Glu Glu Phe
        115                 120                 125

Met Ala Arg Ala Ile Ser Ala Ile Ala Glu Leu Ala Lys Lys Ala Ile
130                 135                 140

Glu Ala Ile Tyr Arg Leu Ala Asp Asn His Thr Thr Asp Lys Phe Met

```
                145                 150                 155                 160
Ala Ala Ala Ile Glu Ala Ile Ala Leu Leu Ala Thr Leu Ala Ile Leu
                    165                 170                 175

Ala Ile Ala Leu Leu Ala Ser Asn His Thr Thr Glu Lys Phe Met Ala
            180                 185                 190

Arg Ala Ile Met Ala Ile Ala Ile Leu Ala Ala Lys Ala Ile Glu Ala
            195                 200                 205

Ile Tyr Arg Leu Ala Asp Asn His Thr Ser Pro Thr Tyr Ile Glu Lys
    210                 215                 220

Ala Ile Glu Ala Ile Glu Lys Ile Ala Arg Lys Ala Ile Lys Ala Ile
225                 230                 235                 240

Glu Met Leu Ala Lys Asn Ile Thr Thr Glu Glu Tyr Lys Glu Lys Ala
                245                 250                 255

Lys Lys Ile Ile Asp Ile Ile Arg Lys Leu Ala Lys Met Ala Ile Lys
                260                 265                 270

Lys Leu Glu Asp Asn Arg Thr
            275
```

<210> SEQ ID NO 39
<211> LENGTH: 153
<212> TYPE: PRT
<213> ORGANISM: Artificial Sequence
<220> FEATURE:
<223> OTHER INFORMATION: Synthetic

<400> SEQUENCE: 39

```
Lys Tyr Asp Gly Ser Lys Leu Arg Ile Gly Ile Leu His Ala Arg Trp
1               5                   10                  15

Asn Ala Glu Ile Ile Leu Ala Leu Val Leu Gly Ala Leu Lys Arg Leu
            20                  25                  30

Gln Glu Phe Gly Val Lys Arg Glu Asn Ile Ile Ile Glu Thr Val Pro
        35                  40                  45

Gly Ser Phe Glu Leu Pro Tyr Gly Ser Lys Leu Phe Val Glu Lys Gln
    50                  55                  60

Lys Arg Leu Gly Lys Pro Leu Asp Ala Ile Ile Pro Ile Gly Val Leu
65                  70                  75                  80

Ile Lys Gly Ser Thr Met His Phe Glu Tyr Ile Cys Asp Ser Thr Thr
                85                  90                  95

His Gln Leu Met Lys Leu Asn Phe Glu Leu Gly Ile Pro Val Ile Phe
            100                 105                 110

Gly Val Leu Thr Cys Leu Thr Asp Glu Gln Ala Glu Ala Arg Ala Gly
        115                 120                 125

Leu Ile Glu Gly Lys Met His Asn His Gly Glu Asp Trp Gly Ala Ala
    130                 135                 140

Ala Val Glu Met Ala Thr Lys Phe Asn
145                 150
```

<210> SEQ ID NO 40
<211> LENGTH: 119
<212> TYPE: PRT
<213> ORGANISM: Artificial Sequence
<220> FEATURE:
<223> OTHER INFORMATION: Synthetic

<400> SEQUENCE: 40

```
Glu Glu Ala Glu Leu Ala Tyr Leu Leu Gly Glu Leu Ala Tyr Lys Leu
1               5                   10                  15
```

```
Gly Glu Tyr Arg Ile Ala Ile Arg Ala Tyr Arg Ile Ala Leu Lys Arg
            20                  25                  30

Asp Pro Asn Asn Ala Glu Ala Trp Tyr Asn Leu Gly Asn Ala Tyr Tyr
            35                  40                  45

Lys Gln Gly Arg Tyr Arg Glu Ala Ile Glu Tyr Tyr Gln Lys Ala Leu
        50                  55                  60

Glu Leu Asp Pro Asn Asn Ala Glu Ala Trp Tyr Asn Leu Gly Asn Ala
65                  70                  75                  80

Tyr Tyr Glu Arg Gly Glu Tyr Glu Glu Ala Ile Glu Tyr Tyr Arg Lys
            85                  90                  95

Ala Leu Arg Leu Asp Pro Asn Asn Ala Asp Ala Met Gln Asn Leu Leu
            100                 105                 110

Asn Ala Lys Met Arg Glu Glu
            115
```

<210> SEQ ID NO 41
<211> LENGTH: 136
<212> TYPE: PRT
<213> ORGANISM: Artificial Sequence
<220> FEATURE:
<223> OTHER INFORMATION: Synthetic

<400> SEQUENCE: 41

```
Asn Asp Ala Glu Ala Trp Lys Glu Leu Gly Lys Val Leu Glu Lys Leu
1               5                   10                  15

Gly Arg Leu Asp Trp Ala Ala Glu Ala Tyr Lys Lys Ala Ile Glu Leu
            20                  25                  30

Asp Pro Asn Asp Ala Glu Ala Trp Lys Glu Leu Gly Lys Val Leu Glu
            35                  40                  45

Lys Leu Gly Arg Leu Asp Glu Ala Ala Glu Ala Tyr Lys Lys Ala Ile
        50                  55                  60

Glu Leu Asp Pro Asn Asp Ala Glu Ala Trp Lys Glu Leu Gly Lys Val
65                  70                  75                  80

Leu Glu Lys Leu Gly Arg Leu Asp Glu Ala Ala Glu Ala Tyr Lys Lys
            85                  90                  95

Ala Ile Glu Leu Asp Pro Asn Asp Ala Glu Ala Trp Lys Glu Leu Gly
            100                 105                 110

Lys Val Leu Glu Lys Leu Gly Arg Leu Asp Glu Ala Ala Glu Ala Tyr
            115                 120                 125

Lys Lys Ala Ile Glu Leu Asp Pro
        130                 135
```